(12) United States Patent
Dai et al.

(10) Patent No.: US 9,364,482 B2
(45) Date of Patent: Jun. 14, 2016

(54) SUBSTITUTED BENZOFURAN COMPOUNDS AND METHODS OF USE THEREOF FOR THE TREATMENT OF VIRAL DISEASES

(71) Applicant: Merck Sharp & Dohme Corp., Rahway, NJ (US)

(72) Inventors: Xing Dai, Cranford, NJ (US); Hong Liu, Hillsborough, NJ (US); Anandan Palani, Bridgewater, NJ (US); Shuwen He, Fanwood, NJ (US); Ravi Nargund, East Brunswick, NJ (US); Dong Xiao, Warren, NJ (US); Nicolas Zorn, Durmenach (FR); Qun Dang, Westfield, NJ (US); Casey C. McComas, Phoenixville, PA (US); Xuanjia Peng, Shanghai (CN); Peng Li, Shanghai (CN); Richard Soll, Middleton, MA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 14/898,768

(22) PCT Filed: Jun. 19, 2014

(86) PCT No.: PCT/US2014/043072
§ 371 (c)(1),
(2) Date: Dec. 16, 2015

(87) PCT Pub. No.: WO2014/209727
PCT Pub. Date: Dec. 31, 2014

(65) Prior Publication Data
US 2016/0136172 A1    May 19, 2016

(30) Foreign Application Priority Data

Jun. 24, 2013 (WO) ................ PCT/CN2013/000746

(51) Int. Cl.
| | |
|---|---|
| *A61K 31/65* | (2006.01) |
| *A61K 31/519* | (2006.01) |
| *A61K 31/517* | (2006.01) |
| *A61K 31/437* | (2006.01) |
| *A61K 31/4725* | (2006.01) |
| *A61K 31/06* | (2006.01) |
| *C07D 498/04* | (2006.01) |
| *C07D 471/04* | (2006.01) |
| *C07D 405/04* | (2006.01) |
| *C07D 475/02* | (2006.01) |
| *C07D 405/14* | (2006.01) |
| *A61K 31/5365* | (2006.01) |
| *A61K 31/53* | (2006.01) |
| *A61K 45/06* | (2006.01) |

(52) U.S. Cl.
CPC ........... *A61K 31/5365* (2013.01); *A61K 31/437* (2013.01); *A61K 31/4725* (2013.01); *A61K 31/517* (2013.01); *A61K 31/519* (2013.01); *A61K 31/53* (2013.01); *A61K 45/06* (2013.01); *C07D 405/04* (2013.01); *C07D 405/14* (2013.01); *C07D 471/04* (2013.01); *C07D 475/02* (2013.01); *C07D 498/04* (2013.01)

(58) Field of Classification Search
None
See application file for complete search history.

(56) References Cited

U.S. PATENT DOCUMENTS

| | | | |
|---|---|---|---|
| 2004/0162318 | A1 | 8/2004 | Saha et al. |
| 2009/0081636 | A1 | 3/2009 | Huang |
| 2010/0093694 | A1 | 4/2010 | Yeung et al. |

FOREIGN PATENT DOCUMENTS

| | | |
|---|---|---|
| WO | WO2008082484 | 7/2008 |
| WO | WO2008082488 | 7/2008 |
| WO | WO2008136815 | 11/2008 |
| WO | WO2009032116 | 3/2009 |
| WO | WO2009032123 | 3/2009 |
| WO | WO2009032124 | 3/2009 |
| WO | WO2009032125 | 3/2009 |
| WO | WO2011106992 | 9/2011 |
| WO | WO2013033971 | 3/2013 |
| WO | WO2014209726 | 12/2014 |
| WO | WO2014209729 | 12/2014 |

OTHER PUBLICATIONS

Beaulieu et al., Inhibitors of the HCV NS5B polymerase: New hope for the treatment of hepatitis C infections, Current Opinions in Investigational Drugs, 2004, 838, 5.
Carroll et al., Inhibition of Hepatitis C Virus RNA Replication by 2'-Modified Nucleoside Analogs, J. Biol. Chem., 2003, 11979-11984, 278(14).
Ni et al., Progress and Development of Small Molecule HCV Antivirals, Current Opinion in Drug Discovery and Development, 2004, 446, 7(4).
PubChem. Compound Summary for: CID 71509596. Create Date: Jun. 10, 2013 [retrieved on Sep. 8, 2014]. Retrieved from the Internet. <URL: https://pubchem.ncbi.nlm.nih.gov/summary/summary.cgi?cid=71509596&from=compound.
Behrens, Identification and properties of the RNA-dependnt RNA polymerase of hepatitis C virus, EMBO. J., 1996, 12-22, 15(1).
Tan et al., Hepatitis C Therapeutics: Current Status and Emerging Strategies, Nature Reviews, 2002, 867-881, 1.

*Primary Examiner* — Yevegeny Valenrod
(74) *Attorney, Agent, or Firm* — Alysia A. Finnegan; Gloria Fuentes

(57) ABSTRACT

The present invention relates to compounds of formula I that are useful as hepatitis C virus (HCV) NS5B polymerase inhibitors, the synthesis of such compounds, and the use of such compounds for inhibiting HCV NS5B polymerase activity, for treating or preventing HCV infections and for inhibiting HCV viral replication and/or viral production in a cell-based system. (I)

15 Claims, No Drawings

SUBSTITUTED BENZOFURAN COMPOUNDS AND METHODS OF USE THEREOF FOR THE TREATMENT OF VIRAL DISEASES

CROSS-REFERENCE TO RELATED APPLICATIONS

This application is a §371 National Stage Application of PCT/US2014/043072, international filing date of Jun. 19, 2014, which claims the benefit of International Application No. PCT/CN2013/000746, filed Jun. 24, 2013, now expired.

FIELD OF THE INVENTION

The present disclosure relates to compounds that are useful as inhibitors of the hepatitis C virus (HCV) NS5B (non-structural protein 5B) polymerase, compositions comprising such compounds, the use of such compounds for treating HCV infection and/or reducing the likelihood or severity of symptoms of HCV infection, methods for inhibiting the function of the NS5B polymerase, and methods for inhibiting HCV viral replication and/or viral production.

BACKGROUND OF THE INVENTION

Hepatitis C virus (HCV) infection is a major health problem that leads to chronic liver disease, such as cirrhosis and hepatocellular carcinoma, in a substantial number of infected individuals. Current treatments for HCV infection include immunotherapy with recombinant interferon-α alone or in combination with the nucleoside analog ribavirin.

Several virally-encoded enzymes are putative targets for therapeutic intervention, including a metalloprotease (NS2-3), a serine protease (NS3, amino acid residues 1-180), a helicase (NS3, full length), an NS3 protease cofactor (NS4A), a membrane protein (NS4B), a zinc metalloprotein (NS5A) and an RNA-dependent RNA polymerase (NS5B).

One identified target for therapeutic intervention is HCV NS5B polymerase. Sven-Erik Behrens et al., *Identification and properties of the RNA-dependent RNA polymerase of hepatitis C virus*, 15(1) EMBO J. 12-22 (1996). Antagonists of NS5B activity are inhibitors of HCV replication. Steven S. Carroll et al., *Inhibition of Hepatitis C Virus RNA Replication by 2'-Modified Nucleoside Analogs*, 278(14) J. BIOL. CHEM. 11979-84 (2003).

There is a clear and long-felt need to develop effective therapeutics for treatment of HCV infection. Specifically, there is a need to develop compounds that inhibit HCV viral replication and that would be useful for treating HCV-infected patients.

SUMMARY OF THE INVENTION

The present disclosure relates to novel compounds of formula I and pharmaceutically acceptable salts thereof. These compounds are useful, either as compounds or their pharmaceutically acceptable salts (when appropriate), in the inhibition of HCV (hepatitis C virus) NS5B (non-structural 5B) polymerase, the prevention or treatment of one or more of the symptoms of HCV infection, the inhibition of HCV viral replication and/or HCV viral production, and/or as pharmaceutical composition ingredients. As pharmaceutical composition ingredients, these compounds and their salts may be the primary active therapeutic agent, and, when appropriate, may be combined with other therapeutic agents including but not limited to other HCV antivirals, anti-infectives, immuno-modulators, antibiotics or vaccines, as well as the present Standard of Care treatment options for HCV.

In one aspect, the present invention relates to a compound of formula I:

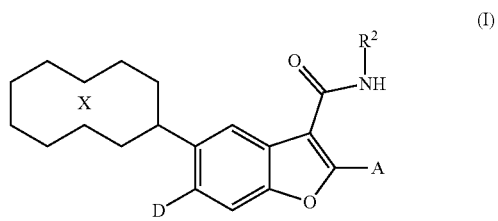

or a pharmaceutically acceptable salt thereof,
wherein:
X is

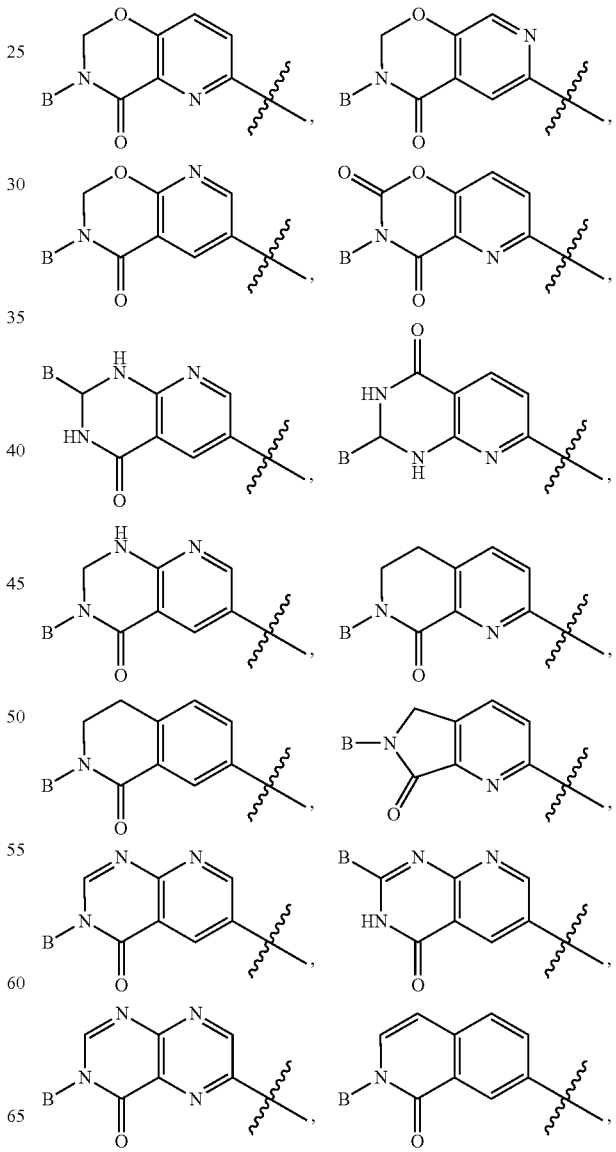

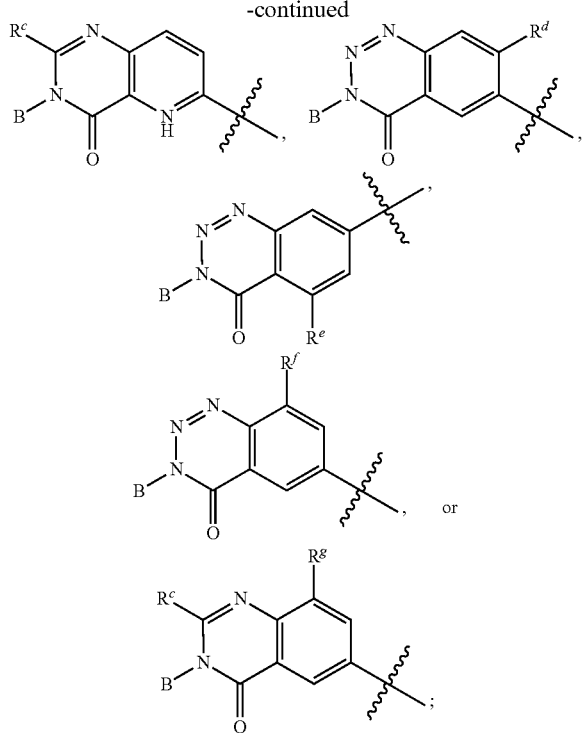

A is fluorophenyl;
B is a) hydrogen;
b) Ar;
c) $C_1$-$C_6$ alkyl-Ar;
d) —$CHR^a$—Ar; or
e) cyclopropyl;
Ar is a 5-6 membered monocyclic aromatic ring with 0 or 1 heteroatom ring atoms independently selected from N and S, optionally substituted with 1 or 2 substituents independently selected from $C_1$-$C_6$ alkoxy, halo, and cyano;
D is H or $NR^3SO_2R^4$;
$R^2$ is $C_1$-$C_6$ alkyl;
$R^3$ is $C_1$-$C_6$ alkyl;
$R^4$ is $C_1$-$C_6$ alkyl;
$R^a$ is $C_1$-$C_6$ hydroxyalkyl, or alkylalkoxy;
$R^c$ is hydrogen, $C_1$-$C_6$ alkyl, alkylalkoxy, or —$CH_2NHC(O)CH_3$;
$R^d$ is hydrogen, F, Cl or $C_1$-$C_6$ alkyl;
$R^e$ and $R^f$ are independently hydrogen or $C_1$-$C_6$ alkyl; and
$R^g$ is hydrogen or $C_1$-$C_6$ alkoxy.

The present invention also includes pharmaceutical compositions containing a compound of the present invention and methods of preparing such pharmaceutical compositions. The present invention further includes methods of treating or reducing the likelihood or severity of HCV infection, methods for inhibiting the activity of the NS5B polymerase, and methods for inhibiting HCV viral replication and/or viral production.

Other embodiments, aspects and features of the present invention are either further described in or will be apparent from the ensuing description, examples and appended claims.

DETAILED DESCRIPTION OF THE INVENTION

The present invention includes compounds of formula I above, and pharmaceutically acceptable salts thereof. The compounds of formula I are HCV NS5B polymerase inhibitors.

In a first embodiment of the invention, $R^2$, $R^3$ and $R^4$ are methyl, and the other groups are as provided in the general formula above.

In a second embodiment of the invention, D is $N(CH_3)SO_2CH_3$, and the other groups are as provided in the general formula above, or as in the first embodiment.

In a third embodiment of the invention, each halo is F, and the other groups are as provided in the general formula above, or as in the first or second embodiments.

In a fourth embodiment of the invention, B is —$CH_2$—Ar, —$CH_2CH_2$—Ar, —$CH(CH_3)$—Ar, or —$C(CH_3)_2$—Ar, and the other groups are as provided in the general formula above, or as in the first through third embodiments.

In a fifth embodiment of the invention, the compound of the invention has the formula:

(Ia)

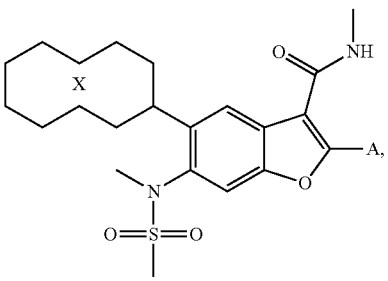

or a pharmaceutically acceptable salt thereof, and the groups are as provided in the general formula above, or as in the first through fourth embodiments.

In a sixth embodiment of the invention, X is

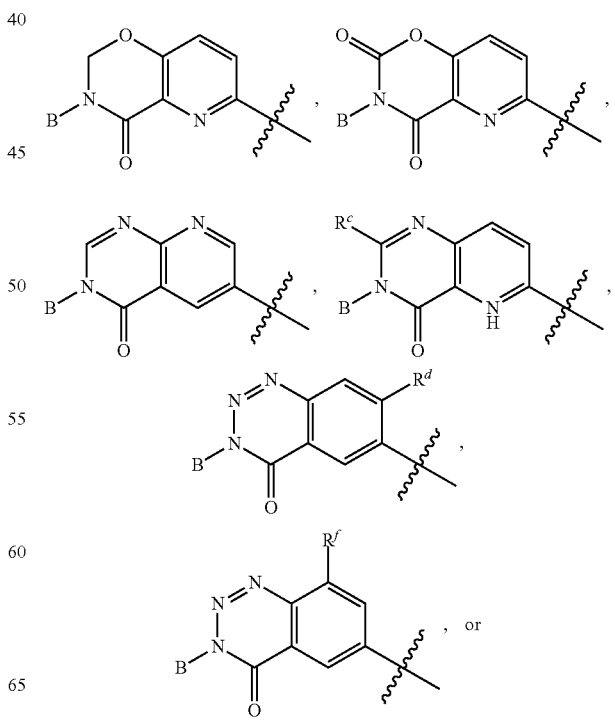

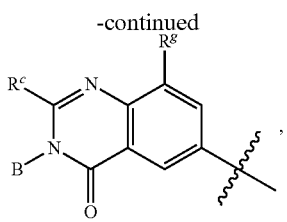

and the other groups are as provided in the general formula above, or as in the first through fifth embodiments.

In a seventh embodiment of the invention, $R^c$ is hydrogen or methyl and $R^g$ is hydrogen, and the other groups are as provided in the general formula above, or as in the first through sixth embodiments.

In an eighth embodiment of the invention, B is hydrogen; phenyl; fluorophenyl; —$(CH_2)_{1-2}$-phenyl; —$CH_2$-fluorophenyl; —$CH(CH_3)$-fluorophenyl; —$C(CH_3)_2$-fluorophenyl; —$CH_2$-chlorophenyl; —$CH_2$-phenyl-$OCH_3$; —$CH_2$-phenyl-cyano; —$CH_2$-fluoropyridine; thiophene; cyclopropyl; —$CH(CH_2OCH_3)$-fluorophenyl; —$CH(CH_2OH)$-phenyl; —$CH(CH_2OH)$-fluorophenyl; —$CH(CH_2CH_2OH)$-fluorophenyl; —$CH_2$-4-fluoro-2-methoxyphenyl; or —$CH_2$-difluorophenyl, and the other groups are as provided in the general formula above, or as in the first through third or fifth to seventh embodiments.

In certain aspects of the invention, a fluorophenyl is para-fluorophenyl.

In another embodiment of the invention, the compound of the invention is selected from the exemplary species depicted in Examples 1-74 shown below, and pharmaceutically acceptable salts thereof Other embodiments of the present invention include the following:

(a) A pharmaceutical composition comprising an effective amount of a compound of formula I and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(d) A pharmaceutical combination that is (i) a compound of formula I and (ii) a second therapeutic agent selected from the group consisting of HCV antiviral agents, immunomodulators, and anti-infective agents; wherein the compound of formula I and the second therapeutic agent are each employed in an amount that renders the combination effective for inhibiting HCV NS5B activity, or for inhibiting HCV viral replication, or for treating HCV infection and/or reducing the likelihood or severity of symptoms of HCV infection.

(e) The combination of (d), wherein the HCV antiviral agents are one or more antiviral agents selected from the group consisting of direct inhibitors of HCV, including but not limited to NS3 and NS3/4A protease inhibitors, NS5A inhibitors and HCV NS5B polymerase inhibitors.

(f) A use of a compound of formula I in the preparation of a medicament for inhibiting HCV NS5B activity in a subject in need thereof.

(g) A use of a compound of formula I in the preparation of a medicament for preventing and/or treating infection by HCV in a subject in need thereof.

(h) A method of treating HCV infection and/or reducing the likelihood or severity of symptoms of HCV infection in a subject in need thereof, which comprises administering to the subject an effective amount of a compound of formula I.

(i) The method of (h), wherein the compound of formula I is administered in combination with an effective amount of at least one second therapeutic agent selected from the group consisting of HCV antiviral agents, immunomodulators, and anti-infective agents.

(j) The method of (i), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(k) A method of inhibiting HCV viral replication and/or HCV viral production in a cell-based system, which comprises administering to the subject an effective amount of a compound of formula I in combination with an effective amount of at least one second therapeutic agent selected from the group consisting of HCV antiviral agents, immunomodulators, and anti-infective agents.

(l) The method of (k), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(m) A method of inhibiting HCV NS5B activity in a subject in need thereof, which comprises administering to the subject the pharmaceutical composition of (a), (b), or (c) or the combination of (d) or (e).

(n) A method of treating HCV infection and/or reducing the likelihood or severity of symptoms of HCV infection in a subject in need thereof, which comprises administering to the subject the pharmaceutical composition of (a), (b), or (c) or the combination of (d) or (e).

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (n) above are understood to include all embodiments of the compounds and/or salts, including such embodiments as result from combinations of embodiments.

Additional embodiments of the invention include the pharmaceutical compositions, combinations, uses and methods set forth in (a) through (n) above, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

The present invention also includes a compound of the present invention for use (i) in, (ii) as a medicament for, or (iii) in the preparation of a medicament for: (a) inhibiting HCV NS5B activity, or (b) inhibiting HCV viral replication, or (c) treating HCV infection and/or reducing the likelihood or severity of symptoms of HCV infection, or (d) use in medicine. In these uses, the compounds of the present invention can optionally be employed in combination with one or more second therapeutic agents selected from HCV antiviral agents, anti-infective agents, and immunomodulators.

Chemical names, common names, and chemical structures may be used interchangeably to describe the same structure. If a chemical compound is referred to using both a chemical structure and a chemical name and an ambiguity exists between the structure and the name, the structure is understood to predominate.

As used herein, the term "administration" and variants thereof (e.g., "administering" a compound) in reference to a compound of the invention mean providing the compound to the individual in need of treatment. When a compound of the invention is provided in combination with one or more other active agents (e.g., antiviral agents useful for treating HCV infection), "administration" and its variants are each understood to include concurrent and sequential provision of the compound or salt and other agents.

As used herein, the term "alkoxy" refers to an "alkyl-O—" group. Alkoxy groups may be substituted as indicated.

The term "alkyl" refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

The term "aryl" (or "aryl ring system") refers to aromatic mono- and poly-carbocyclic ring systems wherein the individual carbocyclic rings in the polyring systems are fused or attached to each other via a single bond. As used herein, the term aryl includes aromatic mono- and poly-carbocyclic ring systems that include from 0 to 4 heteroatoms (non-carbon atoms) that are independently chosen from N, O and S. Suitable aryl groups include phenyl, naphthyl, biphenylenyl, pyridinyl, pyrimidinyl and pyrrolyl, as well as those discussed below. Aryl ring systems may include, where appropriate, an indication of the variable to which a particular ring atom is attached. Unless otherwise indicated, substituents to the aryl ring systems can be attached to any ring atom, provided that such attachment results in formation of a stable ring system.

The term "composition" is intended to encompass a product comprising the specified ingredients, as well as any product which results from combining the specified ingredients.

The term "compound" is intended to encompass chemical agents described by generic formula I in all forms. Such chemical agents can be present in different forms such as hydrates and solvates.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl, bicyclo[3.1.0]hexyl and adamantyl. The term "3 to 7-membered cycloalkyl" refers to a cycloalkyl group having from 3 to 7 ring carbon atoms. A ring carbon atom of a cycloalkyl group may be functionalized as a carbonyl group. An illustrative example of such a cycloalkyl group (also referred to herein as a "cycloalkanoyl" group) includes, but is not limited to cyclobutanoyl:

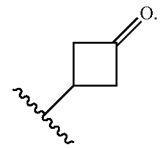

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity or likelihood of one or more symptoms of the disease or condition. In another embodiment, the effective amount is a "therapeutically effective amount" for inhibition of HCV viral replication and/or HCV viral production. The term also includes herein the amount of active compound sufficient to inhibit HCV NS5B activity and thereby elicit the response being sought (i.e., an "inhibition effective amount"). When the active compound (i.e., active ingredient) is administered as the salt, references to the amount of active ingredient are to the free acid or free base form of the compound.

The term "halogen" (or "halo") refers to atoms of fluorine, chlorine, bromine and iodine (alternatively referred to as fluoro, chloro, bromo, and iodo).

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic and has 9 or 10 ring atoms. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. The term "heteroaryl" also encompasses any fused polycyclic ring system containing at least one ring heteroatom selected from N, O and S, wherein at least one ring of the fused polycyclic ring system is aromatic. For example, the term "9 to 10-membered bicyclic heteroaryl" encompasses a non-aromatic 5 membered heterocyclic ring that is fused to a benzene or pyridyl ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

As used herein, the term "oxo" or "=O" forms a carbonyl moiety with the carbon atom to which it is attached.

By "pharmaceutically acceptable" is meant that the ingredients of the pharmaceutical composition must be compatible with each other and not deleterious to the recipient thereof The term "preventing," as used herein with respect to an HCV viral infection or HCV-virus related disorder, refers to reducing the likelihood of HCV infection.

The term "subject" (alternatively referred to herein as "patient"), as used herein, refers to an animal, preferably a mammal, most preferably a human.

The term "substituted" means that one or more hydrogens on the designated atom is replaced with a selection from the indicated group, provided that the designated atom's normal valency under the existing circumstances is not exceeded, and that the substitution results in a stable compound. Unless expressly stated to the contrary, substitution by a named substituent is permitted on any atom provided such substitution is chemically allowed and results in a stable compound. Combinations of substituents and/or variables are permissible only if such combinations result in stable compounds. A "stable" compound is a compound that can be prepared and isolated and whose structure and properties remain or can be caused to remain essentially unchanged for a period of time sufficient to allow use of the compound for the purposes described herein (e.g., therapeutic or prophylactic administration to a subject).

In the compounds of formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of formula I. For example, different isotopic forms of hydrogen (H) include protium ($^1$H) and deuterium ($^2$H or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within formula I can be prepared without undue experimentation by conventional techniques well known to those skilled in the art or by processes analogous to those described in the Schemes and Examples herein using appropriate isotopically-enriched reagents and/or intermediates.

Unless expressly stated to the contrary, all ranges cited herein are inclusive. For example, a heteroaryl ring described as containing from "1 to 3 heteroatoms" means the ring can contain 1, 2, or 3 heteroatoms. It is also to be understood that any range cited herein includes within its scope all of the sub-ranges within that range. The oxidized forms of the heteroatoms N and S are also included within the scope of the present invention.

When any variable (for example, R$^1$ or R$^3$) occurs more than one time in any constituent or in formula I or in any other formula depicting and describing compounds of the invention, its definition on each occurrence is independent of its definition at every other occurrence. Also, combinations of substituents and/or variables are permissible only if such combinations result in stable compounds.

Certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

Certain of the compounds of the present invention can exist as tautomers. For the purposes of the present invention a reference to a compound of formula I is a reference to the compound per se, or to any one of its tautomers per se, or to mixtures of two or more tautomers.

The compounds of the present inventions are useful in the inhibition of HCV replication (e.g., HCV NS5B activity), the treatment of HCV infection and/or reduction of the likelihood or severity of symptoms of HCV infection. For example, the compounds of this invention are useful in treating infection by HCV after suspected past exposure to HCV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for identifying resistant HCV replicon cell lines harboring mutations within NS5B, which are excellent screening tools for more powerful antiviral compounds. Furthermore, the compounds of this invention are useful in establishing or determining the binding site of other antivirals to the HCV replicase.

The compounds of the present invention may be administered in the form of pharmaceutically acceptable salts. The term "pharmaceutically acceptable salt" refers to a salt that possesses the effectiveness of the parent compound and that is not biologically or otherwise undesirable (e.g., is neither toxic nor otherwise deleterious to the recipient thereof). Suitable salts include acid addition salts that may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website).

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For the purposes of inhibiting HCV NS5B polymerase, treating HCV infection and/or reducing the likelihood or severity of symptoms of HCV infection and inhibiting HCV viral replication and/or HCV viral production, the compounds of the present invention, optionally in the form of a salt, can be administered by any means that produces contact of the active agent with the agent's site of action. They can be administered by one or more conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the following: orally, parenterally (including subcutaneous injections, intravenous, intramuscular, intrasternal injection or infusion techniques), by inhalation (such as in a spray form), or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as solubility aids. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, 18$^{th}$ edition (ed. A. R. Gennaro, Mack Publishing Co., 1990).

The compounds of this invention can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 mg of the active ingredient, particularly 1, 5, 10, 15, 20, 25, 50, 75, 100, 150, 200, 250, 300, 400, and 500 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, HCV viral genotype, viral resistance, and the host undergoing therapy.

As noted above, the present invention also relates to a method of inhibiting HCV NS5B activity, inhibiting HCV viral replication and/or HCV viral production, treating HCV infection and/or reducing the likelihood or severity of symptoms of HCV infection with a compound of the present invention in combination with one or more therapeutic agents and a pharmaceutical composition comprising a compound of the present invention and one or more therapeutic agents selected from the group consisting of a HCV antiviral agent, an immunomodulator, and an anti-infective agent. Such agents are described in detail below.

HCV polymerase inhibitors useful in the present compositions and methods include, but are not limited to, VP-19744 (Wyeth/ViroPharma), PSI-7851 (Pharmasset), RG7128 (Roche/Pharmasset), PSI-7977 (Pharmasset), PSI-938 (Pharmasset), PSI-879 (Pharmasset), PSI-661 (Pharmasset), PF-868554/filibuvir (Pfizer), VCH-759NX-759 (ViroChem Pharma/Vertex), HCV-371 (Wyeth/VirroPharma), HCV-796 (Wyeth/ViroPharma), IDX-184 (Idenix), IDX-375 (Idenix), NM-283 (Idenix/Novartis), GL-60667 (Genelabs), JTK-109 (Japan Tobacco), PSI-6130 (Pharmasset), R1479 (Roche), R-1626 (Roche), R-7128 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH-222/VX-222 (ViroChem/Vertex), VCH-916 (ViroChem), VCH-716(ViroChem), GSK-71185 (Glaxo SmithKline), ANA598 (Anadys), GSK-625433 (Glaxo SmithKline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004).

Other HCV polymerase inhibitors useful in the present compositions and methods include, but are not limited to, those disclosed in International Publication Nos. WO 08/082484, WO 08/082488, WO 08/083351, WO 08/136815, WO 09/032116, WO 09/032123, WO 09/032124 and WO 09/032125; and the following compounds:

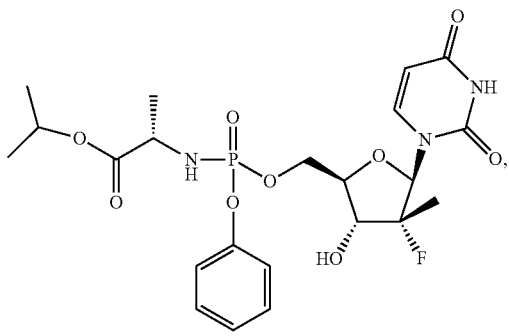

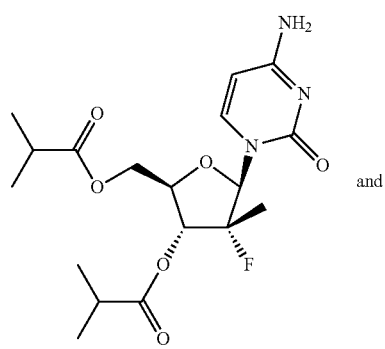

and

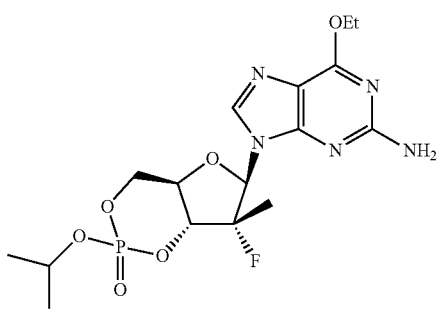

and pharmaceutically acceptable salts thereof.

Interferons useful in the present compositions and methods include, but are not limited to, interferon alfa-2a, interferon alfa-2b, interferon alfacon-1 and petroleum etherG-interferon alpha conjugates. "PEG-interferon alpha conjugates" are interferon alpha molecules covalently attached to a petroleum etherG molecule. Illustrative petroleum etherG-interferon alpha conjugates include interferon alpha-2a (Roferon™, Hoffman La-Roche, Nutley, N.J. in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name petroleum etherG-Intron™ from Schering-Plough Corporation), interferon alpha-2b-XL (e.g., as sold under the trade name petroleum etherG-Intron™), interferon alpha-2c (Berofor Alpha™, Boehringer Ingelheim, Ingelheim, Germany), petroleum etherG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus), R-7025 (Roche), IFN-α-2b-XL (Flamel Technologies), belerofon (Nautilus) and consensus interferon as defined by determination of a consensus sequence of naturally occurring interferon alphas (Infergen™, Amgen, Thousand Oaks, Calif.).

Examples of viral protease inhbitors useful in the present compositions and methods include, but are not limited to, an HCV protease inhibitor. Examples of HCV protease inhibitors useful in the present compositions and methods include, but are not limited to, VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott/Enanta), TMC-435350 (Medivir), RG7227 (Danoprevir, InterMune/Roche), EA-058 (Abbott/Enanta), EA-063 (Abbott/Enanta), GS-9256 (Gilead), IDX-320 (Idenix), ACH-1625 (Achillion), ACH-2684 (Achillion), GS-9132 (Gilead/Achillion), ACH-1095 (Gilead/Achillon), IDX-136 (Idenix), IDX-316 (Idenix), ITMN-8356 (InterMune), ITMN-8347 (InterMune), ITMN-8096 (InterMune), ITMN-7587 (InterMune), BMS-650032 (Bristol-Myers Squibb), VX-985 (Vertex) and PHX1766 (Phenomix).

Further examples of HCV protease inhibitors useful in the present compositions and methods include, but are not limited to, the following compounds:

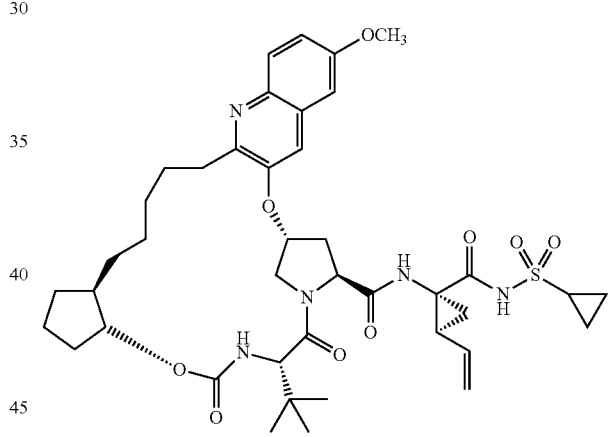

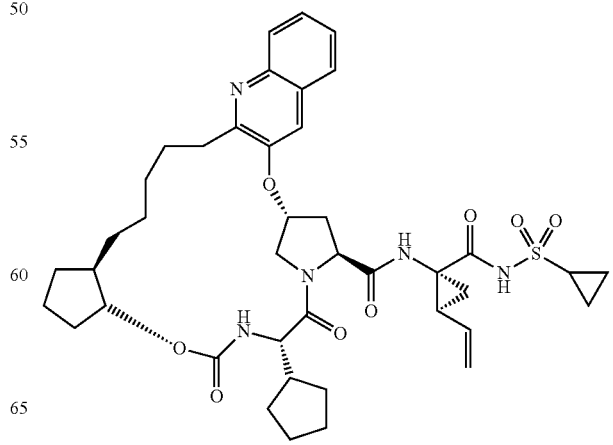

-continued
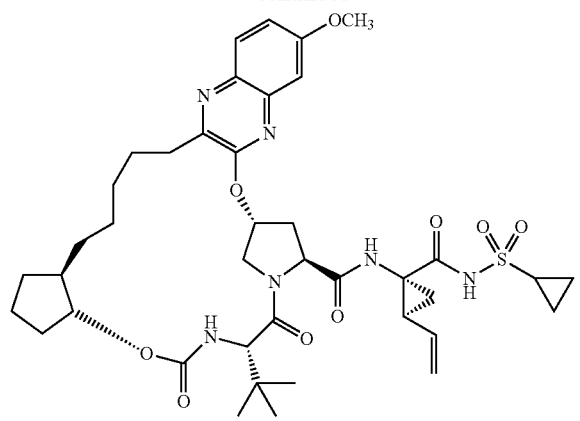
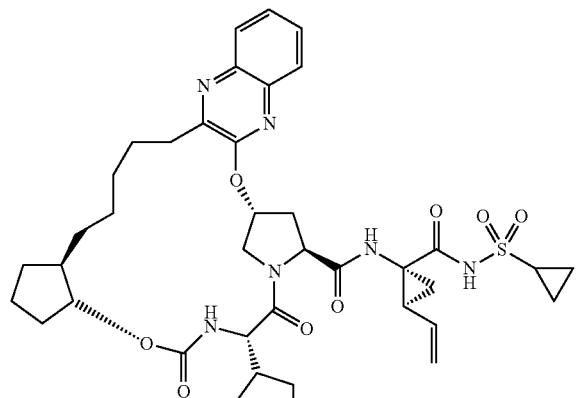
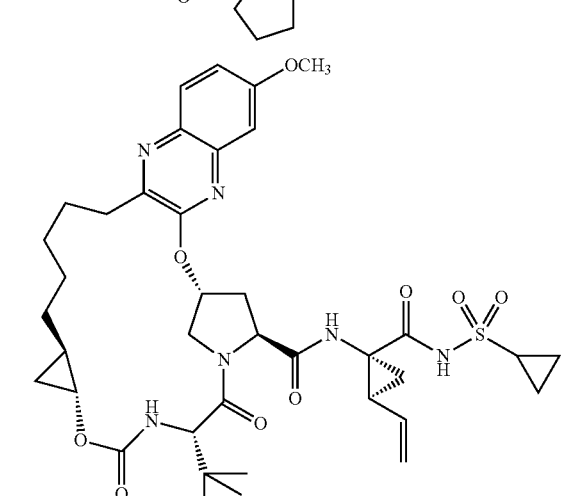
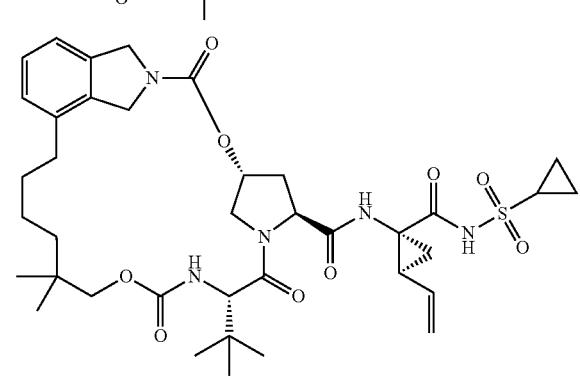
-continued
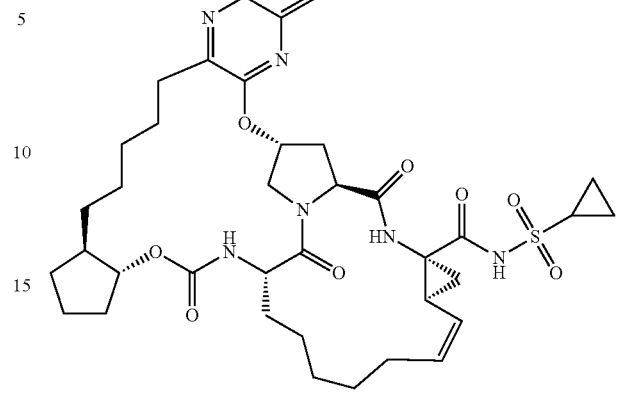
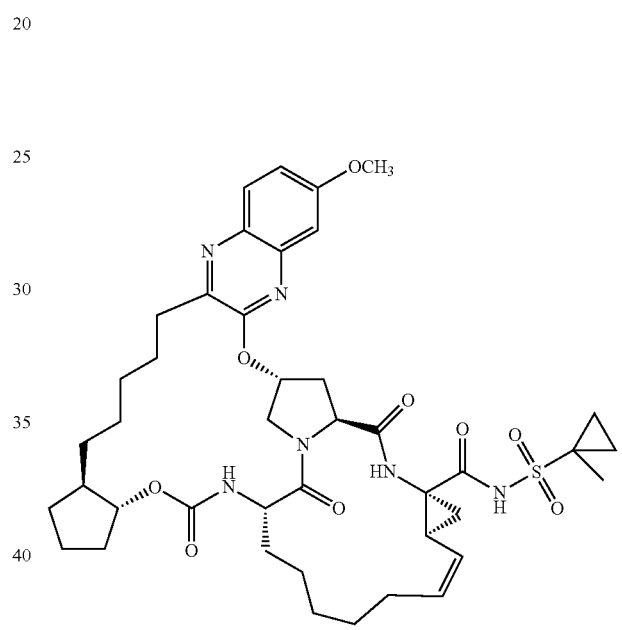
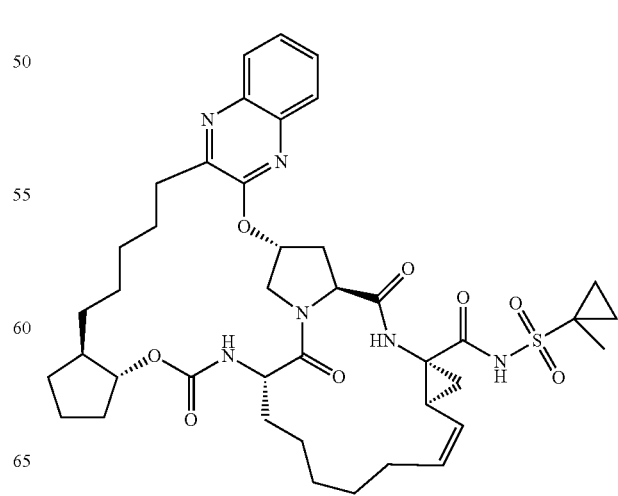

17
-continued
18
-continued
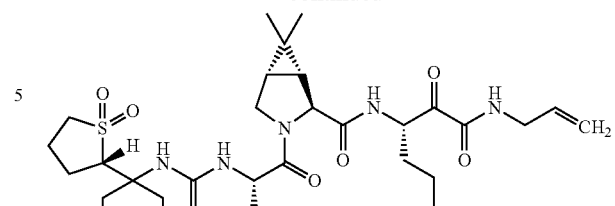
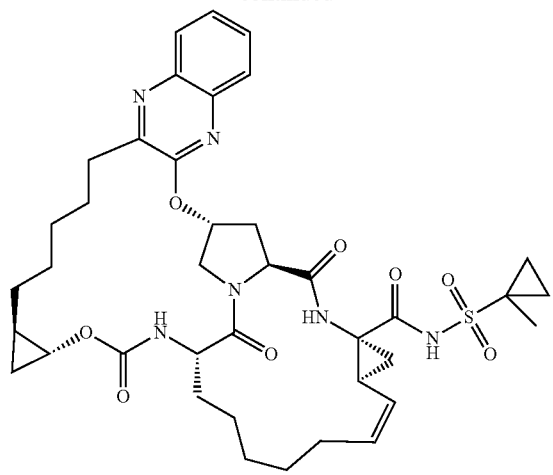
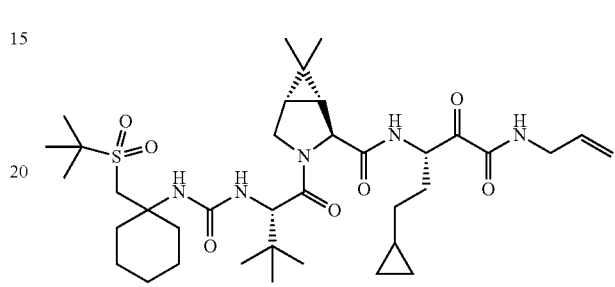
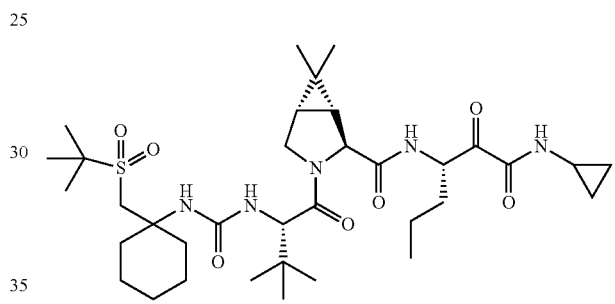
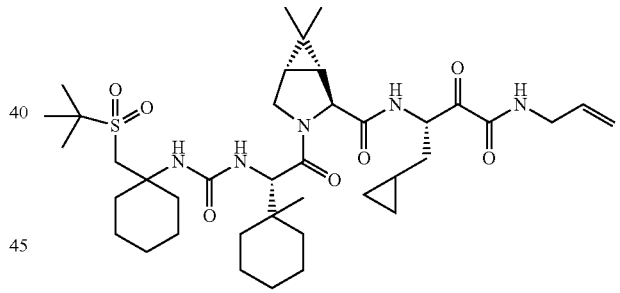
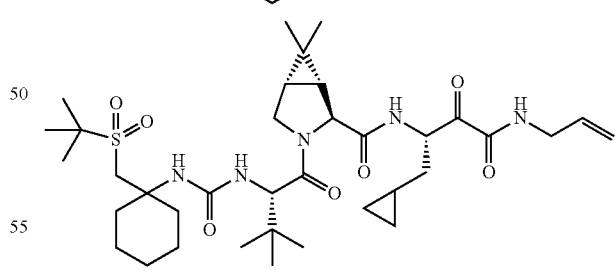
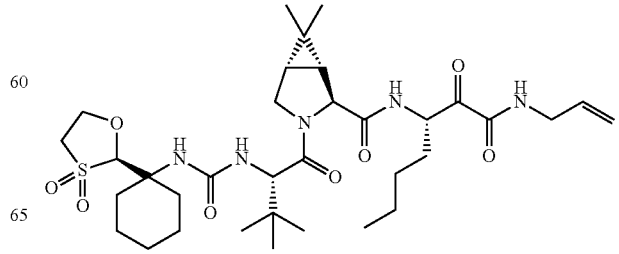

-continued
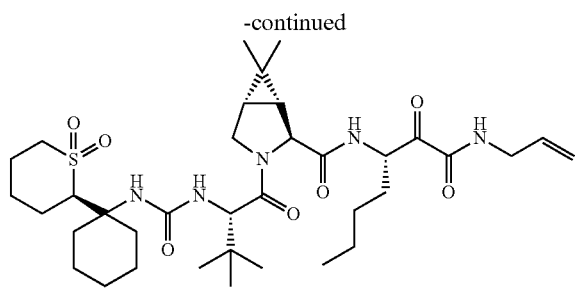
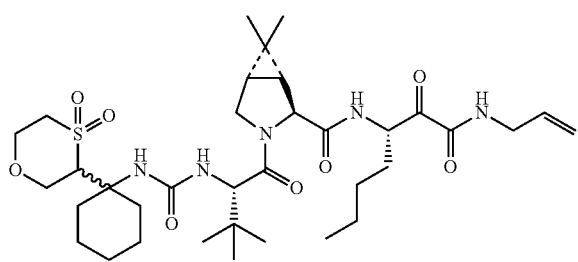
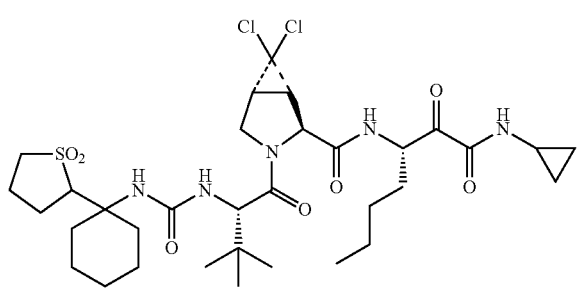
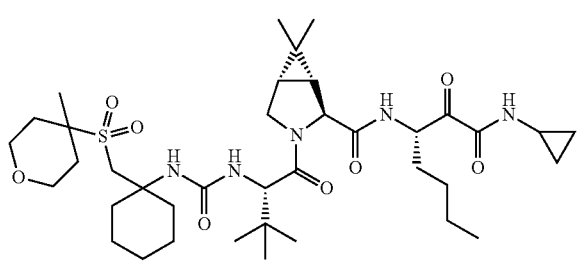
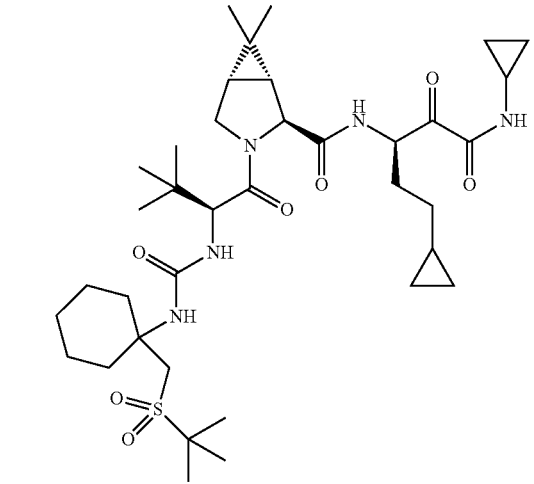
-continued
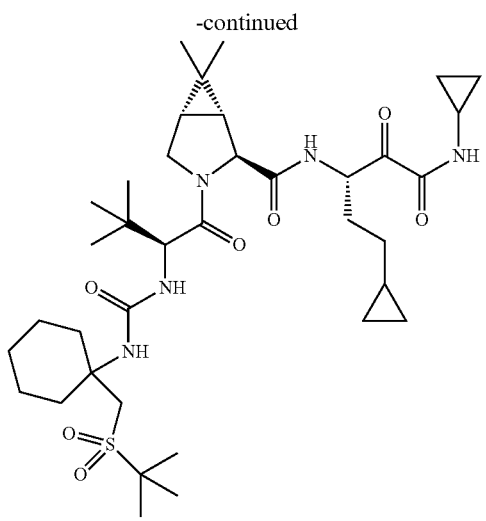
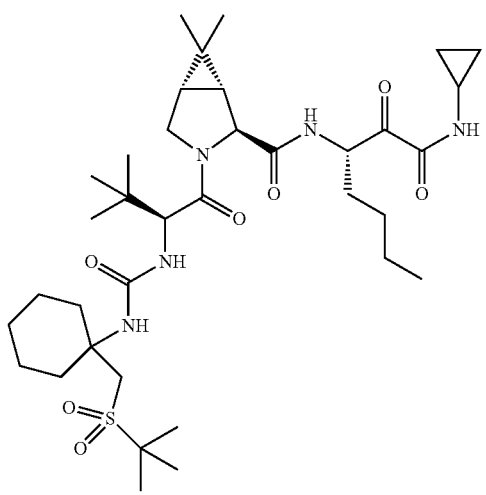
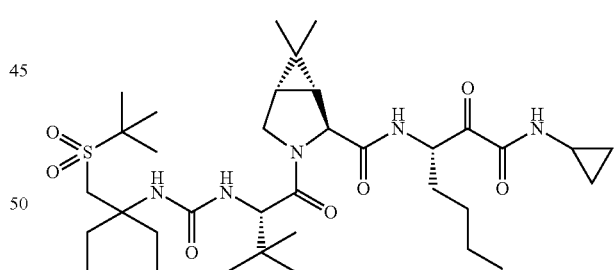
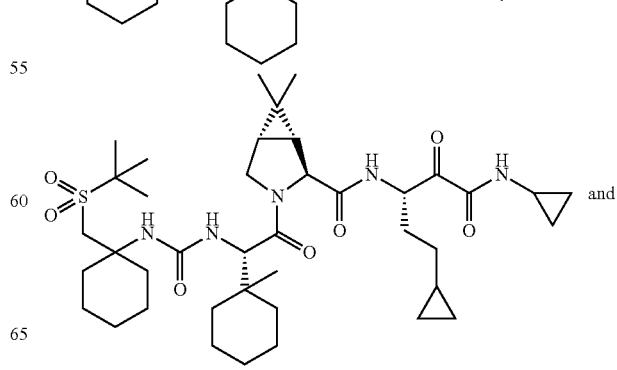
and -continued

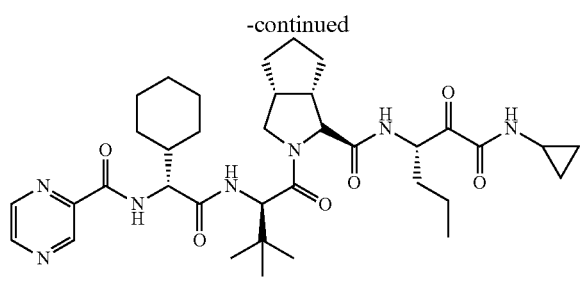

and pharmaceutically acceptable salts thereof.

Viral replication inhibitors useful in the present compositions and methods include, but are not limited to, HCV replicase inhibitors, IRES inhibitors, NS4A inhibitors, NS3 helicase inhibitors, NS5A inhibitors, NS5B inhibitors, ribavirin, AZD-2836 (Astra Zeneca), viramidine, A-831 (Arrow Therapeutics), EDP-239 (Enanta), ACH-2928 (Achillion), GS-5885 (Gilead); an antisense agent or a therapeutic vaccine.

HCV NS5A inhibitors useful in the present compositions and methods include, but are not limited to, ACH-2928 (Achilon), A-832 (Arrow Therpeutics), AZD-7295 (Astra Zeneca/Arrow), GS-5885 (Gilead), PPI-461 (Presidio), PPI-1301 (Presidio), BMS-824383 (Bristol-Myers Squibb) and BMS-790052 (Bristol-Myers Squibb). Additional HCV NS5A inhibitors useful as second additional therapeutic agents in the present compositions and methods include, but are not limited to those disclosed in International Publication No. WO 2010/111483 and the following compounds:

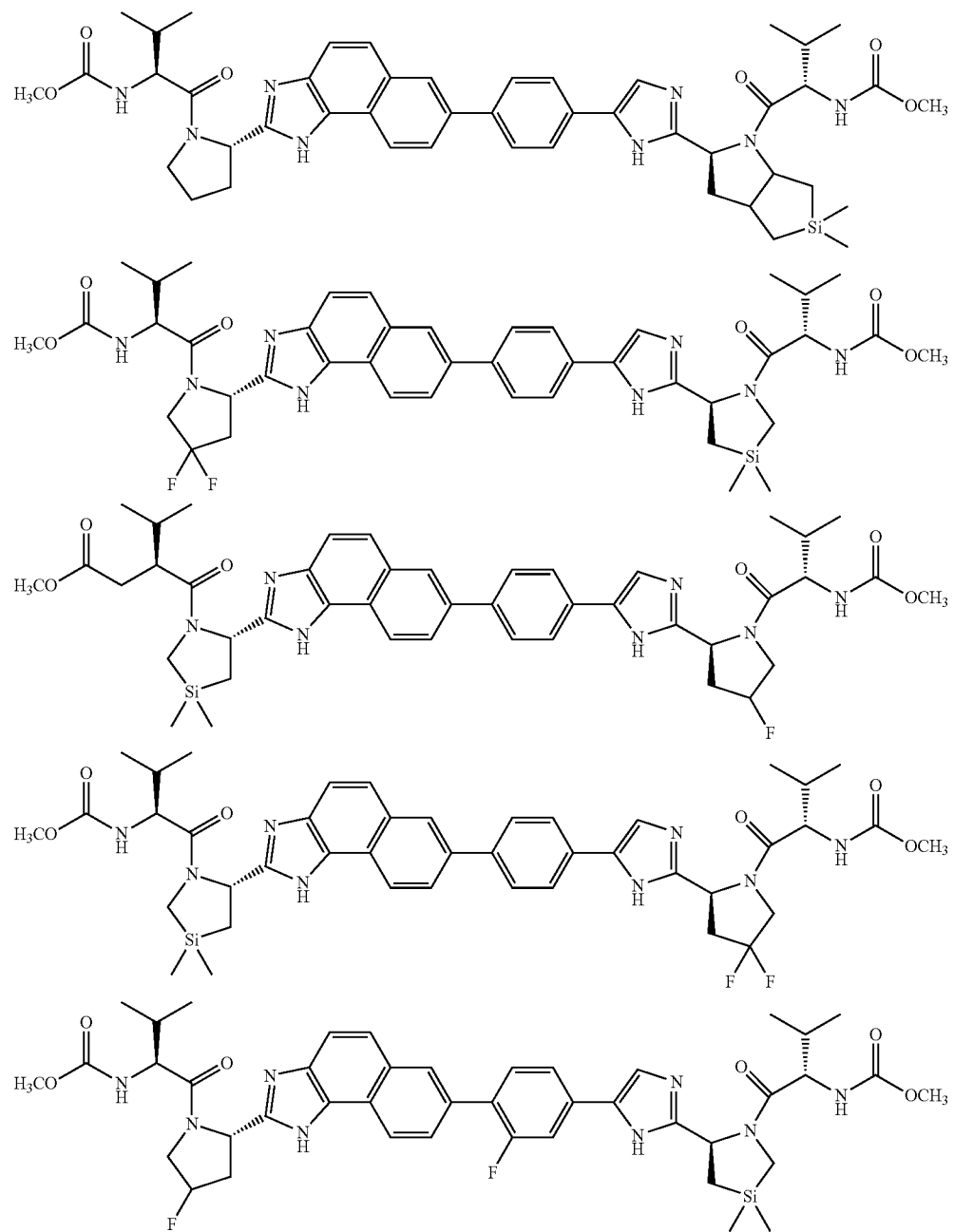

-continued
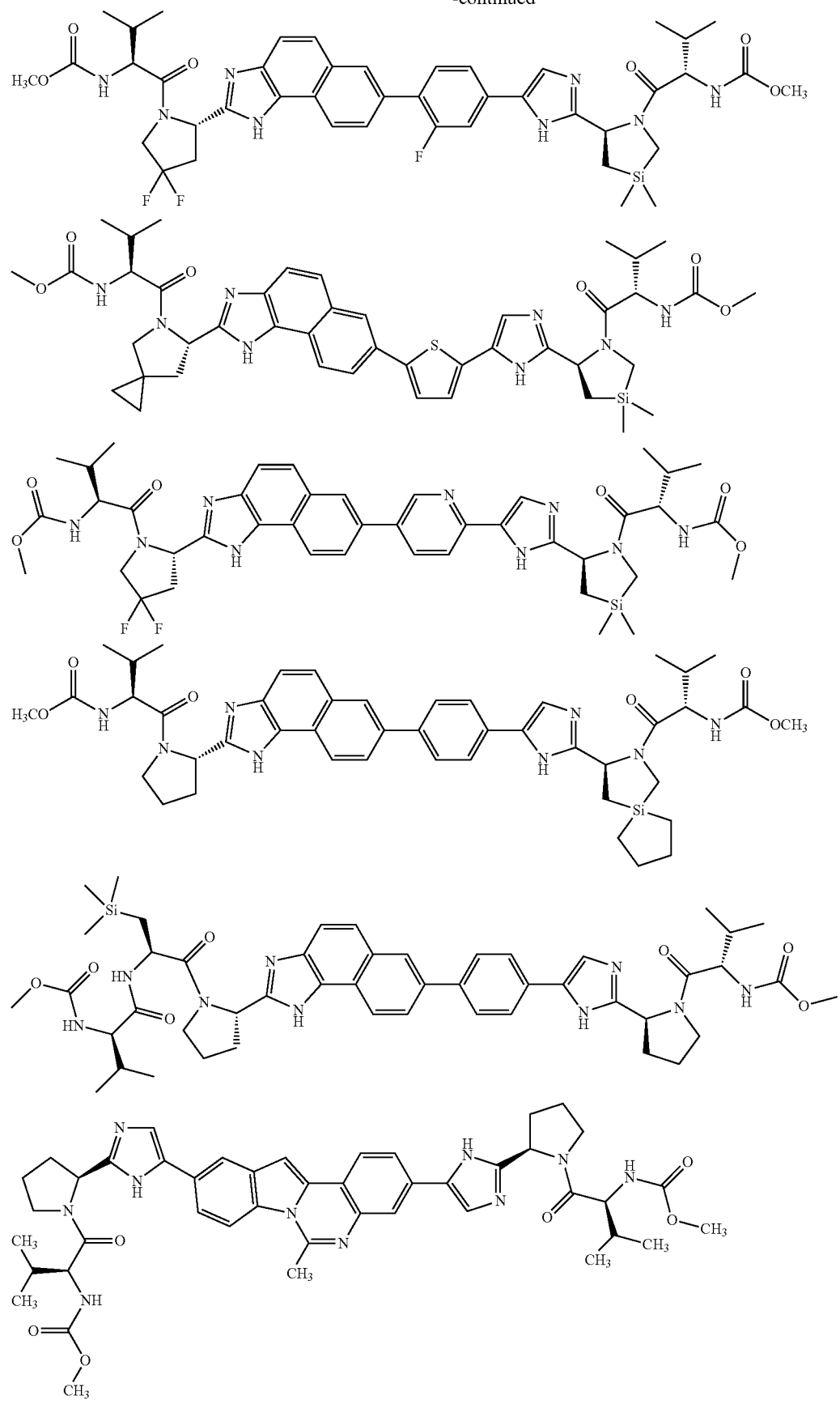

-continued
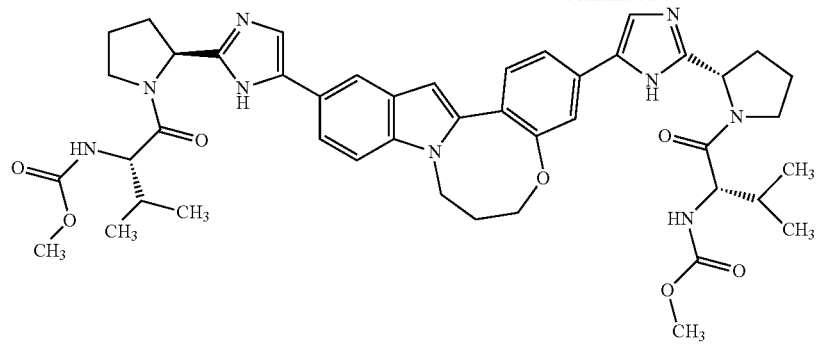
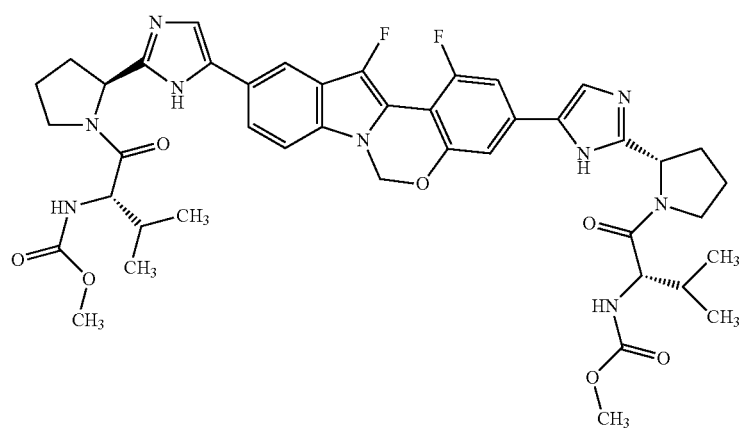
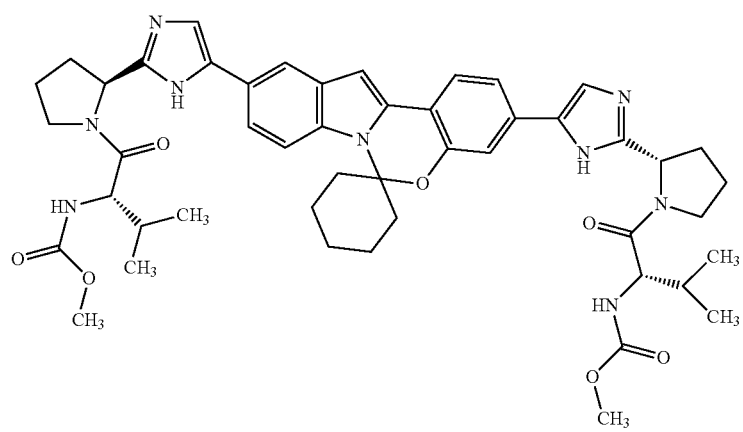
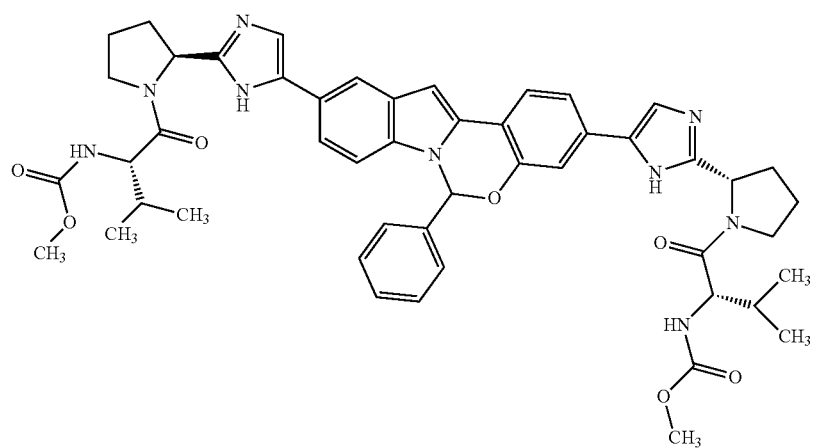

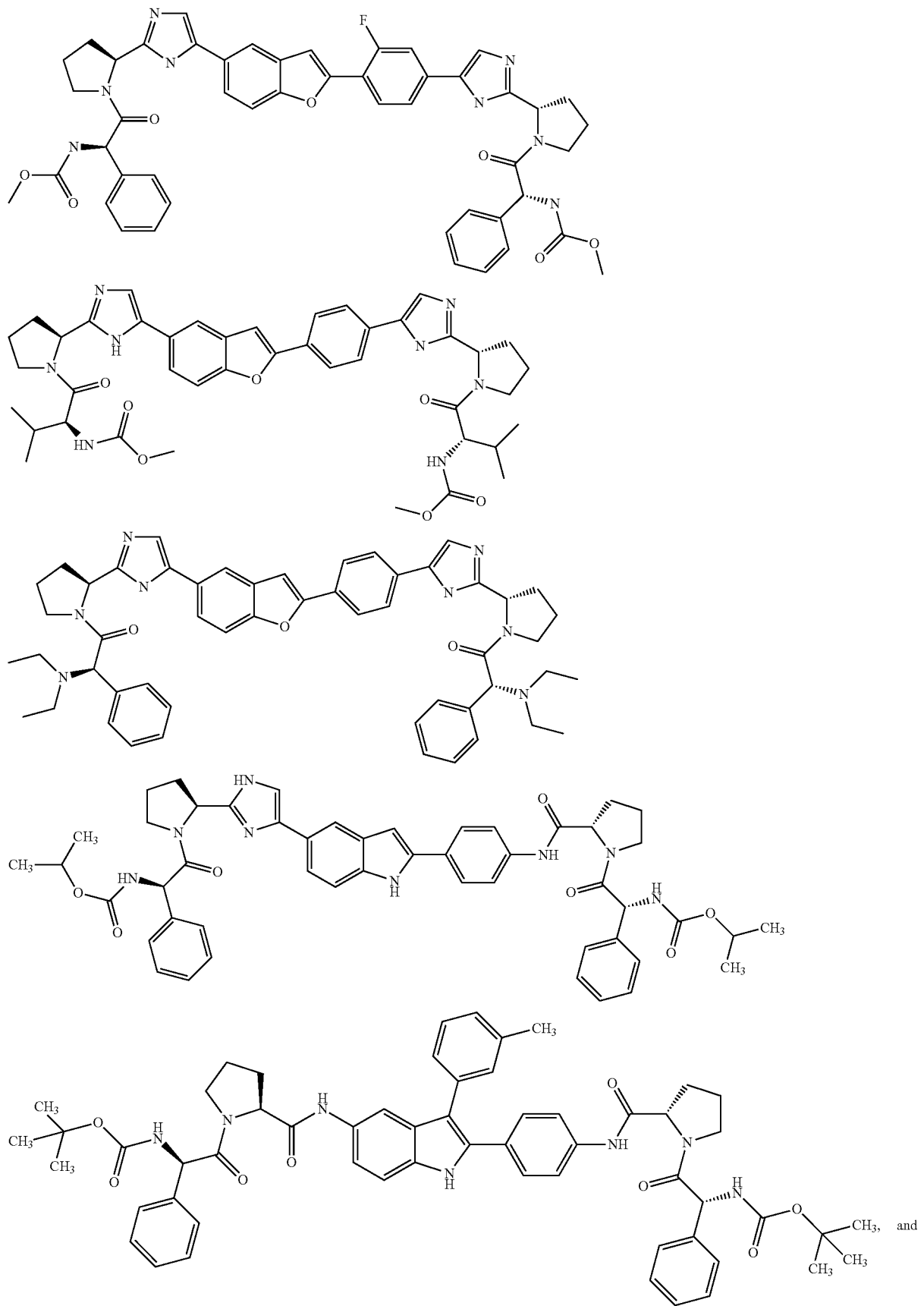

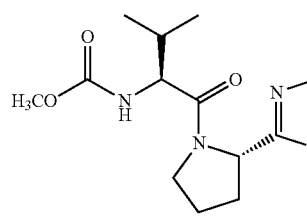 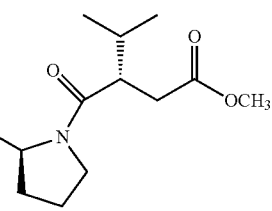

and pharmaceutically acceptable salts thereof.

HCV replicase inhibitors useful in the present compositions and methods include, but are not limited to, those disclosed in U.S. Patent Publication No. US20090081636.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). A compound of the invention and an additional therapeutic agent may be present in fixed amounts (dosage amounts) in a single dosage unit (e.g., a capsule, a tablet and the like).

The HCV NS5B inhibitory activity of the present compounds may be tested using assays known in the art. The HCV NS5B polymerase inhibitors described herein have activities in a genotype 1b replicon assay as described in the Examples. The assay is performed by incubating a replicon harboring cell-line in the presence of inhibitor for a set period of time and measuring the effect of the inhibitor on HCV replicon replication either directly by quantifying replicon RNA level, or indirectly by measuring enzymatic activity of a co-encoded reporter enzyme such as luciferase or β-lactamase. By performing a series of such measurements at different inhibitor concentrations, the effective inhibitory concentration of the inhibitor ($EC_{50}$ or $EC_{90}$) is determined. See Jan M. Vrolijk et al., *A replicons-based bioassay for the measurement of interferons in patients with chronic hepatitis C*, 110 J. VIROLOGICAL METHODS 201 (2003). Such assays may also be run in an automated format for high through-put screening. See Paul Zuck et al., *A cell-based β-lactamase reporter gene assay for the identification of inhibitors of hepatitis C virus replication*, 334 ANALYTICAL BIOCHEMISTRY 344 (2004).

The present invention also includes processes for making compounds of formula I. The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The following reaction schemes and examples serve only to illustrate the invention and its practice.

General Schemes

The compounds of Formula (I) may be prepared from known or readily prepared starting materials, following methods known to one skilled in the art of organic synthesis.

Methods useful for making the compounds of Formula (I) are set forth in the Examples below and generalized in Schemes 1-9 below. Alternative synthetic pathways and analogous structures will be apparent to those skilled in the art of organic synthesis. All stereoisomers and tautomeric forms of the compounds are contemplated.

Some commercially available starting materials and intermediates used for the synthesis of the compounds of Formula (I) are available. These starting materials and intermediates are available from commercial suppliers such as Sigma-Aldrich (St. Louis, Mo.) and Acros Organics Co. (Fair Lawn, N.J.). Such starting materials and intermediates compounds are used as received.

Scheme 1 shows methods useful for making useful intermediates I and K.

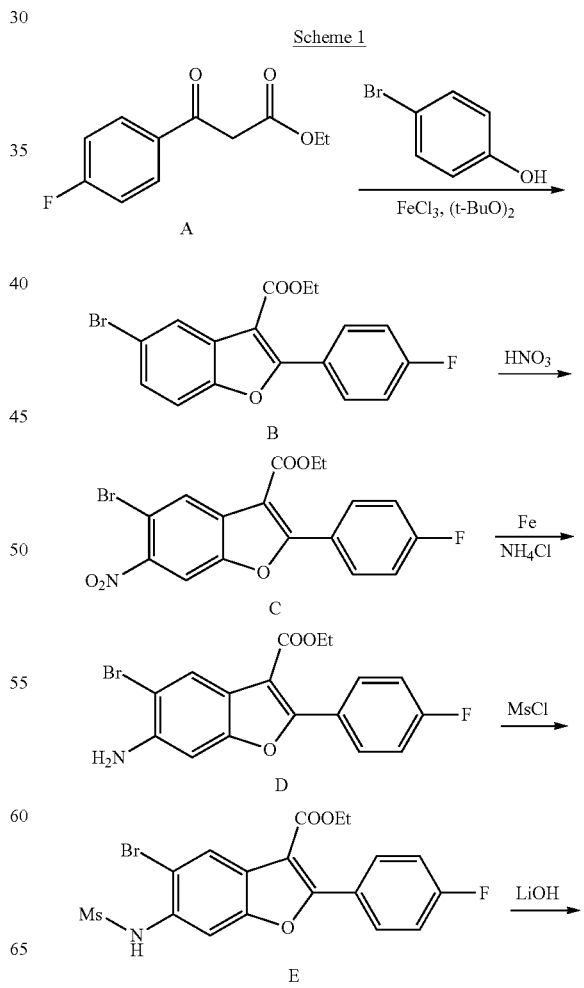

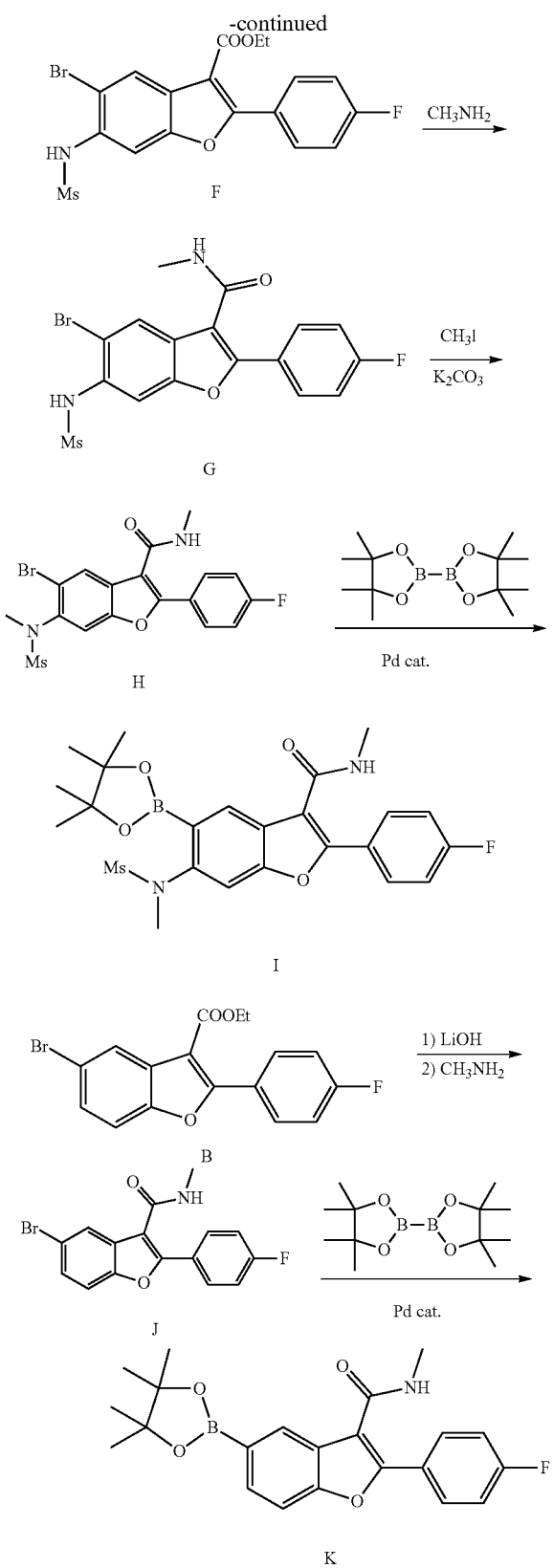
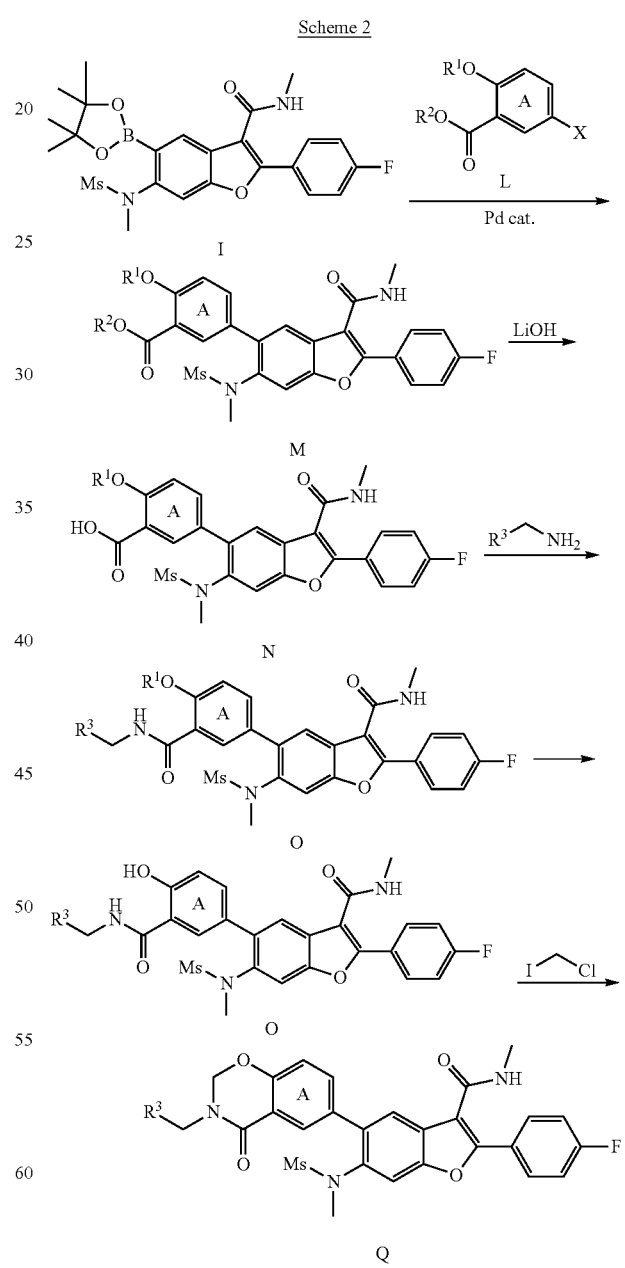

amino group of D provides compound E, which can then be hydrolyzed using LiOH, for example, to provide the carboxylic acid compound F. The carboxylic acid of compound F is then condensed with methanamine using common amide forming reagents such as EDCI and HOBT to provide compound G. The sulfonamide group of G can be coupled with MeI in the presence of potassium carbonate to provide compound H. Compound H can be converted to corresponding boronic ester I using bis(pinacolato)diboron in the presence of a palladium catalyst. Boronic ester K can be synthesized from compound B using similar procedures as well.

Scheme 2 shows an general method useful for making compounds of formula Q.

Commercially available compound A can be cyclized with 4-bromophenol to provide benzofuran compound B. Nitration of compound B provides nitrocompound C, which can be reduced to provide amine compound D. Mesylation of the Scheme 3 shows an alternate method useful for making compounds of formula Q.

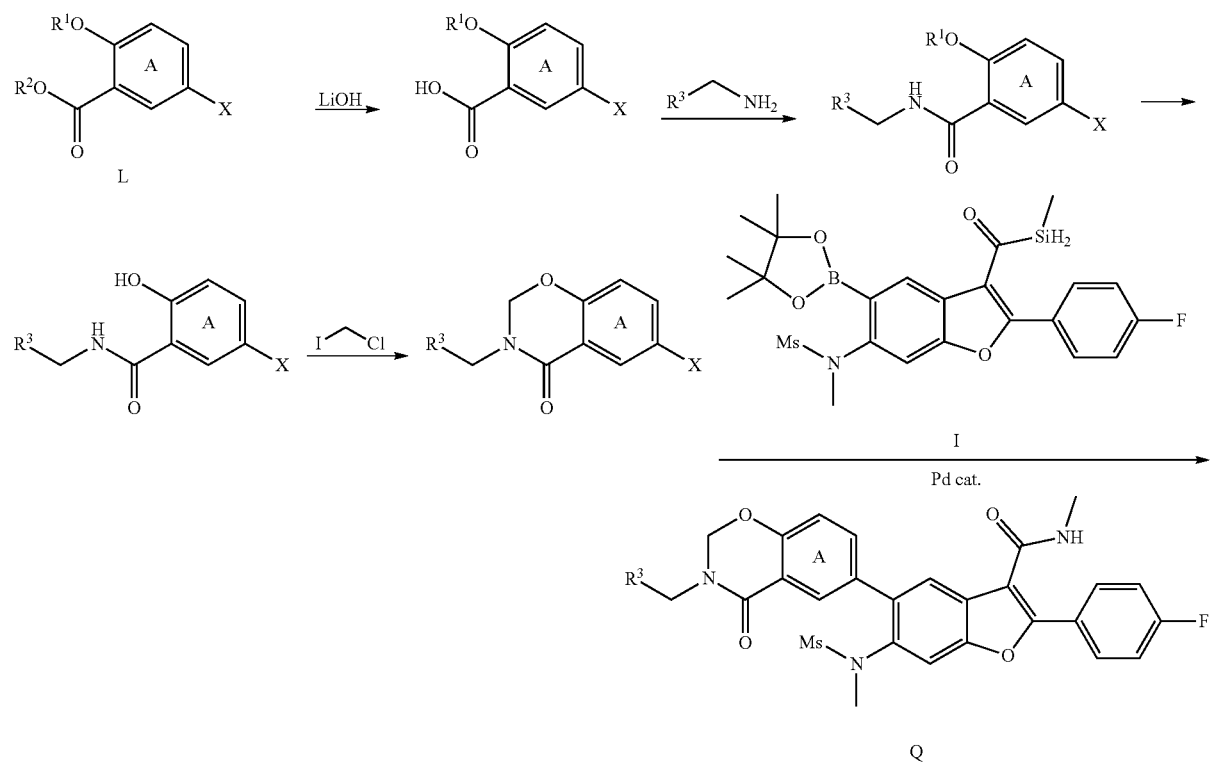
Scheme 4 shows an alternate method useful for making compounds of formula R.
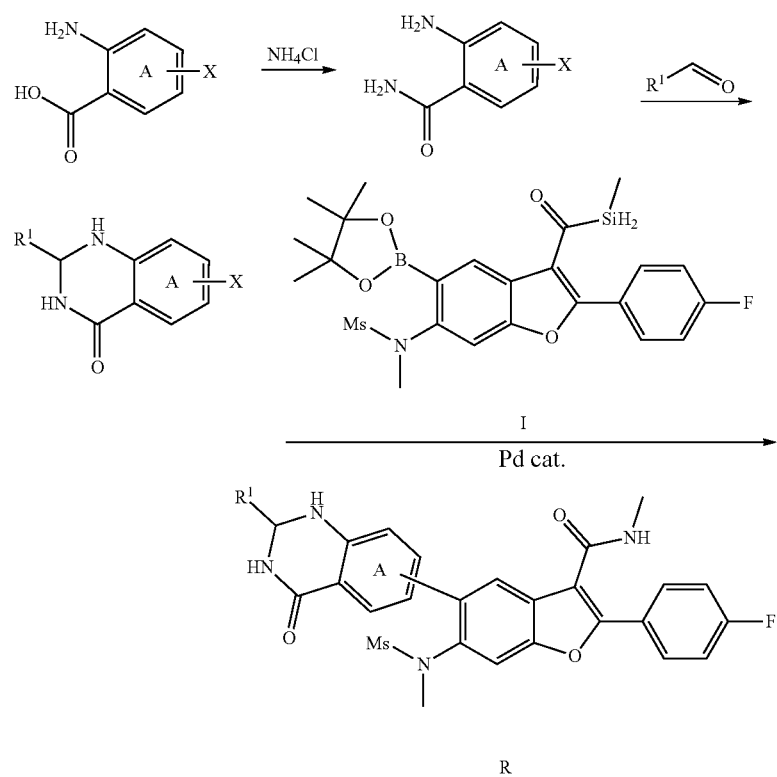

Scheme 5 shows an alternate method useful for making compounds of formula S.
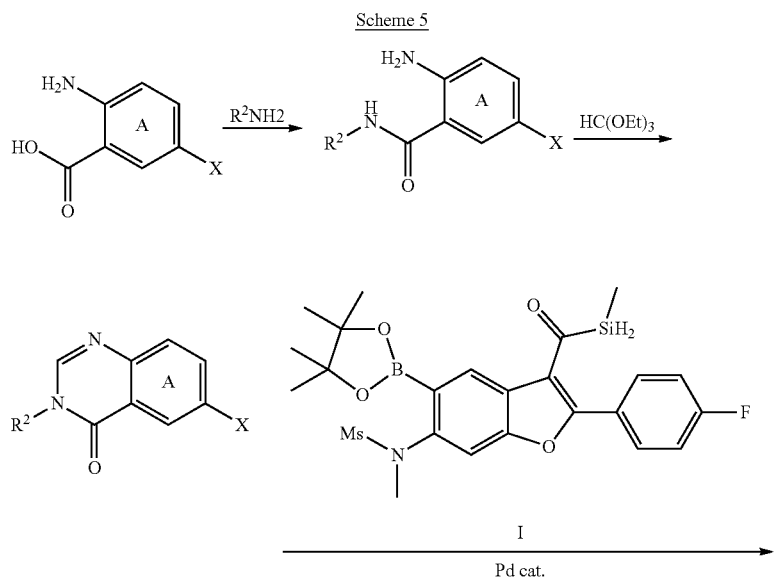
Scheme 6 shows an alternate method useful for making compounds of formula T.
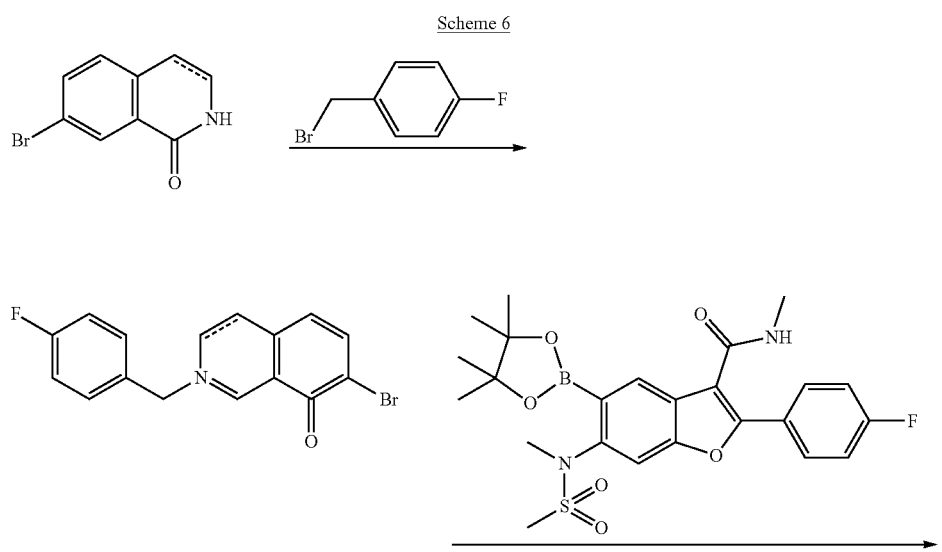

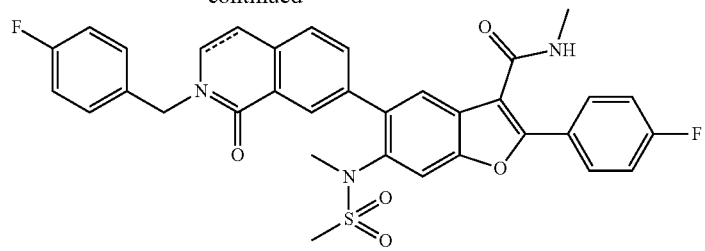
T
Scheme 7 shows an alternate method useful for making compounds of formula U.
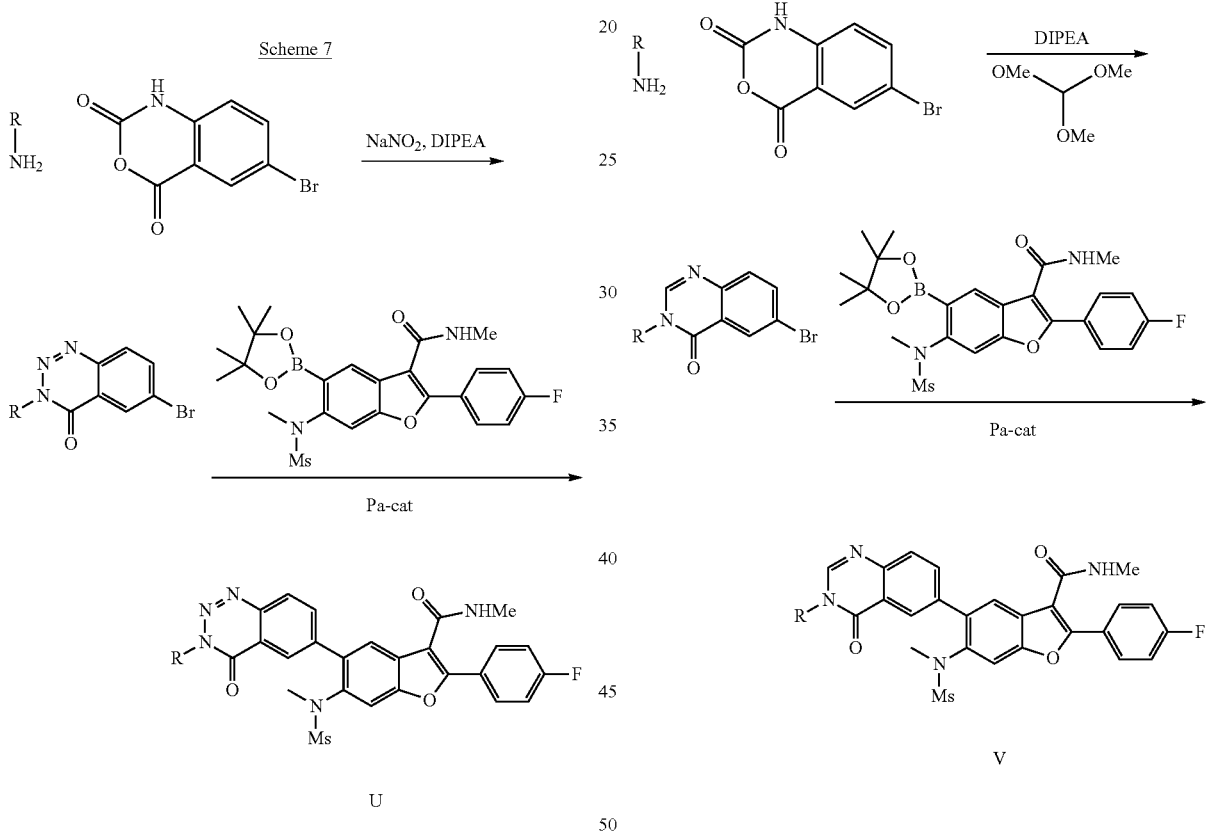
Scheme 8 shows an alternate method useful for making compounds of formula V.
Scheme 9 shows an alternate method useful for making compounds of formula W.
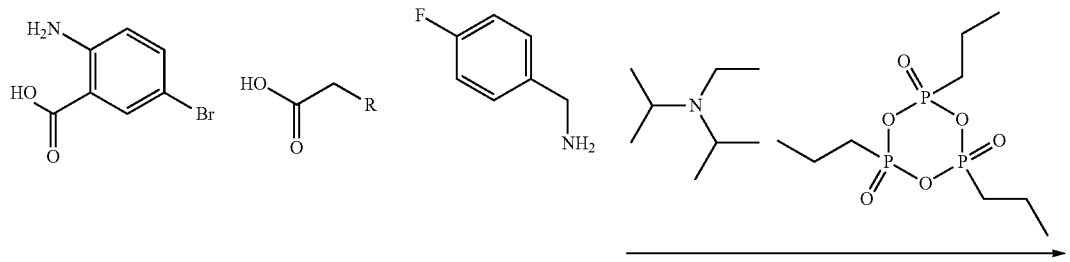

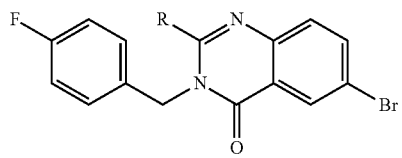
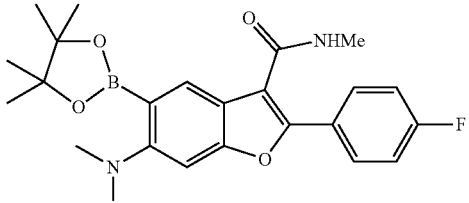
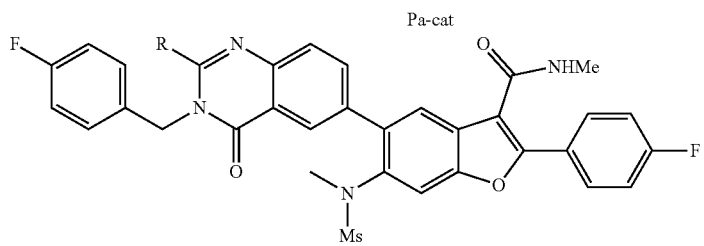

W

LIST OF ABBREVIATIONS

Ac₂O Acetic anhydride
AIBN 2-2'-Azoisobutyronitrile
a.q., aq Aqueous
Ar Argon
BBr₃ Boron tribromide
Boc t-butyloxycarbonyl
BnBr Boron nitride
n-BuLi n-Butyllithium
(t-BuO)₂ Di-tert-butyl peroxide
Br2 Bromine
cat. Catalyst
CCl₄ Carbon tetrachloride
CDCl₃ Deuterated chloroform
CO₂ Carbon dioxide
Cs₂CO₃ Cesium carbonate
DCM, CH₂Cl₂ Dichloromethane
DIEA, DIPEA N,N-Diisopropylethylamine
DMAc Dimethylacetamide
DMF Dimethylformamide
DMSO Dimethylsulfoxide
EDCI N-(3-Dimethylaminopropyl)-N'-ethylcarbodiimide (also EDC)
Et Ethyl
EtOAc, EA Ethyl acetate
EtOH Ethanol
Et₃N Triethylamine
Fe Iron
FeCl₃ Iron chloride
HATU O-(7-azabenzotriazol-1-yl)-N,N,N',N'-tetramethyluronium hexafluorophosphate
HC(OEt)₃ Triethyl orthoformate
HCHO Formaldehyde
HCl Hydrochloric acid
HNO₃ Nitric acid
H₂ Hydrogen
H₂O Water
HOBT 1-Hydroxy benzotriazole
HPLC High Performance Liquid Chromatography
K₂CO₃ Potassium carbonate
K₃PO₄ Potassium phosphate
LDA Lithium diisopropylamide
LiCl Lithium chloride
LiOH Lithium hydroxide
mCPBA Meta-chlorobenzoic acid
Me Methyl
MeCN Acetonitrile
MeNH₂, CH₃NH₂ Methanamine
MeI, CH₃I Methyl iodide
MeOH, CH₃OH Methanol
MS Mass spectroscopy
Ms Methanesulfonyl (or mesyl) group
MsCl Methanesulfonyl chloride
N₂ Nitrogen gas or atmosphere
NaHCO₃ Sodium bicarbonate
NaHSO₃ Sodium bisulfite
NaOH Sodium hydroxide
NaNO₂ Sodium nitrile
Na₂SO₄ Sodium sulfate (anhydrous)
NBS N-Bromosuccinimide
NH₄Cl Ammonium chloride
Pd Palladium
Pd₂(dba)₃ Tris(dibenzylideneacetone)dipalladium(0)
Pd(dppf)Cl₂ 1,1'-bis(diphenylphosphino)ferrocene-palladium(II)dichloride
Pd(OH)₂ Palladium hydroxide
POCl₃ Phosphoryl chloride
i-Pr₂NH Diisopropyl amine
PTSA p-toluenesulfonic acid
Py HCl Pyridine hydrochloride
RT Room temperature, approximately 25° C.
SOCl₂ Thionyl chloride
T3P Propylphosphonic Anhydride
THF Tetrahydrofuran
TLC Thin layer chromatography

EXAMPLES

Example 1

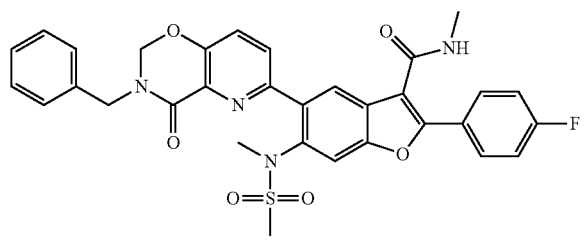 [SMILES: CNC(=O)c1c(-c2ccc(F)cc2)oc2cc(N(C)S(C)(=O)=O)c(-c3ccc4c(n3)C(=O)N(Cc3ccccc3)CO4)cc12]

Step 1—Synthesis of methyl 6-bromo-3-hydroxypicolinate

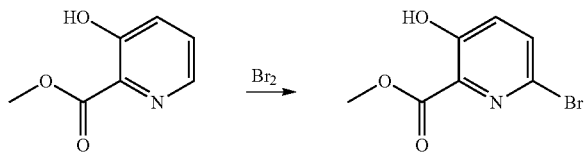

A mixture of methyl 3-hydroxypicolinate (5.0 g, 32.65 mmol) in H$_2$O was stirred at RT and then Br$_2$ (5.2 g, 32.65 mmol) was added dropwise. After the mixture was stirred at RT overnight, the mixture was filtered and the precipitate was washed with water and dried to give methyl 6-bromo-3-hydroxypicolinate (6.1 g, yield 80.7%). $^1$H-NMR (DMSO, 400 MHz) δ 10.71 (s, 1H), 7.69 (d, J=8.4 Hz, 1H), 7.41 (d, J=8.4 Hz, 1H), 3.87 (s, 3H). MS (M+H)$^+$: 232/234.

Step 2—Synthesis of methyl 3-(benzyloxy)-6-bromopicolinate

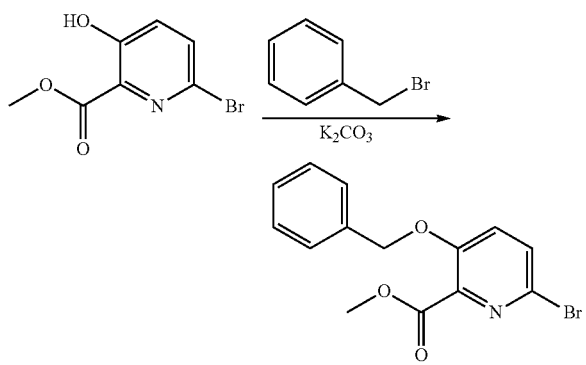

A mixture of methyl 6-bromo-3-hydroxypicolinate (500 mg, 2.15 mmol), BnBr (443 mg, 3.25 mmol) and K$_2$CO$_3$ (595 mg, 4.31 mmol) in THF (5 mL) was stirred at RT for 3 h. Then water was added and the mixture was extracted with EtOAc (20 mL*3). The organic layer was dried over Na$_2$SO$_4$ and concentrated to give crude methyl 3-(benzyloxy)-6-bromopicolinate (500 mg, yield 72%), which was used for the next step without further purification. MS (M+H)$^+$: 322/324.

Step 3—Synthesis of 3-(benzyloxy)-6-bromopicolinic acid

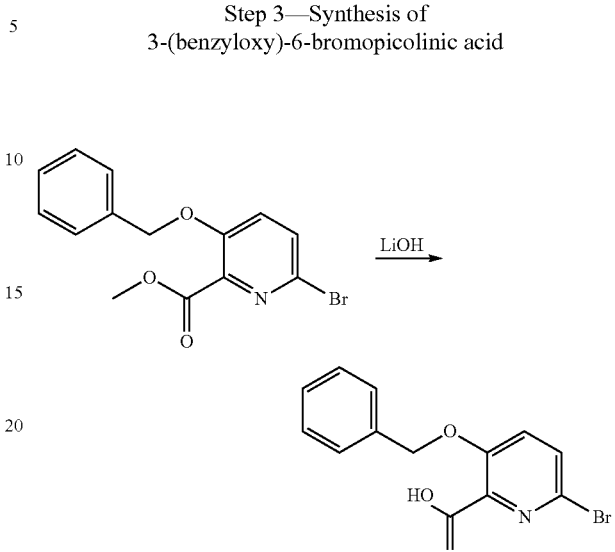

A solution of methyl 3-(benzyloxy)-6-bromopicolinate (2.0 g, 6.20 mmol) and LiOH.H$_2$O (0.71 g, 18.60 mmol) in 1,4-dioxane/H$_2$O (100 mL/20 mL) was stirred at 40° C. overnight. The mixture was filtered and the filtrate was acidified to pH=3 by aqueous HCl (2 M) and extracted with EtOAc. The combined organic phase was washed with brine, dried over Na$_2$SO$_4$ and concentrated to afford the product of 3-(benzyloxy)-6-bromopicolinic acid (1.87 g, yield: 97.9%) without further purification. $^1$H-NMR (CDCl$_3$, 400 MHz) δ 7.52~7.54 (m, 1H), 7.39~7.41 (m, 2H), 7.24~7.34 (m, 4H), 5.24 (s, 2H). MS (M+H)$^+$: 308/310.

Step 4—Synthesis of N-benzyl-3-(benzyloxy)-6-bromopicolinamide

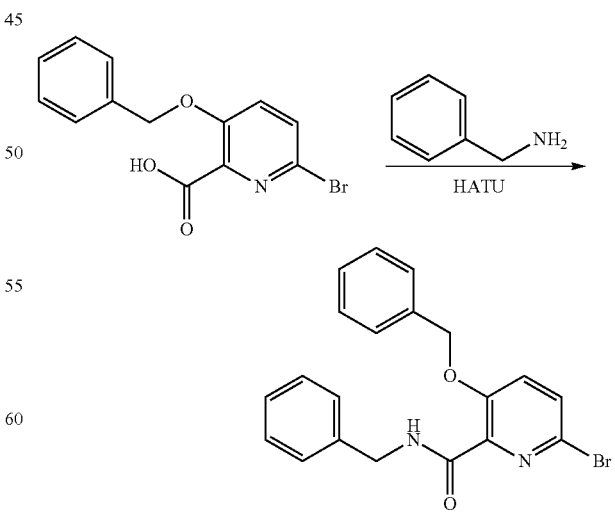

To a solution of 3-(benzyloxy)-6-bromopicolinic acid (0.50 g, 1.62 mmol) and HATU (1.23 g, 3.24 mmol) in DMF (5 mL) was added phenylamine (0.52 g, 4.87 mmol) dropwise. After stirring at room temperature overnight, the mixture was concentrated and the residue was diluted with water and extracted with EtOAc. The combined organic phase was washed with brine, dried over Na₂SO₄ and concentrated. The residue was purified by flash gel chromatography (DCM: MeOH=50:1) to afford the product of N-benzyl-3-(benzyloxy)-6-bromopicolinamide (0.60 g, yield: 93.2%). ¹H-NMR (CDCl₃, 400 MHz) δ 7.79 (br s, 1H), 7.38~7.41 (m, 3H), 7.19~7.32 (m, 9H), 5.18 (s, 2H), 4.58 (d, J=5.6 Hz, 2H). MS (M+H)⁺: 397/399.

Step 5—Synthesis of N-benzyl-3-(benzyloxy)-6-(2-(4-fluorophenyl)-3-(methylcarbamoyl)-6-(N-methylmethylsulfonamido)benzofuran-5-yl)picolinamide

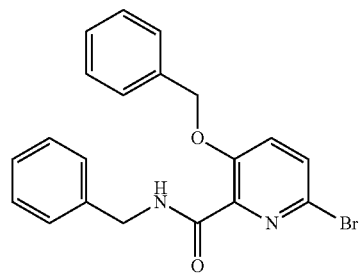

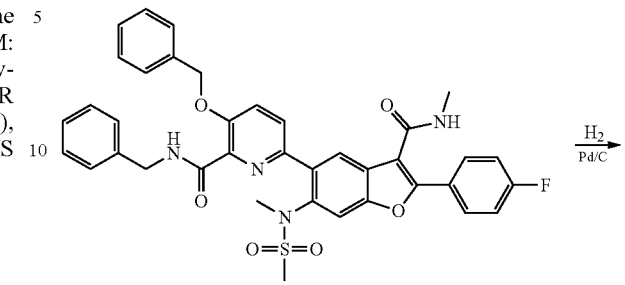

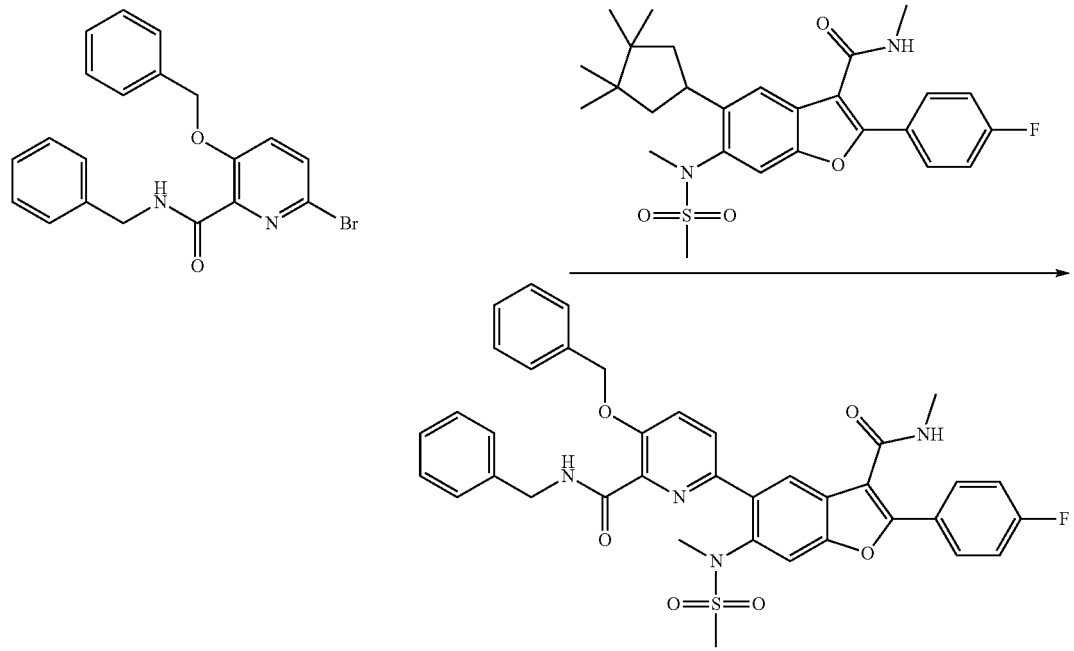

To a solution of N-benzyl-3-(benzyloxy)-6-bromopicolinamide (107 mg, 0.27 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (prepared according to previous patents, 117 mg, 0.23 mmol) and K₃PO₄·3H₂O (187 mg, 0.70 mmol) in dioxane/H₂O (3 mL) were added Pd₂(dba)₃ (11 mg, 0.01 mmol) and X-Phos (11 mg, 0.03 mmol) under N₂. The mixture was stirred at 110° C. for 1 hour. Then it was filtered and extracted with EtOAc. The combined organic phase was washed with brine, dried over Na₂SO₄ and concentrated. The residue was purified by prep-TLC (DCM:MeOH=50:1) to afford the product of N-benzyl-3-(benzyloxy)-6-(2-(4-fluorophenyl)-3-(methylcarbamoyl)-6-(N-methylmethylsulfonamido)benzofuran-5-yl) picolinamide (100 mg, yield: 61.7%). ¹H-NMR (CD₃OD, 400 MHz) δ 7.91~7.94 (m, 2H), 7.83 (s, 1H), 7.77 (s, 1H), 7.67~7.72 (m, 2H), 7.43~7.45 (m, 2H), 7.29~7.33 (m, 5H), 7.20~7.24 (m, 5H), 5.23 (s, 2H), 4.54 (s, 2H), 3.15 (s, 3H), 2.89 (s, 3H), 2.87 (s, 3H). MS (M+H)⁺: 693.

Step 6—Synthesis of N-benzyl-6-(2-(4-fluorophenyl)-3-(methylcarbamoyl)-6-(N-methylmethylsulfonamido)benzofuran-5-yl)-3-hydroxypicolinamide -continued

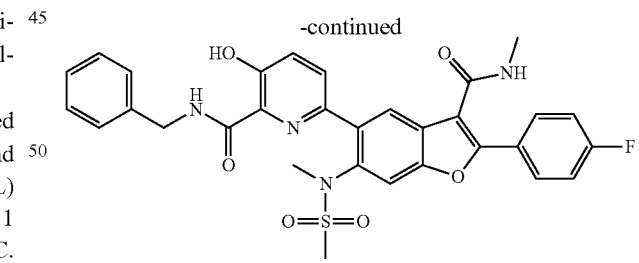

A mixture of N-benzyl-3-(benzyloxy)-6-(2-(4-fluorophenyl)-3-(methylcarbamoyl)-6-(N-methylmethylsulfonamido) benzofuran-5-yl)picolinamide (200 mg, 0.29 mmol) and Pd/C (10 mg) in CH₃OH (10 mL) was stirred at room temperature overnight under H₂ atmosphere (50 psi). The mixture was filtered and the filtrate was concentrated in vacuum. The residue was purified by prep-TLC (DCM:EtOAc=5:1) to give the product of N-benzyl-6-(2-(4-fluorophenyl)-3-(methylcarbamoyl)-6-(N-methylmethylsulfonamido)benzofuran-5-yl)-3-hydroxypicolinamide (125 mg, yield: 71.8%). ¹H-NMR (CDCl₃, 400 MHz) δ 8.73 (br s, 1H), 7.84~7.87 (m, 3H), 7.63 (d, J=8.4 Hz, 1H), 7.49 (s, 1H), 7.44 (d, J=8.4 Hz, 1H), 7.30~7.36 (m, 4H), 7.26 (d, J=6.0 Hz, 1H), 7.19 (t, J=8.0 Hz, 2H), 6.39 (br s, 1H), 4.60 (d, J=4.8 Hz, 2H), 3.04 (s, 3H), 2.93 (d, J=3.2 Hz, 3H), 2.87 (s, 3H). MS (M+H)+: 603.

Step 7—Synthesis of 5-(3-benzyl-4-oxo-3,4-dihydro-2H-pyrido[2,3-e][1,3]oxazin-6-yl)-2-(4-fluorophenyl)-N-methyl-6-(N-methylmethylsulfonamido)benzofuran-3-carboxamide

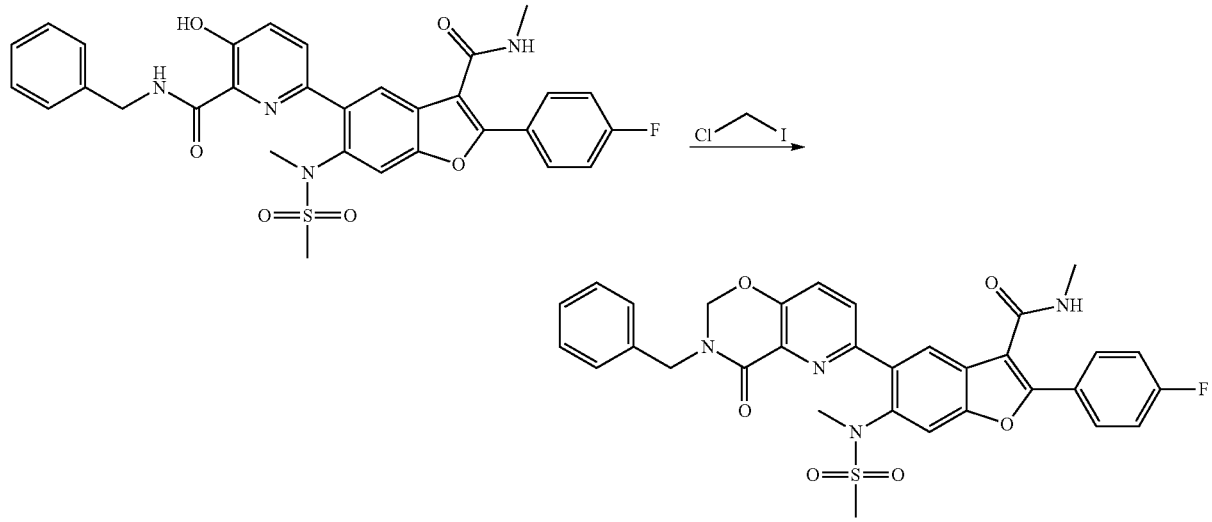

To a solution of N-benzyl-6-(2-(4-fluorophenyl)-3-(methylcarbamoyl)-6-(N-methylmethylsulfonamido)benzofuran-5-yl)-3-hydroxypicolinamide (100 mg, 0.17 mmol) and $Cs_2CO_3$ (117 mg, 0.33 mmol) in DMF (20 mL) was added chloroiodomethane (47 mg, 0.25 mmol) dropwise at 110° C. under $N_2$. The mixture was stirred at 110° C. for 0.5 hour. Then the mixture was concentrated and extracted with EtOAc. The combined organic phase was washed with brine, dried over $Na_2SO_4$ and concentrated. The residue was purified by prep-TLC (DCM:$CH_3OH$=20:1) to afford the product of 5-(3-benzyl-4-oxo-3,4-dihydro-2H-pyrido[2,3-e][1,3]oxazin-6-yl)-2-(4-fluorophenyl)-N-methyl-6-(N-methylmethylsulfonamido)benzofuran-3-carboxamide (20 mg, yield: 19.6%). 1H-NMR (CDCl3, 400 MHz) δ 7.88~7.90 (m, 3H), 7.72~7.74 (m, 1H), 7.55 (s, 1H), 7.34~7.39 (m, 5H), 7.25~7.28 (m, 1H), 7.14 (t, J=7.2 Hz, 2H), 6.87 (br s, 1H), 5.19 (s, 2H), 4.76 (s, 2H), 3.14 (s, 3H), 2.93~2.94 (m, 6H). MS (M+H)+: 615.

Examples 2~5, depicted in the table below, were prepared using the method described above.

| Example | Structure | NMR | MS (M + H)+ |
|---|---|---|---|
| 2 | 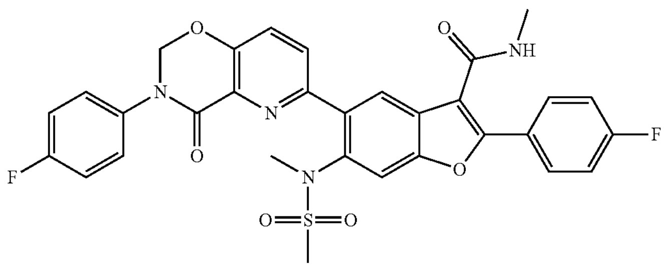 [SMILES: CNC(=O)c1c(-c2ccc(F)cc2)oc2cc(N(C)S(C)(=O)=O)c(-c3ccc4c(n3)C(=O)N(c3ccc(F)cc3)CO4)cc12] | 1H-NMR (CDCl3, 400 MHz) δ 7.96~8.01 (m, 3H), 7.83 (d, J = 8.0 Hz, 1H), 7.65 (s, 1H), 7.56 (d, J = 8.0 Hz, 1H), 7.37~7.39 (m, 2H), 7.13~7.22 (m, 4H), 6.13 (d, J = 4.0 Hz, 1H), 5.65 (s, 2H), 3.02 (s, 3H), 2.99 (d, J = 4.8 Hz, 3H), 2.93 (s, 3H). | 619 |
| 3 | 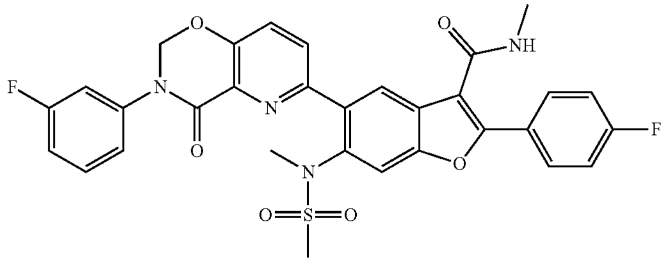 [SMILES: CNC(=O)c1c(-c2ccc(F)cc2)oc2cc(N(C)S(C)(=O)=O)c(-c3ccc4c(n3)C(=O)N(c3cccc(F)c3)CO4)cc12] | 1H-NMR (CDCl3, 400 MHz) δ 7.99~8.04 (m, 3H), 7.87 (d, J = 8.0 Hz, 1H), 7.64 (s, 1H), 7.57 (d, J = 8.0 Hz, 1H), 7.40~7.46 (m, 1H), 7.17~7.22 (m, 4H), 7.02~7.06 (m, 1H), 6.36 (d, J = 4.0 Hz, 1H), 5.67 (s, 2H), 3.26 (s, 3H), 3.00 (d, J = 4.8 Hz, 3H), 2.94 (s, 3H). | 619 |

| Example | Structure | NMR | MS (M+H)+ |
|---|---|---|---|
| 4 | 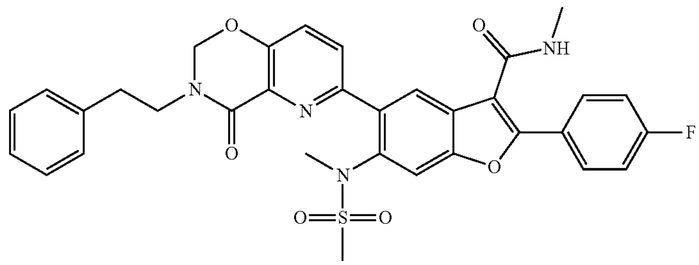 [SMILES: CNC(=O)c1c(-c2ccc(F)cc2)oc2cc(N(C)S(C)(=O)=O)c(-c3ccc4c(n3)C(=O)N(CCc3ccccc3)CO4)cc12] | ¹H-NMR (CDCl₃, 400 MHz) δ 7.97~8.02 (m, 3H), 7.73 (d, J = 8.4 Hz, 1H), 7.62 (s, 1H), 7.40 (d, J = 8.4 Hz, 1H), 7.30~7.34 (m, 3H), 7.17~7.25 (m, 4H), 6.33 (br s, 1H), 4.96 (s, 2H), 3.86 (t, J = 7.2 Hz, 2H), 3.22 (s, 3H), 2.98~3.02 (m, 5H), 2.90 (s, 3H). | 629 |
| 5 | 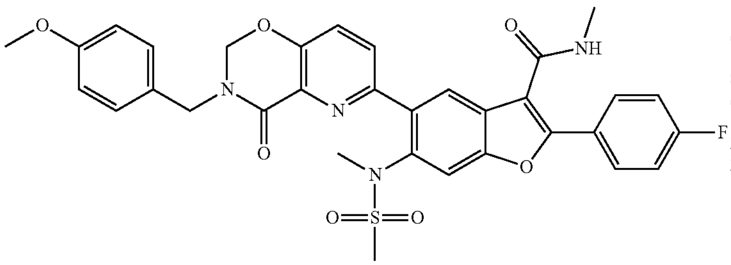 [SMILES: CNC(=O)c1c(-c2ccc(F)cc2)oc2cc(N(C)S(C)(=O)=O)c(-c3ccc4c(n3)C(=O)N(Cc3ccc(OC)cc3)CO4)cc12] | ¹H-NMR (CDCl₃, 400 MHz) δ 7.95~8.02 (m, 3H), 7.70 (d, J = 8.4 Hz, 1H), 7.56 (s, 1H), 7.36 (d, J = 8.4 Hz, 1H), 7.23 (d, J = 8.8 Hz, 2H), 7.12 (t, J = 8.8 Hz, 2H), 6.82 (d, J = 8.8 Hz, 2H), 6.24 (d, J = 8.8 Hz, 1H), 5.14 (s, 2H), 4.69 (s, 2H), 3.74 (s, 3H), 3.14 (s, 3H), 2.93 (d, J = 4.8 Hz, 3H), 2.87 (s, 3H). | 645 |

Example 6

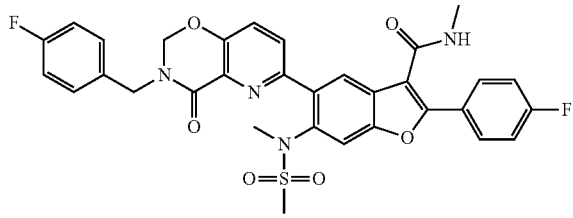 [SMILES: CNC(=O)c1c(-c2ccc(F)cc2)oc2cc(N(C)S(C)(=O)=O)c(-c3ccc4c(n3)C(=O)N(Cc3ccc(F)cc3)CO4)cc12]

Step 1—Synthesis of 3-(benzyloxy)-6-bromo-N-(4-fluorobenzyl)picolinamide

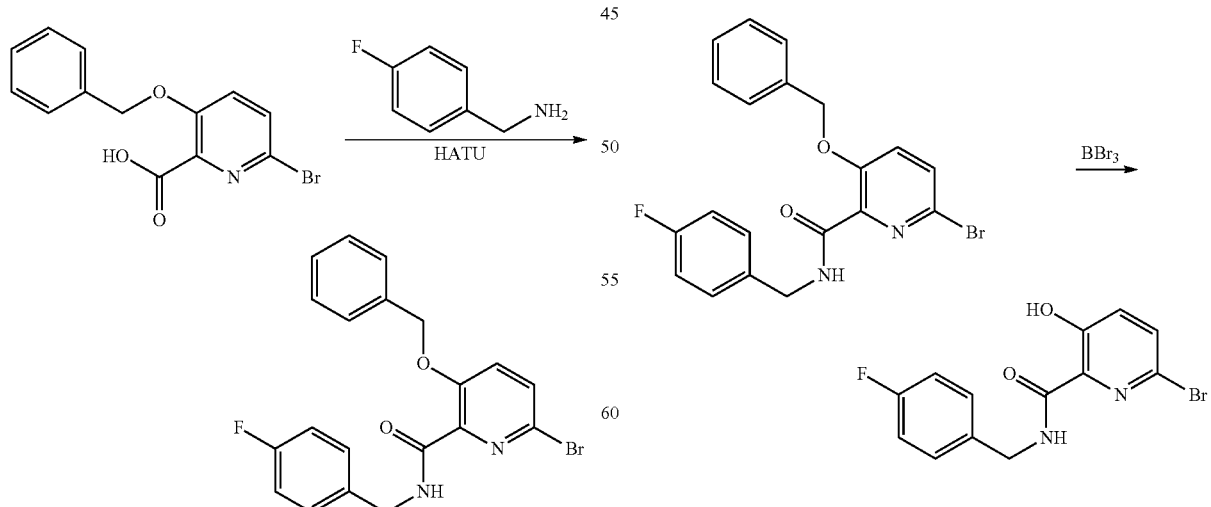

To a solution of 3-(benzyloxy)-6-bromopicolinic acid (1.90 g, 6.2 mmol), HATU (4.69 g, 12.4 mmol) and Et₃N (0.5 mL) in DMF (20 mL) was added 4-fluorobenzylamine (2.30 g, 18.5 mmol) dropwise. The mixture was stirred at room temperature overnight. Then it was concentrated and extracted with EtOAc. The combined organic phase was washed with brine, dried over Na₂SO₄ and concentrated. The residue was purified by flash gel chromatography (PE:EtOAc=2:1) to afford the product of 3-(benzyloxy)-6-bromo-N-(4-fluorobenzyl)picolinamide (2 g, yield: 77.8%). ¹H-NMR (CDCl₃, 400 MHz) δ 7.84 (s, 1H), 7.42~7.45 (m, 3H), 7.23~7.37 (m, 6H), 6.97 (t, J=8.8 Hz, 2H), 5.21 (s, 2H), 4.57 (d, J=6.0 Hz, 2H). MS (M+H)⁺: 415/417.

Step 2—Synthesis of 6-bromo-N-(4-fluorobenzyl)-3-hydroxypicolinamide

To a solution of 3-(benzyloxy)-6-bromo-N-(4-fluorobenzyl)picolinamide (50 mg, 0.11 mmol) in CH₂Cl₂ (5 mL) was added BBr₃ (1.5 mL) dropwise at −78° C. under N₂. The mixture was allowed to room temperature and stirred for another 12 hours. Then CH₃OH was added and the mixture was adjusted to pH=7 by saturated K₂CO₃. The mixture was extracted with EtOAc and the combined organic phase was washed with brine, dried over Na₂SO₄ and concentrated. The residue was purified by prep-TLC (PE:EtOAc=5:1) to afford the product of 6-bromo-N-(4-fluorobenzyl)-3-hydroxypicolinamide (20 mg, yield: 57%). ¹H-NMR (CDCl₃, 400 MHz) δ 12.04 (s, 1H), 8.02 (s, 1H), 7.39 (d, J=8.8 Hz, 1H), 7.24~7.28 (m, 2H), 7.15 (d, J=8.8 Hz, 1H), 6.96~7.00 (m, 2H), 4.52 (d, J=6.4 Hz, 2H). MS (M+H)⁺: 325/327.

Step 3—Synthesis of 6-bromo-3-(4-fluorobenzyl)-2H-pyrido[2,3-e][1,3]oxazin-4(3H)-one

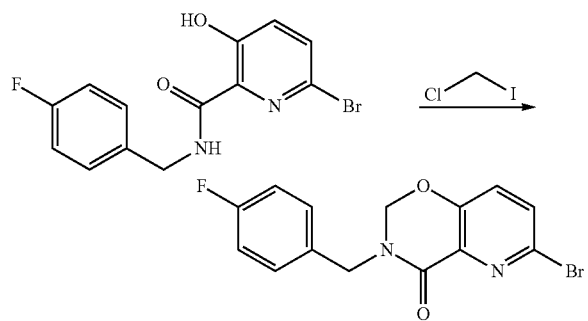

To a solution of 6-bromo-N-(4-fluorobenzyl)-3-hydroxypicolinamide (100 mg, 0.31 mmol) and Cs₂CO₃ (219 mg, 0.62 mmol) in DMF (10 mL) was added chloroiodomethane (87 mg, 0.46 mmol) dropwise at 110° C. under N₂. The mixture was stirred at 110° C. for 0.5 hour. Then the mixture was concentrated and extracted with EtOAc. The combined organic phase was washed with brine, dried over Na₂SO₄ and concentrated. The residue was purified by prep-TLC (PE:EtOAc=2:1) to afford the product of 6-bromo-3-(4-fluorobenzyl)-2H-pyrido[2,3-e][1,3]oxazin-4(3H)-one (70 mg, yield: 67.3%). ¹H-NMR (CDCl₃, 400 MHz) δ 7.46~7.48 (m, 1H), 7.26~7.29 (m, 2H), 7.18~7.20 (m, 1H), 6.96 (t, J=8.4 Hz, 2H), 5.16 (s, 2H), 4.70 (s, 2H). MS (M+H)⁺: 337/339.

Step 4—Synthesis of 5-(3-(4-fluorobenzyl)-4-oxo-3,4-dihydro-2H-pyrido[2,3-e][1,3]oxazin-6-yl)-2-(4-fluorophenyl)-N-methyl-6-(N-methylmethylsulfonamido)benzofuran-3-carboxamide

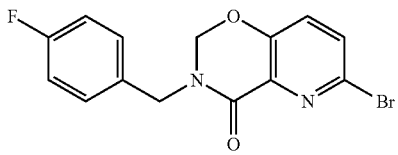 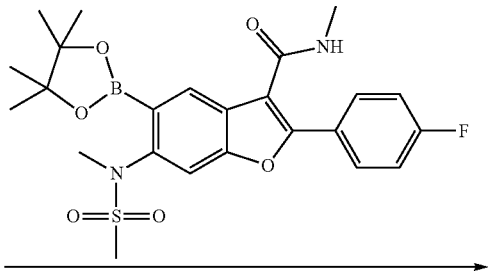

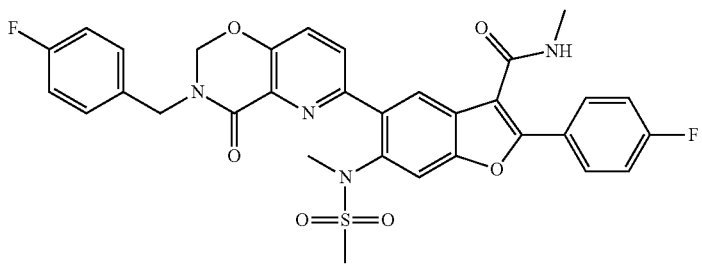

To a solution of 6-bromo-3-(4-fluorobenzyl)-2H-pyrido[2,3-e][1,3]oxazin-4(3H)-one (110 mg, 0.33 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (149 mg, 0.30 mmol) and K₃PO₄·3H₂O (237 mg, 0.89 mmol) in dioxane/H₂O (5 mL/0.2 mL) were added Pd₂(dba)₃ (13 mg, 0.02 mmol) and X-phos (14 mg, 0.03 mmol) under N₂. The mixture was stirred at 110° C. for 1 hour. Then it was filtered and extracted with EtOAc. The combined organic phase was washed with brine, dried over Na₂SO₄ and concentrated. The residue was purified by flash gel chromatography (DCM:MeOH=100:1) to afford the product of 5-(3-(4-fluorobenzyl)-4-oxo-3,4-dihydro-2H-pyrido[2,3-e][1,3]oxazin-6-yl)-2-(4-fluorophenyl)-N-methyl-6-(N-methylmethylsulfonamido)benzofuran-3-carboxamide (170 mg, yield: 82%). ¹H-NMR (CDCl₃, 400 MHz) δ 7.94~7.97 (m, 3H), 7.75~7.77 (m, 1H), 7.62 (s, 1H), 7.42~7.45 (m, 1H), 7.33~7.36 (m, 2H), 7.19 (t, J=7.6 Hz, 2H), 7.05 (t, J=7.6 Hz, 2H), 6.05 (br s, 1H), 5.22 (s, 2H), 4.78 (s, 2H), 3.22 (s, 3H), 2.99 (d, J=4.8 Hz, 3H), 2.93 (s, 3H). MS (M+H)⁺: 633.

Examples 7-9, depicted in the table below, were prepared using the method described above.

| Example | Structure | NMR | MS (M+H)+ |
|---|---|---|---|
| 7 | 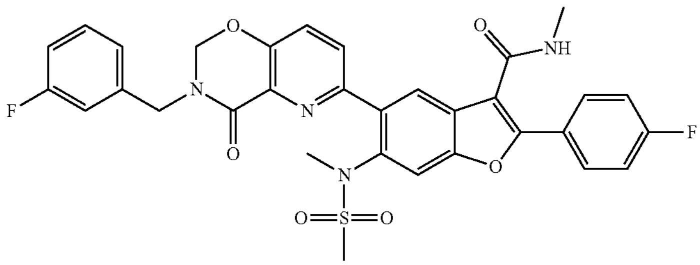 [SMILES: CNC(=O)c1c(-c2ccc(F)cc2)oc2cc(N(C)S(C)(=O)=O)c(-c3ccc4c(n3)C(=O)N(Cc3cccc(F)c3)CO4)cc12] | $^1$H-NMR (CDCl$_3$, 400 MHz) δ 7.85~7.89 (m, 3H), 7.71~7.73 (m, 1H), 7.53~7.54 (m, 1H), 7.36~7.39 (m, 1H), 7.24~7.31 (m, 1H), 7.10~7.14 (m, 3H), 7.04 (d, J = 9.6 Hz, 1H), 6.98 (t, J = 9.6 Hz, 1H), 6.67 (br s, 1H), 5.20 (s, 2H), 4.73 (s, 2H), 3.12 (s, 3H), 2.92~2.94 (m, 6H). | 633 |
| 8 | 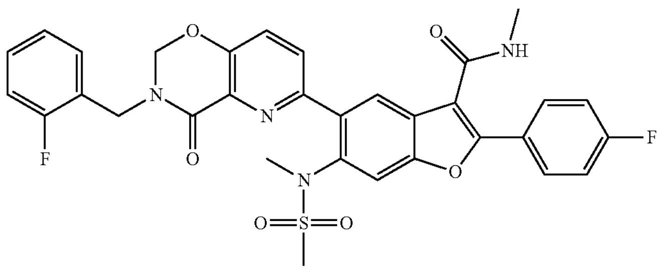 [SMILES: CNC(=O)c1c(-c2ccc(F)cc2)oc2cc(N(C)S(C)(=O)=O)c(-c3ccc4c(n3)C(=O)N(Cc3ccccc3F)CO4)cc12] | $^1$H-NMR (CDCl$_3$, 400 MHz) δ 7.92~7.96 (m, 3H), 7.75 (d, J = 8.8 Hz, 1H), 7.59 (s, 1H), 7.49~7.52 (m, 1H), 7.42 (d, J = 8.4 Hz, 1H), 7.26~7.33 (m, 1H), 7.07~7.19 (m, 4H), 6.43 (br s, 1H), 5.32 (s, 2H), 4.83 (s, 2H), 3.18 (s, 3H), 2.98 (d, J = 4.8 Hz, 3H), 2.92 (s, 3H). | 633 |
| 9 | 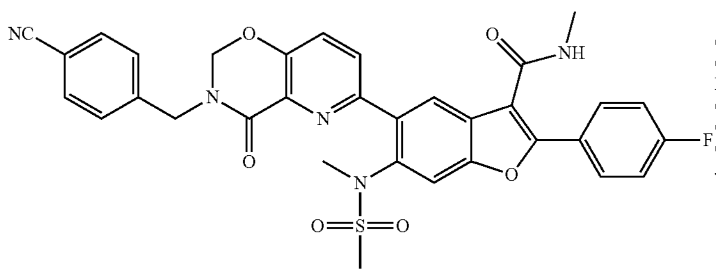 | $^1$H-NMR (CDCl$_3$, 400 MHz) δ 7.99 (s, 1H), 7.93~7.98 (m, 2H), 7.80 (d, J = 8.8 Hz, 1H), 7.67 (d, J = 8.4 Hz, 2H), 7.61 (s, 1H), 7.43~7.52 (m, 3H), 7.19 (t, J = 8.4 Hz, 2H), 6.19 (br s, 1H), 5.27 (s, 2H), 4.87 (s, 2H), 3.23 (s, 3H), 2.99 (d, J = 4.8 Hz, 3H), 2.95 (s, 3H). | 640 |

Example 10

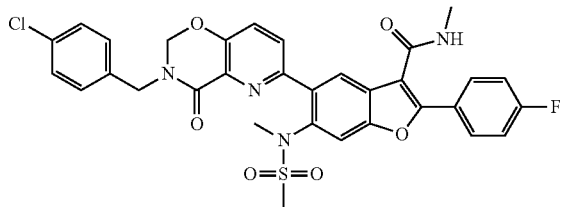 [SMILES: CNC(=O)c1c(-c2ccc(F)cc2)oc2cc(N(C)S(C)(=O)=O)c(-c3ccc4c(n3)C(=O)N(Cc3ccc(Cl)cc3)CO4)cc12]

Step 1—Synthesis of methyl 6-bromo-3-methoxypicolinate

A mixture of methyl 6-bromo-3-hydroxypicolinate (10.0 g, 43.10 mmol), MeI (12.3 g, 86.66 mmol) and K$_2$CO$_3$ (12.0 g, 86.83 mmol) in DMF (100 mL) was stirred at RT overnight. Then the reaction mixture was concentrated, diluted with water and extracted with EtOAc. The organic layer was dried over Na$_2$SO$_4$ and concentrated to give methyl 6-bromo-3-methoxypicolinate (4.5 g, yield 42%). $^1$H-NMR (CDCl$_3$, 400 MHz) δ 7.55 (d, J=8.8 Hz, 1H), 7.24 (d, J=8.8 Hz, 1H), 3.94 (s, 3H), 3.90 (s, 3H). MS (M+H)$^+$: 246/248.

Step 2—Synthesis of 6-bromo-3-methoxypicolinic acid

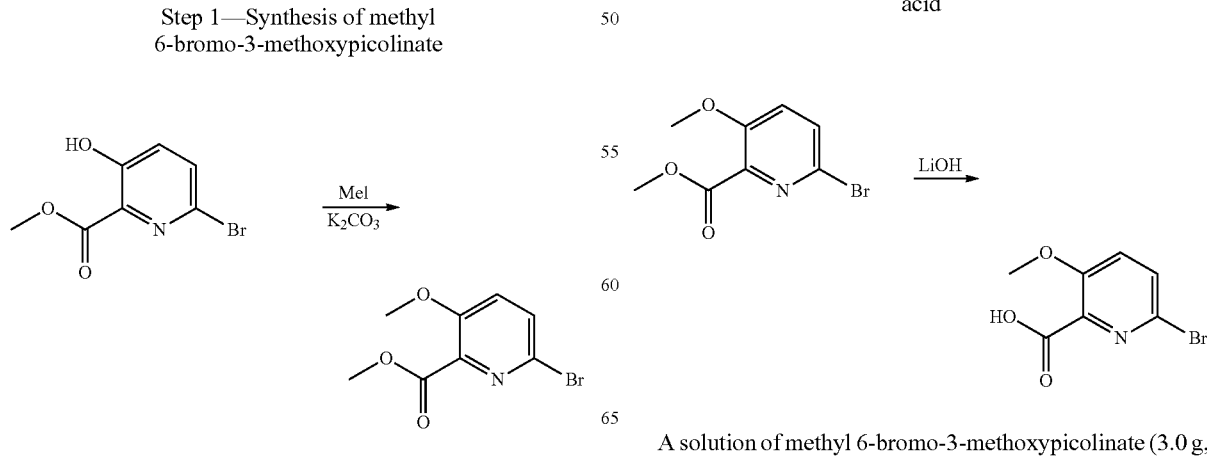

A solution of methyl 6-bromo-3-methoxypicolinate (3.0 g, 12.19 mmol) and LiOH.H$_2$O (1.4 g, 33.36 mmol) in 1,4- dioxane/H$_2$O (15 mL/15 mL) was stirred at RT overnight. The mixture was filtered and the filtrate was adjusted to pH=3 by aqueous HCl (2 M) and extracted with EtOAc. The combined organic phase was washed with brine, dried over Na$_2$SO$_4$ and concentrated to give the crude product of 6-bromo-3-methoxypicolinic acid (2.1 g, yield: 73%) without further purification. $^1$H-NMR (CDCl$_3$, 400 MHz) δ 10.05 (br s, 1H), 7.70 (d, J=8.8 Hz, 1H), 7.40 (d, J=8.8 Hz, 1H), 4.01 (s, 3H). MS (M+H)$^+$: 232/234.

Step 3—Synthesis of
6-bromo-N-(4-chlorobenzyl)-3-methoxypicolinamide

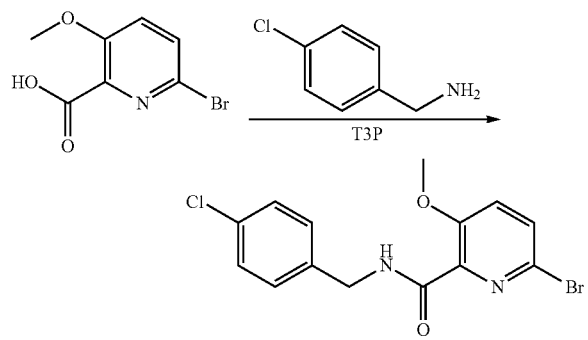

To a solution of (4-chlorophenyl)methanamine (610 mg, 4.31 mmol), 6-bromo-3-methoxypicolinic acid (1.0 g, 4.31 mmol) and triethylamine (1.31 g, 12.9 mmol) in DCM (10 mL) was added dropwise T3P (2.74 g, 8.61 mmol) at 0° C. Five minutes later, TLC indicated the reaction was complete, and the mixture was suspended in water and extracted with DCM. The organic phase was washed with brine, dried over sodium sulfate and concentrated in vacuo to give the crude 6-bromo-N-(4-chlorobenzyl)-3-methoxypicolinamide (1.3 g, yield: 87%) without further purification. $^1$H-NMR (DMSO-d$_6$, 400 MHz) δ 8.98 (t, J=6.0 Hz, 1H), 7.69 (d, J=8.8 Hz, 1H), 7.58 (d, J=8.8 Hz, 1H), 7.39~7.43 (m, 2H), 7.33 (d, J=8.4 Hz, 2H), 4.22 (d, J=6.4 Hz, 2H), 3.84 (s, 3H). MS (M+H)$^+$: 355/357.

Step 4—Synthesis of
6-bromo-N-(4-chlorobenzyl)-3-hydroxypicolinamide

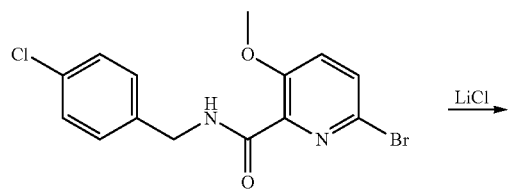

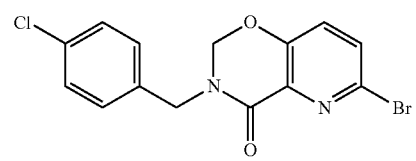

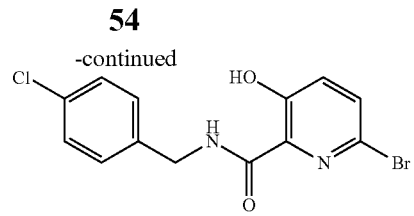

To a solution of 6-bromo-N-(4-chlorobenzyl)-3-methoxypicolinamide (800 mg, 2.25 mmol) in DMF (10 mL) was added lithium chloride (954 mg, 22.5 mmol), and the mixture was heated at 130° C. for 16 h. The mixture was concentrated in vacuo and the residue was suspended in water. Finally, the crude 6-bromo-N-(4-chlorobenzyl)-3-hydroxypicolinamide (700 mg, yield: 91%) was obtained by filtration. $^1$H-NMR (DMSO-d$_6$, 400 MHz) δ 12.47 (br s, 1H), 9.67 (s, 1H), 7.71 (d, J=8.8 Hz, 1H), 7.34~7.42 (m, 5H), 4.46 (d, J=6.0 Hz, 2H). MS (M+H)$^+$: 341/343.

Step 5—Synthesis of 6-bromo-3-(4-chlorobenzyl)-
2H-pyrido[2,3-e][1,3]oxazin-4(3H)-one

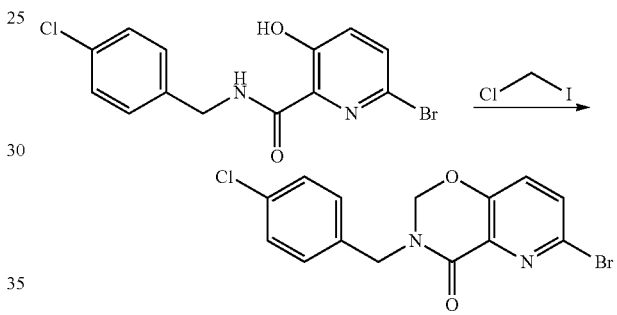

To a solution of 6-bromo-N-(4-chlorobenzyl)-3-hydroxypicolinamide (200 mg, 0.59 mmol) and Cs$_2$CO$_3$ (516 mg, 2.93 mmol) in DMF (5 mL) was added chloroiodomethane (382 mg, 1.17 mmol) dropwise at 100° C. for 10 minutes. The mixture was concentrated in vacuo and the residue was suspended in water. The mixture was extracted with EtOAc and the organic phase was washed with brine, dried over sodium sulfate and concentrated in vacuo to give the crude 6-bromo-3-(4-chlorobenzyl)-2H-pyrido[2,3-e][1,3]oxazin-4(3H)-one (150 mg, yield: 73%) without further purification. MS (M+H)$^+$: 353/355.

Step 6—Synthesis of 5-(3-(4-chlorobenzyl)-4-oxo-3,
4-dihydro-2H-pyrido[2,3-e][1,3]oxazin-6-yl)-2-(4-
fluorophenyl)-N-methyl-6-(N-methylmethylsulfona-
mido)benzofuran-3-carboxamide

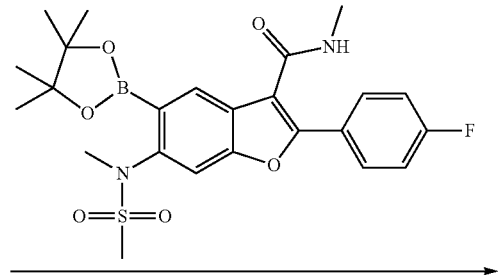

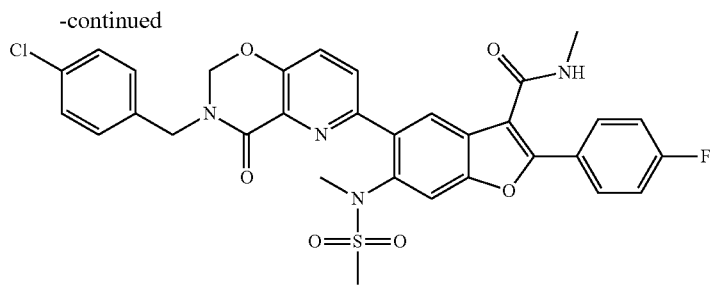

To a solution of 6-bromo-3-(4-chlorobenzyl)-2H-pyrido[2,3-e][1,3]oxazin-4(3H)-one (127 mg, 0.36 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (150 mg, 0.30 mmol) and $K_3PO_4 \cdot 3H_2O$ (159 mg, 0.60 mmol) in dioxane/water (2 mL/0.2 mL) was added Pd(dppf)Cl$_2$ (10 mg) under nitrogen. The mixture was heated at 100° C. for 5 h, and after concentrated in vacuo, the residue was suspended in water. The mixture was extracted with EtOAc and the organic phase was washed with brine then dried over sodium sulfate. The product 5-(3-(4-chlorobenzyl)-4-oxo-3,4-dihydro-2H-pyrido[2,3-e][1,3]oxazin-6-yl)-2-(4-fluorophenyl)-N-methyl-6-(N-methylmethylsulfonamido)benzofuran-3-carboxamide (140 mg, yield: 72%) was obtained with prep-TLC (DCM:MeOH=30:1). $^1$H-NMR (CDCl$_3$, 400 MHz) δ 7.95~7.98 (m, 3H), 7.76 (d, J=8.8 Hz, 1H), 7.63 (s, 1H), 7.45 (d, J=8.4 Hz, 1H), 7.30~7.36 (m, 4H), 7.20 (t, J=8.8 Hz, 2H), 6.07 (br s, 1H), 5.23 (s, 2H), 4.79 (s, 2H), 3.23 (s, 3H), 2.99 (d, J=4.8 Hz, 3H), 2.94 (s, 3H). MS (M+H)$^+$: 649/651.

Example 11

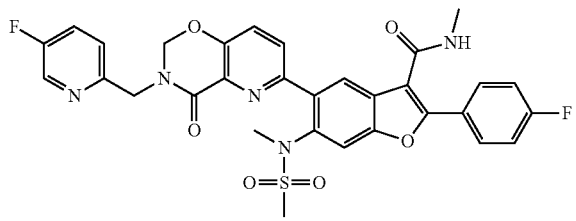

Step 1—Synthesis of methyl 6-(2-(4-fluorophenyl)-3-(methylcarbamoyl)-6-(N-methylmethylsulfonamido)benzofuran-5-yl)-3-methoxypicolinate

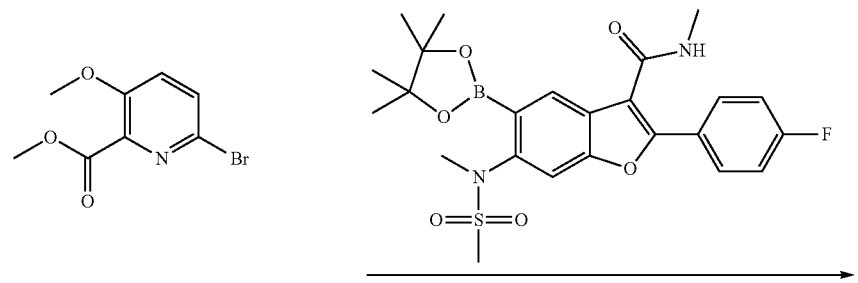

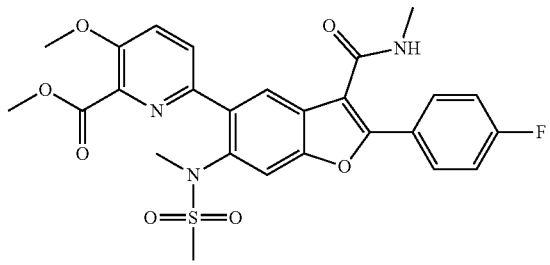

To a stirring mixture of methyl 6-bromo-3-methoxypicolinate (200 mg, 0.81 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (408 mg, 0.81 mmol) and K$_2$CO$_3$ (146 mg, 1.06 mmol) in dioxane/H$_2$O (4 mL/0.2 mL) was added Pd(dppf)Cl$_2$ (20 mg) under N$_2$ protection. The mixture was stirred at 60° C. for 5 h, and after concentrated in vacuo, the residue was extracted with EtOAc. The organic phase was washed with brine, dried over Na$_2$SO$_4$ and evaporated. The residue was purified by column chromatography (PE:EtOAc=2:1, then 1:1) to give the product of methyl 6-(2-(4-fluorophenyl)-3-(methylcarbamoyl)-6-(N-methylmethylsulfonamido)benzofuran-5-yl)-3-methoxypicolinate (400 mg, yield: 90%). $^1$H-NMR (CDCl$_3$, 400 MHz) δ 7.88~7.92 (m, 3H), 7.70 (d, J=8.8 Hz, 1H), 7.56 (s, 1H), 7.40 (d, J=8.8 Hz, 1H), 7.14 (t, J=8.8 Hz, 2H), 5.85 (d, J=3.2 Hz, 1H), 3.91 (s, 3H), 3.89 (s, 3H), 3.15 (s, 3H), 2.92 (d, J=4.8 Hz, 3H), 2.72 (s, 3H). MS (M+H)$^+$: 542.

Step 2—Synthesis of 6-(2-(4-fluorophenyl)-3-(methylcarbamoyl)-6-(N-methylmethylsulfonamido)benzofuran-5-yl)-3-methoxypicolinic acid

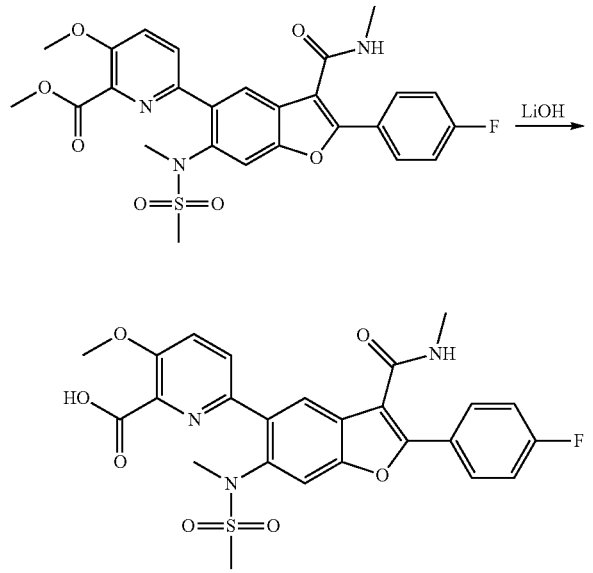

To a stirring solution of methyl 6-(2-(4-fluorophenyl)-3-(methylcarbamoyl)-6-(N-methylmethylsulfonamido)benzofuran-5-yl)-3-methoxypicolinate (400 mg, 0.74 mmol) in dioxane/H$_2$O (10 mL/1 mL) was added LiOH.H$_2$O (93 mg, 2.22 mmol) under N$_2$ protection. The mixture was stirred at 70° C. for 3 h. The mixture was concentrated in vacuo and then extracted with EtOAc. After the organic layer was washed with HCl (a.q.), brine, dried over Na$_2$SO$_4$, filtered and evaporated, the crude product was purified by prep-TLC (PE:EtOAc=1:3) to give the product of 6-(2-(4-fluorophenyl)-3-(methylcarbamoyl)-6-(N-methylmethylsulfonamido)benzofuran-5-yl)-3-methoxypicolinic acid (300 mg, yield: 77%). $^1$H-NMR (Methanol-d$_4$, 400 MHz) δ 7.86~7.90 (m, 2H), 7.80 (s, 1H), 7.69 (s, 1H), 7.65 (s, 1H), 7.55~7.57 (m, 1H), 7.14 (t, J=8.8 Hz, 2H), 3.83 (s, 3H), 3.04 (s, 3H), 2.86 (s, 3H), 2.82 (s, 3H). MS (M+H)$^+$: 528.

Step 3—Synthesis of 6-(2-(4-fluorophenyl)-3-(methylcarbamoyl)-6-(N-methylmethylsulfonamido)benzofuran-5-yl)-N-((5-fluoropyridin-2-yl)methyl)-3-methoxypicolinamide

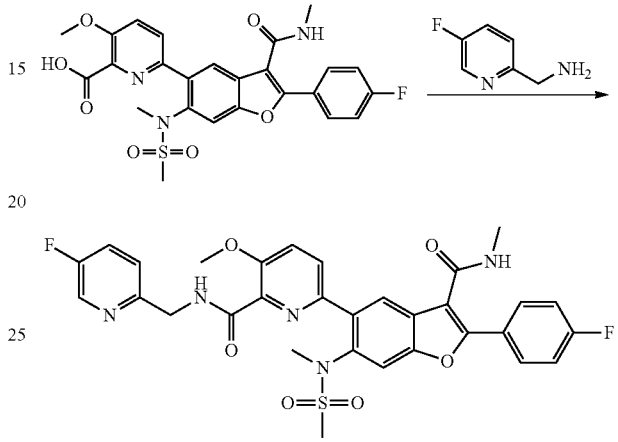

To a solution of 6-(2-(4-fluorophenyl)-3-(methylcarbamoyl)-6-(N-methylmethylsulfonamido)benzofuran-5-yl)-3-methoxypicolinic acid (50 mg, 0.09 mmol), (5-fluoropyridin-2-yl)methanamine (200 mg, 1.58 mmol) and Et$_3$N (0.2 mL) in THF (50 mL) was added T3P (0.05 mL) dropwise at 0° C. and the mixture was stirred for 3 h. After being diluted with water and extracted with EtOAc, the combined organic phases were washed with brine, dried over Na$_2$SO$_4$, filtered and evaporated. The residue was purified by prep-TLC (PE:EtOAc=1:2) to give the pure product of 6-(2-(4-fluorophenyl)-3-(methylcarbamoyl)-6-(N-methylmethylsulfonamido)benzofuran-5-yl)-N-((5-fluoropyridin-2-yl)methyl)-3-methoxypicolinamide (20 mg, yield: 30%). $^1$H-NMR (CDCl$_3$, 400 MHz) δ 8.60 (t, J=4.8 Hz, 1H), 8.36 (d, J=2.4 Hz, 1H), 7.99 (s, 1H), 7.92~7.95 (m, 2H), 7.73 (d, J=8.4 Hz, 1H), 7.58 (s, 1H), 7.48 (d, J=8.8 Hz, 1H), 7.24~7.42 (m, 2H), 7.17~7.22 (m, 2H), 5.91 (d, J=3.6 Hz, 1H), 4.73 (d, J=5.6 Hz, 2H), 4.01 (s, 3H), 3.18 (s, 3H), 2.97 (d, J=4.8 Hz, 3H), 2.78 (s, 3H). MS (M+H)$^+$: 636.

Step 4—Synthesis of 6-(2-(4-fluorophenyl)-3-(methylcarbamoyl)-6-(N-methylmethylsulfonamido)benzofuran-5-yl)-N-((5-fluoropyridin-2-yl)methyl)-3-hydroxypicolinamide

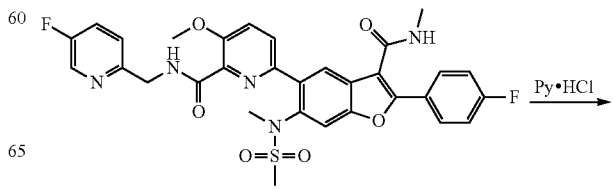

-continued

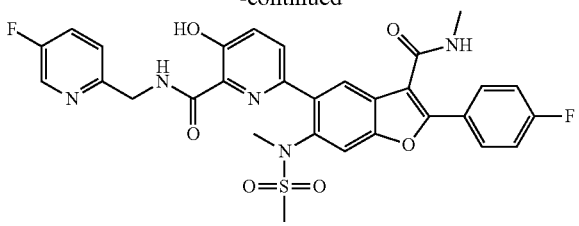

To a stirring solution of 6-(2-(4-fluorophenyl)-3-(methylcarbamoyl)-6-(N-methylmethylsulfonamido)benzofuran-5-yl)-N-((5-fluoropyridin-2-yl)methyl)-3-methoxypicolinamide (40 mg, 0.05 mmol) in DMF (5 mL) was added Py.HCl (400 mg, 2.22 mmol) under $N_2$ protection. The mixture was stirred in a pre-heated oil-bath at 100° C. for 10 h. The mixture was concentrated in vacuo, diluted with water and extracted with EtOAc. After being washed with brine, dried over $Na_2SO_4$, filtered and evaporated, the crude product was purified by prep-TLC (PE:EtOAc=2:1) to give the product of 6-(2-(4-fluorophenyl)-3-(methylcarbamoyl)-6-(N-methylmethylsulfonamido)benzofuran-5-yl)-N-((5-fluoropyridin-2-yl)methyl)-3-hydroxypicolinamide (20 mg, yield: 58%). $^1$H-NMR (CDCl$_3$, 400 MHz) δ 12.14 (s, 1H), 8.91 (d, J=5.6 Hz, 1H), 8.33 (s, 1H), 7.94 (s, 1H), 7.86~7.89 (m, 2H), 7.60 (d, J=8.8 Hz, 1H), 7.52 (s, 1H), 7.36 (d, J=8.8 Hz, 1H), 7.31~7.33 (m, 2H), 7.15 (d, J=8.8 Hz, 2H), 5.78 (d, J=4.0 Hz, 1H), 4.68 (d, J=5.6 Hz, 2H), 3.12 (s, 3H), 2.92 (d, J=4.8 Hz, 3H), 2.76 (s, 3H). MS (M+H)$^+$: 622.

Step 5—Synthesis of 2-(4-fluorophenyl)-5-(3-((5-fluoropyridin-2-yl)methyl)-4-oxo-3,4-dihydro-2H-pyrido[2,3-e][1,3]oxazin-6-yl)-N-methyl-6-(N-methylmethylsulfonamido)benzofuran-3-carboxamide To a solution of 6-(2-(4-fluorophenyl)-3-(methylcarbamoyl)-6-(N-methylmethylsulfonamido)benzofuran-5-yl)-N-((5-fluoropyridin-2-yl)methyl)-3-hydroxypicolinamide (30 mg, 0.05 mmol) and Cs$_2$CO$_3$ (47 mg, 0.14 mmol) in DMF (3 mL) at 100° C. was added chloroiodomethane (13 mg, 0.07 mmol) under $N_2$ protection dropwise. The mixture was stirred at 100° C. for 3 h. The mixture was concentrated, diluted with water and extracted with EtOAc. The organic phase was dried over Na$_2$SO$_4$ After concentration, the residue was purified by prep-HPLC to give the product of 2-(4-fluorophenyl)-5-(3-((5-fluoropyridin-2-yl)methyl)-4-oxo-3,4-dihydro-2H-pyrido[2,3-e][1,3]oxazin-6-yl)-N-methyl-6-(N-methylmethylsulfonamido)benzofuran-3-carboxamide (20 mg, yield: 60%). $^1$H-NMR (CDCl$_3$, 400 MHz) δ 8.33 (s, 1H), 7.90~7.94 (m, 3H), 7.69 (d, J=8.8 Hz, 1H), 7.56 (s, 1H), 7.40~7.44 (m, 2H), 7.31~7.36 (m, 1H), 7.13 (t, J=8.8 Hz, 2H), 6.19 (br s, 1H), 5.43 (s, 2H), 4.82 (s, 2H), 3.15 (s, 3H), 2.92 (d, J=4.8 Hz, 3H), 2.85 (s, 3H). MS (M+H)$^+$: 634.

Example 12

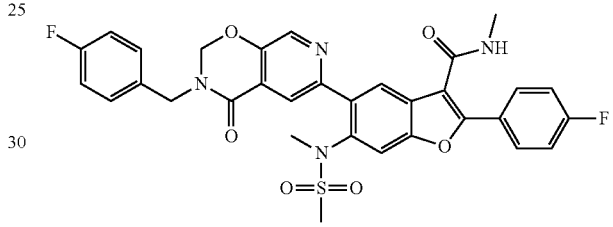

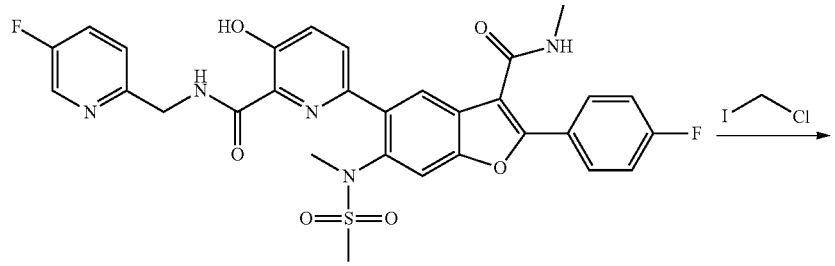

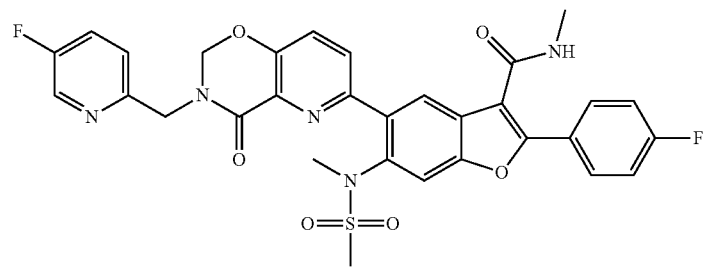 [SMILES: CNC(=O)c1c(-c2ccc(F)cc2)oc2cc(N(C)S(C)(=O)=O)c(-c3ccc4c(n3)C(=O)N(Cc3ccc(F)cn3)CO4)cc12]

Step 1—Synthesis of 2-bromo-5-methoxyisonicotinic acid

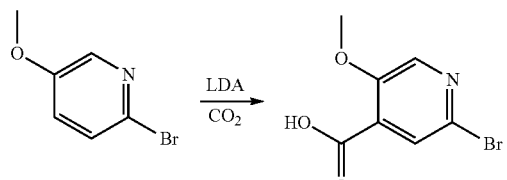

N-BuLi (21.3 mL, 2.5 M in hexane, 53.2 mmol) was added dropwise to a solution of i-Pr₂NH (5.9 g, 58.5 mmol) in THF (80 mL) at −78° C. The solution was stirred at 0° C. for 1 h. A solution of 2-bromo-5-methoxypyridine (10 g, 53.2 mmol) in THF (30 mL) was added dropwise to the LDA solution at −78° C. The mixture was stirred at −78° C. for 2 h and poured onto an excess of dry ice and allowed to warm to RT before being treated with NaOH (5% a.q., 100 mL). The mixture was washed with DCM and acidified to pH 4 by addition of HCl (6 N, 20 mL). The solids were collected by filtration to give the product of 2-bromo-5-methoxyisonicotinic acid (10 g, yield: 83%). $^1$H-NMR (DMSO-d₆, 400 MHz) δ 8.34 (s, 1H), 7.70 (s, 1H), 3.92 (s, 3H). MS (M+H)⁺: 232/233.

Step 2—Synthesis of 2-bromo-N-(4-fluorobenzyl)-5-methoxyisonicotinamide

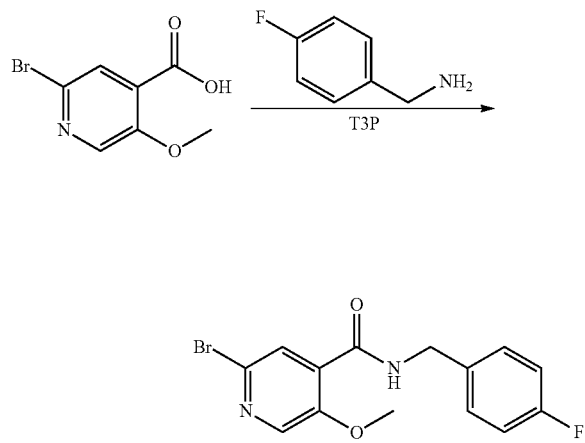

T3P (2.4 g, 7.4 mmol) was added to a solution of 2-bromo-5-methoxyisonicotinic acid (1.0 g, 3.7 mmol), (4-fluorophenyl)methanamine (466 mg, 3.7 mmol) and Et₃N (1.1 g, 11.1 mmol) in DCM (10 mL) at 0° C. The mixture was stirred at RT for 1 h. Water (50 mL) was added and the mixture was extracted with DCM. The organic layer was washed with brine and dried over Na₂SO₄. After being concentrated, the residue was purified by column chromatography (PE:EtOAc=2:1) to give the product of compound 2-bromo-N-(4-fluorobenzyl)-5-methoxyisonicotinamide (1.1 g, yield: 92%). $^1$H-NMR (CDCl₃, 400 MHz) δ 8.18 (d, J=2.8 Hz, 2H), 7.96 (s, 1H), 7.31 (dd, J=5.2, 8.4 Hz, 2H), 7.04 (t, J=8.8 Hz, 2H), 4.61 (d, J=6.0 Hz, 2H), 4.03 (s, 3H). MS (M+H)⁺: 339/341.

Step 3—Synthesis of 2-bromo-N-(4-fluorobenzyl)-5-hydroxyisonicotinamide

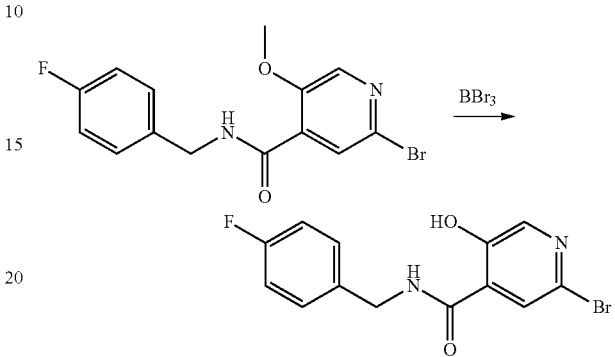

BBr₃ (20 mL) was added dropwise to a mixture of 2-bromo-N-(4-fluorobenzyl)-5-methoxyisonicotinamide (2.0 g, 5.9 mmol) in DCM (10 mL) at −78° C. The mixture was stirred at RT for 10 h, and then MeOH (20 mL) was added to quench the reaction. The mixture was concentrated in vacuum to give the product of compound 2-bromo-N-(4-fluorobenzyl)-5-hydroxyisonicotinamide (1.8 g, yield: 95%). $^1$H-NMR (DMSO-d₆, 400 MHz) δ 11.9 (s, 1H), 9.35 (s, 1H), 8.16 (s, 1H), 7.90 (s, 1H), 7.38 (t, J=6.0 Hz, 2H), 7.16 (d, J=8.8 Hz, 2H), 4.78 (s, 2H). MS (M+H)⁺: 325/327.

Step 4—Synthesis of 6-bromo-3-(4-fluorobenzyl)-2H-pyrido[4,3-e][1,3]oxazin-4(3H)-one

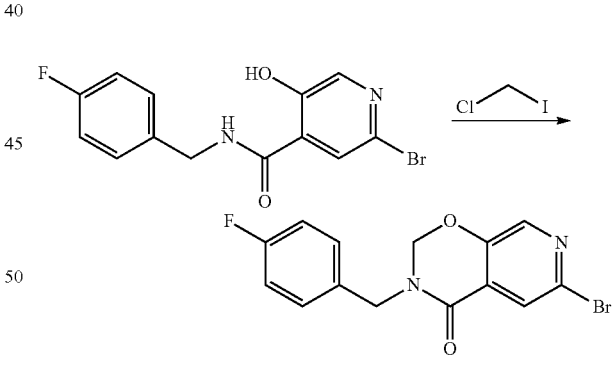

Chloroiodomethane (800 mg, 4.6 mmol) was slowly added to a mixture of 2-bromo-N-(4-fluorobenzyl)-5-hydroxyisonicotinamide (750 mg, 2.3 mmol) and Cs₂CO₃ (3.0 g, 9.2 mmol) in DMF (20 mL) at 100° C. The mixture was stirred at 100° C. for 2 h. Water was added and the mixture was extracted with EtOAc. After being concentrated, the residue was purified by column chromatography (PE:EtOAc=1:1) to give the product of 6-bromo-3-(4-fluorobenzyl)-2H-pyrido[4,3-e][1,3]oxazin-4(3H)-one (600 mg, yield: 80%). $^1$H-NMR (Methanol-d₄, 400 MHz) δ 8.24 (s, 1H), 7.94 (s, 1H), 7.39 (dd, J=5.6, 8.0 Hz, 2H), 7.09 (t, J=8.8 Hz, 2H), 5.34 (s, 2H), 4.75 (s, 2H). MS (M+H)⁺: 337/339.

Step 5—Synthesis of 5-(3-(4-fluorobenzyl)-4-oxo-3,4-dihydro-2H-pyrido[4,3-e][1,3]oxazin-6-yl)-2-(4-fluorophenyl)-N-methyl-6-(N-methylmethylsulfonamido)benzofuran-3-carboxamide

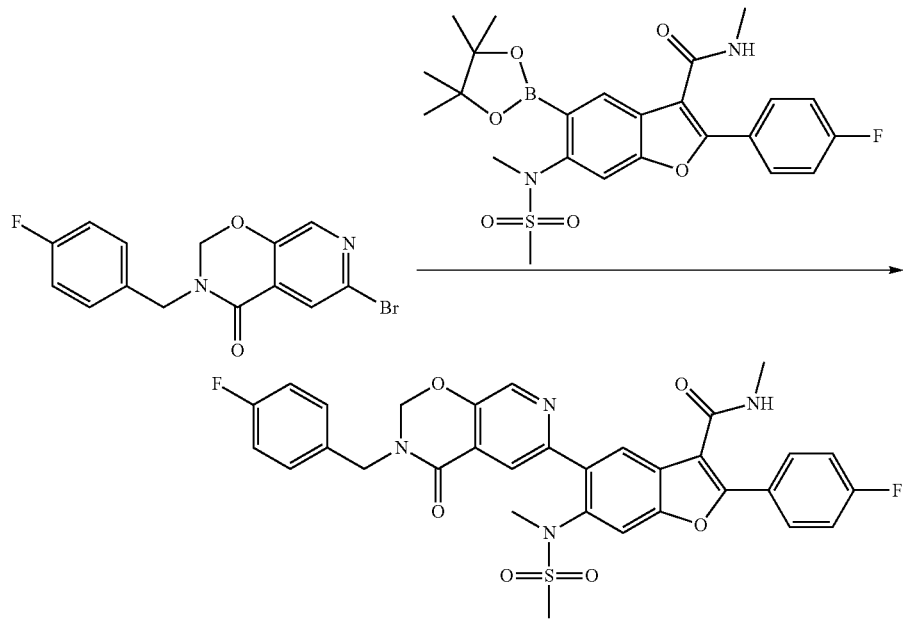

To a degassed solution of 2-(4-fluorophenyl)-N-methyl-6-(N-methylmethylsulfonamido)-5-(3-(4,4,5,5-tetramethyl-1,3,2-dioxaborolan-2-yl)phenyl)benzofuran-3-carboxamide (134 mg, 0.27 mmol) and 6-bromo-3-(4-fluorobenzyl)-2H-pyrido[4,3-e][1,3]oxazin-4(3H)-one (75 mg, 0.22 mmol) in DMF (2 mL) were added Pd(dppf)Cl$_2$ (18 mg, 0.02 mmol) and K$_3$PO$_4$ (331 mg, 0.66 mmol) under N$_2$. After being stirred at 100° C. overnight, the reaction mixture was cooled to RT and filtered. The filtrate was washed with brine and dried over Na$_2$SO$_4$. After being concentrated, the residue was purified by prep-TLC (PE:EtOAc=1:1) to give the product of 5-(3-(4-fluorobenzyl)-4-oxo-3,4-dihydro-2H-pyrido[4,3-e][1,3]oxazin-6-yl)-2-(4-fluorophenyl)-N-methyl-6-(N-methylmethylsulfonamido)benzofuran-3-carboxamide (80 mg, yield: 57%). $^1$H-NMR (CDCl$_3$, 400 MHz) δ 8.52 (s, 1H), 8.08 (s, 1H), 8.01~7.97 (m, 3H), 7.69 (s, 1H), 7.35 (dd, J=6.0, 8.4 Hz, 2H), 7.20 (t, J=8.4 Hz, 2H), 7.08 (t, J=8.4 Hz, 2H), 5.91 (s, 1H), 5.23 (s, 2H), 4.77 (s, 2H), 3.27 (s, 3H), 3.01 (d, J=4.8 Hz, 3H), 2.85 (s, 3H). MS (M+H)$^+$: 633.

Example 13

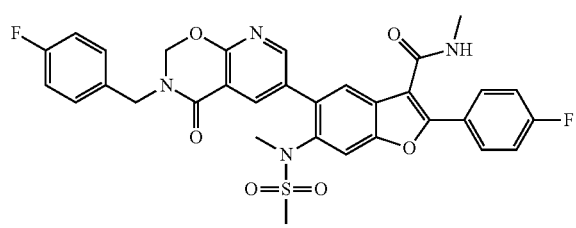 [SMILES: CNC(=O)c1c(-c2ccc(F)cc2)oc2cc(N(C)S(C)(=O)=O)c(-c3cnc4c(c3)C(=O)N(Cc3ccc(F)cc3)CO4)cc12]

Step 1—Synthesis of 5-bromo-N-(4-fluorobenzyl)-2-methoxynicotinamide

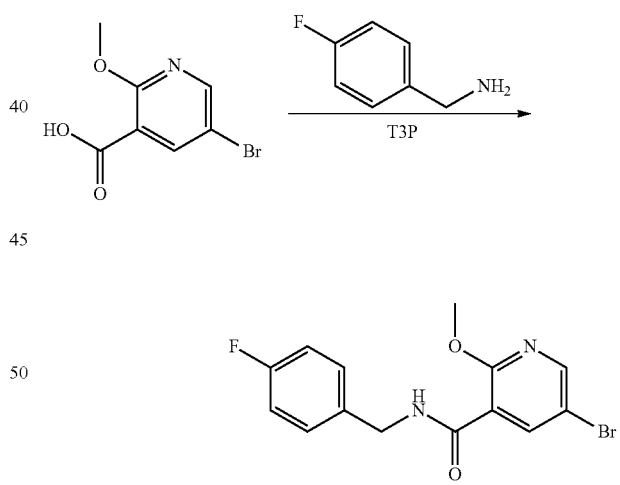

T3P (8.2 g, 25.8 mmol) was added to a solution of 5-bromo-2-methoxynicotinic acid (3 g, 12.9 mmol), (4-fluorophenyl)methanamine (1.6 g, 12.9 mmol) and Et$_3$N (3.9 g, 38.7 mmol) in DCM (50 mL) at 0° C. The mixture was stirred at RT for 1 h. Water (50 mL) was added and the mixture was extracted with DCM. The organic layer was washed with brine and dried over Na$_2$SO$_4$. After being concentrated, the residue was purified by column chromatography (PE:EtOAc=4:1) to give the product of 5-bromo-N-(4-fluorobenzyl)-2-methoxynicotinamide (4.0 g, yield: 91%). $^1$H-NMR (CDCl$_3$, 400 MHz) δ 8.64 (d, J=2.4 Hz, 1H), 8.31 (d, J=2.4

Hz, 1H), 8.17 (s, 1H), 7.32 (dd, J=5.2, 8.4 Hz, 2H), 7.04 (t, J=8.8 Hz, 2H), 4.63 (d, J=6.0 Hz, 2H), 4.05 (s, 3H). MS (M+H)+: 339/341

Step 2—Synthesis of 5-bromo-N-(4-fluorobenzyl)-2-hydroxynicotinamide

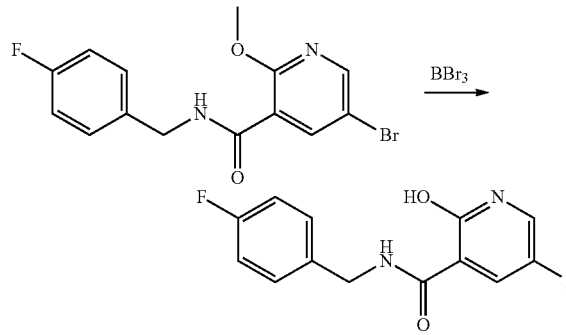

BBr₃ (20 mL) was added dropwise to a mixture of compound 5-bromo-N-(4-fluorobenzyl)-2-methoxynicotinamide (2.0 g, 5.9 mmol) in DCM (10 mL) at −78° C. The mixture was stirred at RT for 10 h, and then MeOH (20 mL) was added to quench the reaction. The mixture was concentrated in vacuum to give the product of 5-bromo-N-(4-fluorobenzyl)-2-hydroxynicotinamide (1.8 g, yield: 95%). ¹H-NMR (DMSO-d₆, 400 MHz) δ 12.9 (s, 1H), 10.0 (t, J=4.8 Hz, 1H), 8.30 (d, J=2.8 Hz, 1H), 8.02 (s, 1H), 7.34 (dd, J=6.0, 8.8 Hz, 2H), 7.15 (d, J=8.8 Hz, 2H), 4.50 (s, 2H). MS (M+H)+: 325/327

Step 3—Synthesis of 6-bromo-3-(4-fluorobenzyl)-2H-pyrido[3,2-e][1,3]oxazin-4(3H)-one

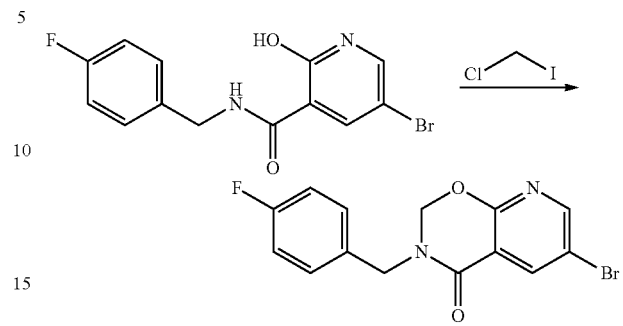

Chloroiodomethane (897 mg, 5.1 mmol) was slowly added to a mixture of 5-bromo-N-(4-fluorobenzyl)-2-hydroxynicotinamide (1.5 g, 4.6 mmol) and Cs₂CO₃ (6.0 g, 18.4 mmol) in DMF (20 mL) at 100° C. The mixture was stirred at 100° C. for 2 h. Water was added and the mixture was extracted with EtOAc. After being concentrated, the residue was purified by column chromatography (PE:EtOAc=2:1) to give the product of 6-bromo-3-(4-fluorobenzyl)-2H-pyrido[3,2-e][1,3]oxazin-4(3H)-one (140 mg, yield: 9%). ¹H-NMR (DMSO-d₆, 400 MHz) δ 8.46 (d, J=2.4 Hz, 1H), 8.44 (d, J=2.4 Hz, 1H), 7.40 (dd, J=5.6, 8.8 Hz, 2H), 7.09 (t, J=8.8 Hz, 2H), 5.40 (s, 2H), 4.74 (s, 2H). MS (M+H)+: 337/339.

Step 4—Synthesis of 5-(3-(4-fluorobenzyl)-4-oxo-3,4-dihydro-2H-pyrido[3,2-e][1,3]oxazin-6-yl)-2-(4-fluorophenyl)-N-methyl-6-(N-methylmethylsulfonamido)benzofuran-3-carboxamide

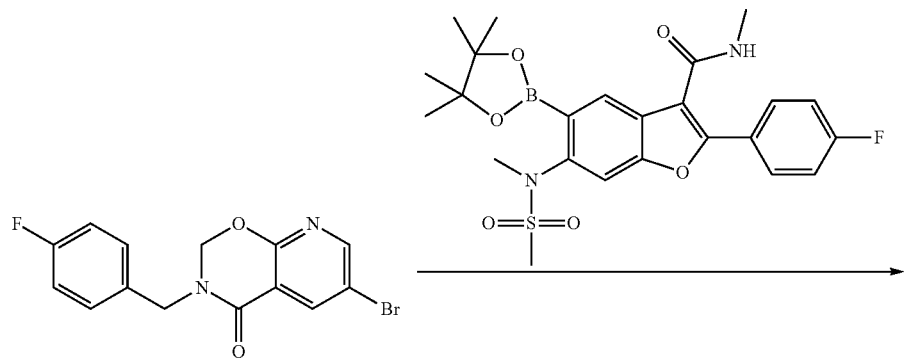

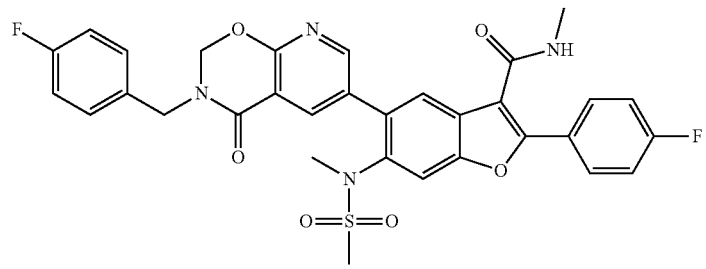

To a degassed solution of 2-(4-fluorophenyl)-N-methyl-6-(N-methylmethylsulfonamido)-5-(3-(4,4,5,5-tetramethyl-1,3,2-dioxaborolan-2-yl)phenyl)benzofuran-3-carboxamide (98 mg, 0.19 mmol) and 6-bromo-3-(4-fluorobenzyl)-2H-pyrido[3,2-e][1,3]oxazin-4(3H)-one (60 mg, 0.18 mmol) in DMF (2 mL) were added Pd(dppf)Cl$_2$ (16 mg, 0.02 mmol) and K$_3$PO$_4$ (270 mg, 0.54 mmol) under N$_2$. After being stirred at 100° C. overnight, the reaction mixture was cooled to RT and filtered. The filtrate was washed with brine and dried over Na$_2$SO$_4$. After being concentrated, the residue was purified by prep-TLC (PE:EtOAc=1:1) to give the product of 5-(3-(4-fluorobenzyl)-4-oxo-3,4-dihydro-2H-pyrido[3,2-e][1,3]oxazin-6-yl)-2-(4-fluorophenyl)-N-methyl-6-(N-methylmethylsulfonamido)benzofuran-3-carboxamide (80 mg, yield: 70%). $^1$H-NMR (CDCl$_3$, 400 MHz) δ 8.48 (d, J=2.4 Hz, 1H), 8.44 (d, J=2.4 Hz, 1H), 7.94 (dd, J=5.2, 8.8 Hz, 2H), 7.86 (s, 1H), 7.65 (s, 1H), 7.35 (dd, J=5.2, 8.4 Hz, 2H), 7.22 (t, J=8.8 Hz, 2H), 7.07 (t, J=8.8 Hz, 2H), 5.86 (d, J=4.4 Hz, 1H), 5.31 (s, 2H), 4.75 (s, 2H), 3.21 (s, 3H), 3.00 (d, J=5.2 Hz, 3H), 2.86 (s, 3H). MS (M+H)$^+$: 633.

Example 14

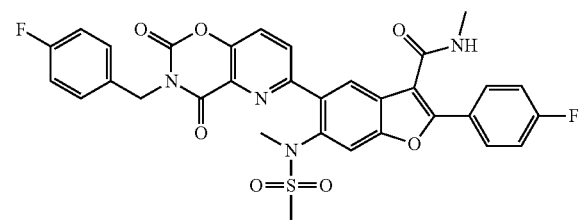 [SMILES: CNC(=O)c1c(-c2ccc(F)cc2)oc2cc(N(C)S(C)(=O)=O)c(-c3ccc4oc(=O)n(Cc5ccc(F)cc5)c(=O)c4n3)cc12]

Step 1—Synthesis of methyl 3-(benzyloxy)-6-(2-(4-fluorophenyl)-3-(methylcarbamoyl)-6-(N-methylmethylsulfonamido)benzofuran-5-yl)picolinate

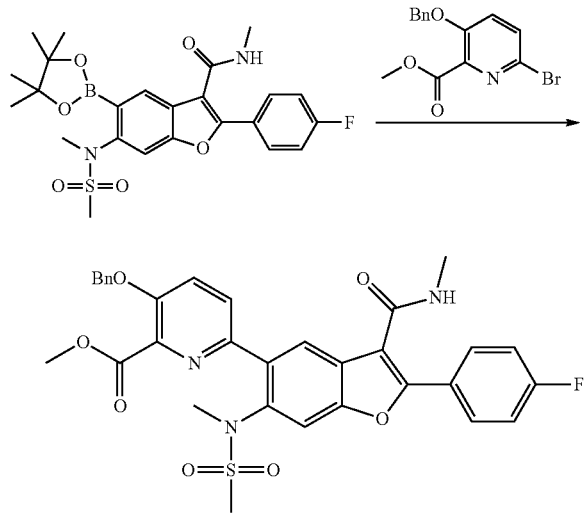

Pd$_2$(dba)$_3$ (45 mg, 0.05 mmol) and X-phos (48 mg, 0.1 mmol) were added to a mixture of 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (500 mg, 1 mmol), methyl 3-(benzyloxy)-6-bromopicolinate (350 mg, 1.1 mmol) and K$_3$PO$_4$.3H$_2$O (798 mg, 3 mmol) in 1,4-dioxane/H$_2$O (5 mL/0.5 mL) under N$_2$. The mixture was stirred at 80° C. for 8 h, and after being filtered through celite, the filtrate was concentrated in vacuo, diluted with water and extracted with EtOAc. The residue was purified by column chromatography (DCM:EtOAc=40:1 to 10:1) to obtain methyl 3-(benzyloxy)-6-(2-(4-fluorophenyl)-3-(methylcarbamoyl)-6-(N-methylmethylsulfonamido)benzofuran-5-yl)picolinate (540 mg, yield: 88%). $^1$H-NMR (CDCl$_3$, 400 MHz) δ 7.88~8.04 (m, 3H), 7.70 (d, J=8.8 Hz, 1H), 7.62 (s, 1H), 7.45~7.56 (m, 3H), 7.41 (t, J=7.2 Hz, 2H), 7.32~7.38 (m, 1H), 7.20 (t, J=8.4 Hz, 2H), 5.90 (d, J=4.0 Hz, 1H), 5.27 (s, 2H), 3.97 (s, 3H), 3.22 (s, 3H), 2.98 (d, J=4.8 Hz, 3H), 2.72 (s, 3H). MS (M+H)$^+$: 618.

Step 2—Synthesis of 3-(benzyloxy)-6-(2-(4-fluorophenyl)-3-(methylcarbamoyl)-6-(N-methylmethylsulfonamido)benzofuran-5-yl)picolinic acid

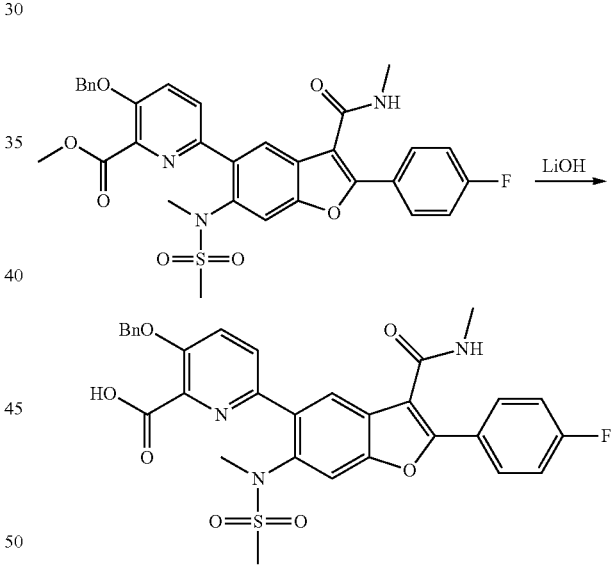

A mixture of methyl 3-(benzyloxy)-6-(2-(4-fluorophenyl)-3-(methylcarbamoyl)-6-(N-methylmethylsulfonamido)benzofuran-5-yl)picolinate (540 mg, 0.87 mmol), LiOH.H$_2$O (110 mg, 2.62 mmol) in 1,4-dioxane/H$_2$O (15 mL/5 mL) under N$_2$ was stirred at 100° C. for 1 h. After being filtrated and acidified with HCl to pH=5, the mixture was extracted with EtOAc, the organic phases were dried and concentrated to afford 3-(benzyloxy)-6-(2-(4-fluorophenyl)-3-(methylcarbamoyl)-6-(N-methylmethylsulfonamido)benzofuran-5-yl)picolinic acid (520 mg, yield: 98%). $^1$H-NMR (DMSO-d$_6$, 400 MHz) δ 8.56 (d, J=4.8 Hz, 1H), 7.94~8.07 (m, 3H), 7.73~7.85 (m, 3H), 7.50 (d, J=7.2 Hz, 2H), 7.42 (t, J=7.6 Hz, 4H), 7.35 (br s, 1H), 5.30 (s, 2H), 3.20 (s, 3H), 2.94 (s, 3H), 2.82 (d, J=4.4 Hz, 3H). MS (M+H)$^+$: 604.

Step 3—Synthesis of 3-(benzyloxy)-N-(4-fluorobenzyl)-6-(2-(4-fluorophenyl)-3-(methylcarbamoyl)-6-(N-methylmethylsulfonamido)benzofuran-5-yl)picolinamide

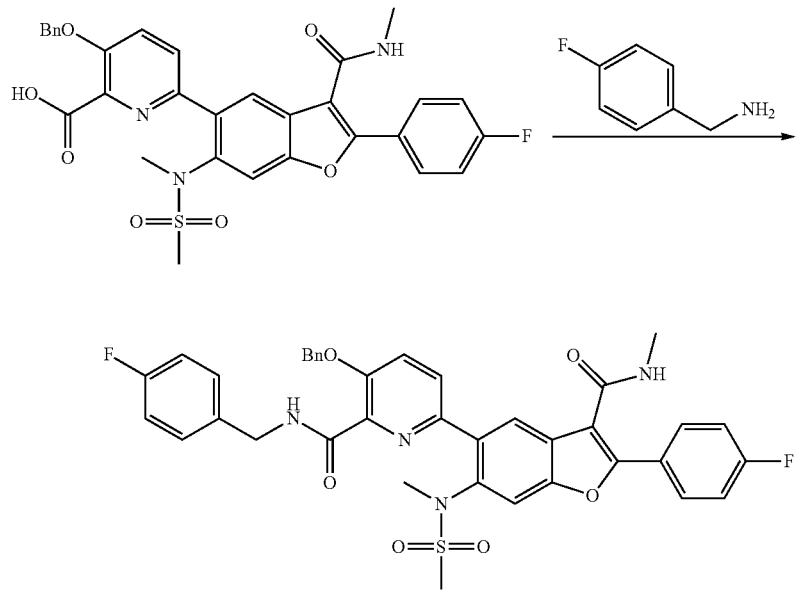 [SMILES: CNC(=O)c1c(-c2ccc(F)cc2)oc2cc(N(C)S(C)(=O)=O)c(-c3ccc(OCc4ccccc4)c(C(=O)O)n3)cc12 ; NCc1ccc(F)cc1 ; CNC(=O)c1c(-c2ccc(F)cc2)oc2cc(N(C)S(C)(=O)=O)c(-c3ccc(OCc4ccccc4)c(C(=O)NCc4ccc(F)cc4)n3)cc12]

A mixture of 3-(benzyloxy)-6-(2-(4-fluorophenyl)-3-(methylcarbamoyl)-6-(N-methylmethylsulfonamido)benzofuran-5-yl)picolinic acid (200 mg, 0.33 mmol), HATU (252 mg, 0.66 mmol) and Et₃N (111 mg, 1 mmol) was stirred in DMF (5 mL) at RT for 1 h, and then (4-fluorophenyl)methanamine (124 mg, 1 mmol) was added. After being stirred for 3 h, the mixture was diluted with water and extracted with EtOAc. The organic layer was concentrated and purified by column chromatography (DCM:MeOH=100:1 to 50:1) to get the product of 3-(benzyloxy)-N-(4-fluorobenzyl)-6-(2-(4-fluorophenyl)-3-(methylcarbamoyl)-6-(N-methylmethylsulfonamido)benzofuran-5-yl)picolinamide (225 mg, yield: 96%). ¹H-NMR (Methanol-d₄, 400 MHz) δ 7.90~7.94 (m, 2H), 7.83 (s, 1H), 7.76 (s, 1H), 7.65~7.72 (m, 2H), 7.43~7.45 (m, 2H), 7.28~7.34 (m, 5H), 7.22 (t, J=8.6 Hz, 2H), 6.91 (t, J=8.6 Hz, 2H), 5.20 (s, 2H), 4.50 (s, 2H), 3.14 (s, 3H), 2.89 (s, 3H), 2.87 (s, 3H). MS (M+H)⁺: 711.

Step 4—Synthesis of N-(4-fluorobenzyl)-6-(2-(4-fluorophenyl)-3-(methylcarbamoyl)-6-(N-methylmethylsulfonamido)benzofuran-5-yl)-3-hydroxypicolinamide

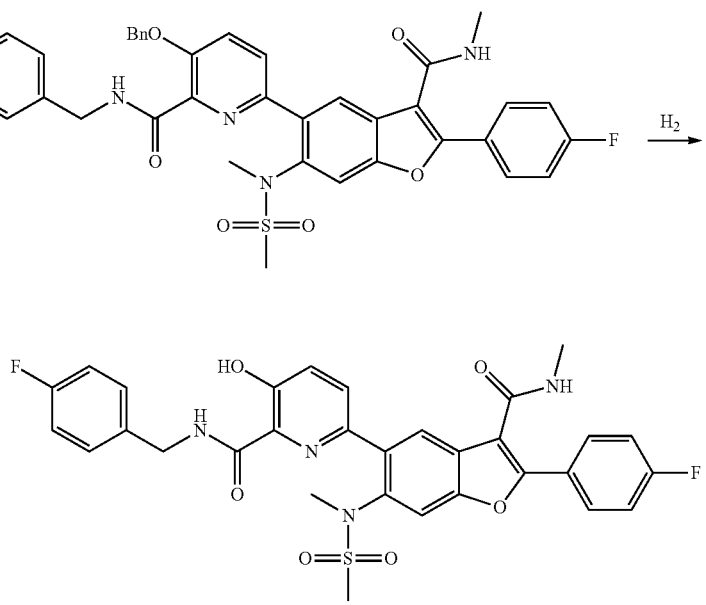

To a solution of 3-(benzyloxy)-N-(4-fluorobenzyl)-6-(2-(4-fluorophenyl)-3-(methylcarbamoyl)-6-(N-methylmethylsulfonamido)benzofuran-5-yl)picolinamide (361 mg, 0.51 mmol) in CH₃OH (5 mL) was added Pd—C under Ar. The suspension was degassed under vacuum and purged with H₂ several times. The mixture was stirred under H₂ at RT overnight. After being filtered through celite and removal of the solvent by concentration, the residue was purified by prep-TLC (DCM:MeOH=60:1) to afford the product of N-(4-fluorobenzyl)-6-(2-(4-fluorophenyl)-3-(methylcarbamoyl)-6-(N-methylmethylsulfonamido)benzofuran-5-yl)-3-hydroxypicolinamide. (220 mg, yield: 70%). $^1$H-NMR (CDCl₃, 400 MHz) δ 12.27 (s, 1H), 8.61~8.64 (m, 1H), 7.91~7.96 (m, 3H), 7.64 (d, J=8.8 Hz, 1H), 7.55 (s, 1H), 7.42 (d, J=8.4 Hz, 1H), 7.35 (dd, J=5.6, 8.4 Hz, 2H), 7.21 (t, J=8.4 Hz, 2H), 7.01 (t, J=8.4 Hz, 2H), 5.80 (d, J=3.6 Hz, 1H), 4.59 (d, J=6.4 Hz, 2H), 3.04 (s, 3H), 2.97 (d, J=5.2 Hz, 3H), 2.91 (s, 3H). MS (M+H)⁺: 621.

Step 5—Synthesis of 5-(3-(4-fluorobenzyl)-2,4-dioxo-3,4-dihydro-2H-pyrido[2,3-e][1,3]oxazin-6-yl)-2-(4-fluorophenyl)-N-methyl-6-(N-methylmethylsulfonamido)benzofuran-3-carboxamide

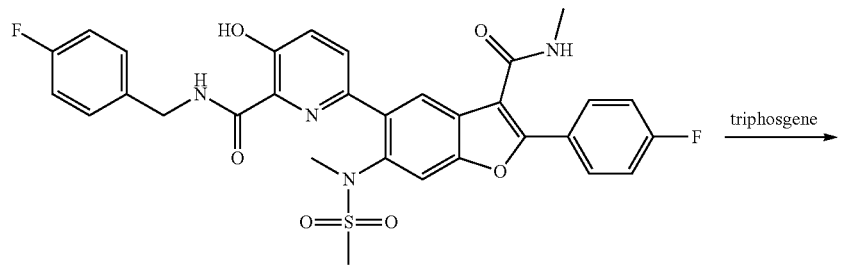

3H), 7.19 (t, J=8.4 Hz, 2H), 7.01 (t, J=8.4 Hz, 2H), 6.14 (d, J=4.4 Hz, 1H), 5.20 (s, 2H), 3.24 (s, 3H), 2.98 (d, J=4.8 Hz, 3H), 2.95 (s, 3H). MS (M+H)⁺: 647.

Example 15

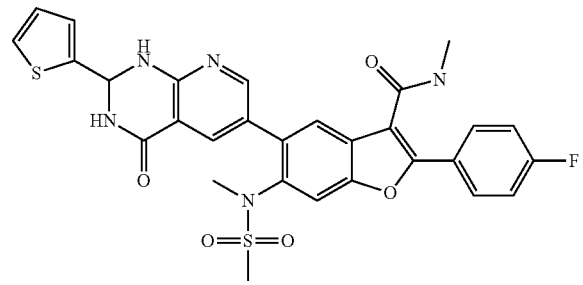 [SMILES: CNC(=O)c1c(-c2ccc(F)cc2)oc2cc(N(C)S(C)(=O)=O)c(-c3cnc4c(c3)C(=O)NC(c3cccs3)N4)cc12]

A mixture of N-(4-fluorobenzyl)-6-(2-(4-fluorophenyl)-3-(methylcarbamoyl)-6-(N-methylmethylsulfonamido)benzofuran-5-yl)-3-hydroxypicolinamide (30 mg, 0.05 mmol) and Et₃N (11 mg, 0.10 mmol) in CH₂Cl₂ (5 mL) was stirred at RT under N₂ atmosphere, and then triphosgene (18 mg, 0.06 mmol) was added portionwise. The mixture was stirred at RT for 4 h. The solvent was removed by rotary evaporator. After purified by prep-TLC (DCM:MeOH=60:1), 5-(3-(4-fluorobenzyl)-2,4-dioxo-3,4-dihydro-2H-pyrido[2,3-e][1,3]oxazin-6-yl)-2-(4-fluorophenyl)-N-methyl-6-(N-methylmethylsulfonamido)benzofuran-3-carboxamide was obtained. (15 mg, yield: 48%). $^1$H-NMR (CDCl₃, 400 MHz) δ 7.97~8.05 (m, 2H), 7.92 (m, 2H), 7.72 (d, J=8.4 Hz, 1H), 7.52~7.63 (m, Step 1—Synthesis of 2-amino-5-bromonicotinamide

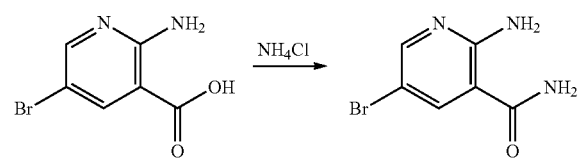 [SMILES: Nc1ncc(Br)cc1C(=O)O ; "NH4Cl" ; NC(=O)c1cc(Br)cnc1N]

A mixture of 2-amino-5-bromonicotinic acid (2.0 g, 9.20 mmol), HOBT (1.40 g, 11.2 mmol), EDCI (3.52 g, 18.4 mmol), Et₃N (4.68 g, 46.0 mmol) and NH₄Cl (2.48 g, 46.0 mmol) in DMF (100 mL) was stirred overnight at room temperature. The reaction mixture was concentrated in vacuo, suspended in water and extracted with CH₂Cl₂. The organic layer was washed with brine, dried over Na₂SO₄ and concentrated to give the product of 2-amino-5-bromonicotinamide (1.80 g, yield: 80%), which was used for the next step without further purification. ¹H NMR (DMSO-d₆, 400 MHz) δ 8.14 (dd, J=4.4 Hz, 2.4 Hz, 2H), 8.04 (s, 1H), 7.46 (s, 1H), 7.37 (s, 2H). MS (M+H)⁺: 216/218.

Step 2—Synthesis of 6-bromo-2-(thiophen-2-yl)-2,3-dihydropyrido[2,3-d]pyrimidin-4(1H)-one

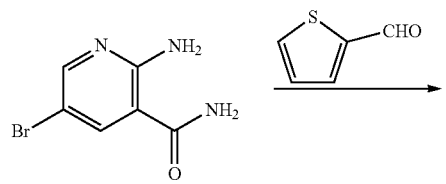

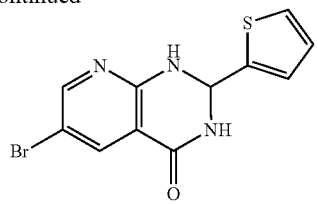

To a mixture of 2-amino-5-bromonicotinamide (200 mg, 0.93 mmol), thiophene-2-carbaldehyde (125 mg, 1.11 mmol) in MeOH (15 mL) was added 4-methylbenzenesulfonic acid (16 mg, 0.09 mmol). The mixture was stirred at 60° C. overnight. Then the resulting solid was filtered to give the product of 6-bromo-2-(thiophen-2-yl)-2,3-dihydropyrido[2,3-d]pyrimidin-4(1H)-one (180 mg, yield: 63%), which was used for the next step without further purification. ¹H NMR (DMSO-d₆, 400 MHz) δ 8.93 (d, J=2.4 Hz, 1H), 8.42 (s, 1H), 8.28 (d, J=2.4 Hz, 1H), 7.98 (d, J=2.4 Hz, 1H), 7.45 (dd, J=4.8 Hz, 1.2 Hz, 1H), 7.08 (d, J=3.2 Hz, 1H), 6.98 (dd, J=4.8 Hz, 3.2 Hz, 1H), 6.10 (t, J=2.4 Hz, 1H). MS (M+H)⁺: 310/312.

Step 3—Synthesis of 2-(4-fluorophenyl)-N-methyl-6-(N-methylmethylsulfonamido)-5-(4-oxo-2-(thiophen-2-yl)-1,2,3,4-tetrahydropyrido[2,3-d]pyrimidin-6-yl)benzofuran-3-carboxamide

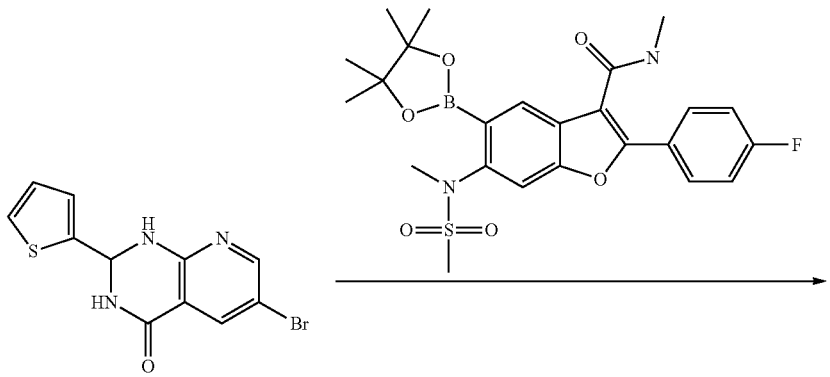

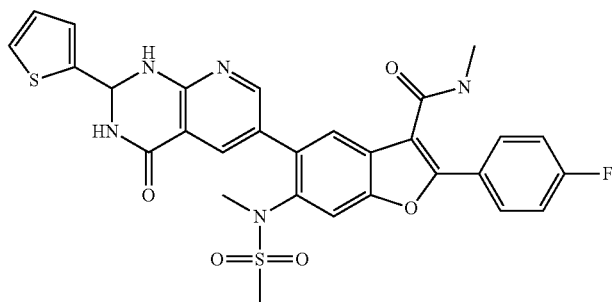

To a mixture of 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (150 mg, 0.30 mmol), compound 6-bromo-2-(thiophen-2-yl)-2,3-dihydropyrido[2,3-d]pyrimidin-4(1H)-one (112 mg, 0.36 mmol) and $K_3PO_4 \cdot 3H_2O$ (239 mg, 0.90 mmol) in 1,4-dioxane (3 mL), Pd(dppf)Cl$_2$ (20 mg) was added under N$_2$ protection. After being stirred at 80° C. overnight, the reaction mixture was concentrated in vacuo, suspended in water and extracted with EtOAc. The organic layer was washed with brine, dried over Na$_2$SO$_4$ and concentrated. The residue was purified by prep-HPLC to give the product of 2-(4-fluorophenyl)-N-methyl-6-(N-methylmethylsulfonamido)-5-(4-oxo-2-(thiophen-2-yl)-1,2,3,4-tetrahydropyrido[2,3-d]pyrimidin-6-yl)benzofuran-3-carboxamide (40 mg, yield: 22%). $^1$H-NMR (DMSO-d$_6$, 400 MHz) δ 8.80 (d, J=1.6 Hz, 1H), 8.51 (d, J=4.4 Hz, 1H), 8.26 (d, J=2.0 Hz, 1H), 8.22 (s, 1H), 7.95~8.05 (m, 4H), 7.60 (s, 1H), 7.47 (dd, J=5.2, 1.2 Hz, 1H), 7.41 (t, J=8.8 Hz, 2H), 7.12 (d, J=2.8 Hz, 1H), 7.00 (dd, J=4.8, 3.2 Hz, 1H), 6.14 (d, J=2.4 Hz, 1H), 3.14 (s, 3H), 2.98 (s, 3H), 2.83 (d, J=4.4 Hz, 3H). MS (M+H)$^+$: 606

Example 16, depicted in the table below, was prepared using the method described above.

| Example | Structure | NMR | MS (M + H)$^+$ |
|---|---|---|---|
| 16 | 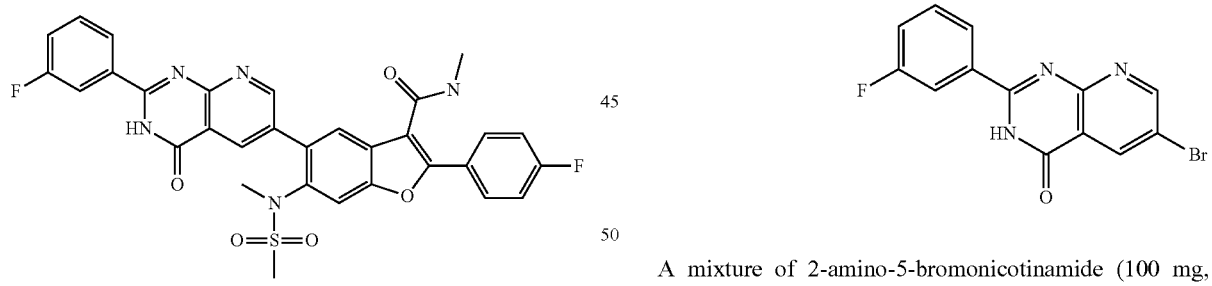 | $^1$H-NMR (DMSO-d$_6$, 400 MHz) δ 8.52 (d, J = 4.4, 1H), 8.35 (s, 1H), 8.22 (d, J = 2.4 Hz, 1H), 7.96~8.05 (m, 3H), 7.95 (d, J = 2.4 Hz, 1H), 7.69 (s, 1H), 7.59 (s, 1H), 7.38~7.44 (m, 2H), 4.16 (d, J = 7.2 Hz, 1H), 3.14 (s, 3H), 3.02 (s, 3H), 2.83 (d, J = 4.4 Hz, 3H), 1.15~1.21 (m, 1H), 0.45~0.49 (m, 2H), 0.34~0.39 (m, 2H). | 564 |

Example 17

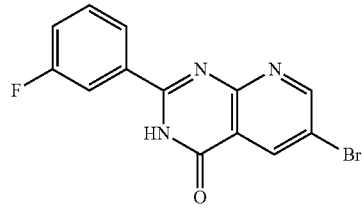

Step 1—Synthesis of 6-bromo-2-(3-fluorophenyl)pyrido[2,3-d]pyrimidin-4(3H)-one

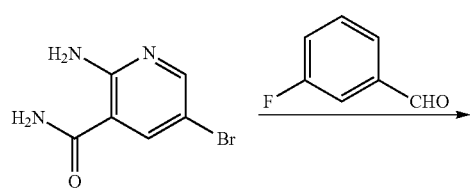

A mixture of 2-amino-5-bromonicotinamide (100 mg, 0.46 mmol), 3-fluorobenzaldehyde (69 mg, 0.56 mmol), NaHSO$_3$ (40 mg, 0.38 mmol), 4-methylbenzene sulfonic acid (15 mg, 0.05 mmol) in DMAc (3 mL) was stirred at 115° C. for 1.5 h, then additional NaHSO$_3$ (40 mg, 0.38 mmol) was added to the mixture. After 1.5 h, the third portion of NaHSO$_3$ (40 mg, 0.38 mmol) was added to the mixture. After being stirred overnight at 115° C., the reaction mixture was concentrated in vacuo, suspended in water and filtered to give the product of 6-bromo-2-(3-fluorophenyl)pyrido[2,3-d]pyrimidin-4(3H)-one (70 mg, yield: 47%), which was used for the next step without further purification. $^1$H-NMR (DMSO-d$_6$, 400 MHz) δ 13.04 (br s, 1H), 9.07 (d, J=2.8 Hz, 1H), 8.65 (d, J=2.8 Hz, 1H), 8.08 (d, J=8.0 Hz, 1H), 8.02 (dd, J=9.6, 1.6 Hz, 1H), 7.60~7.68 (m, 1H), 7.45~7.54 (m, 1H). MS (M+H)$^+$: 320/322.

Step 2—Synthesis of 2-(4-fluorophenyl)-5-(2-(3-fluorophenyl)-4-oxo-3,4-dihydropyrido[2,3-d]pyrimidin-6-yl)-N-methyl-6-(N-methylmethylsulfonamido)benzofuran-3-carboxamide

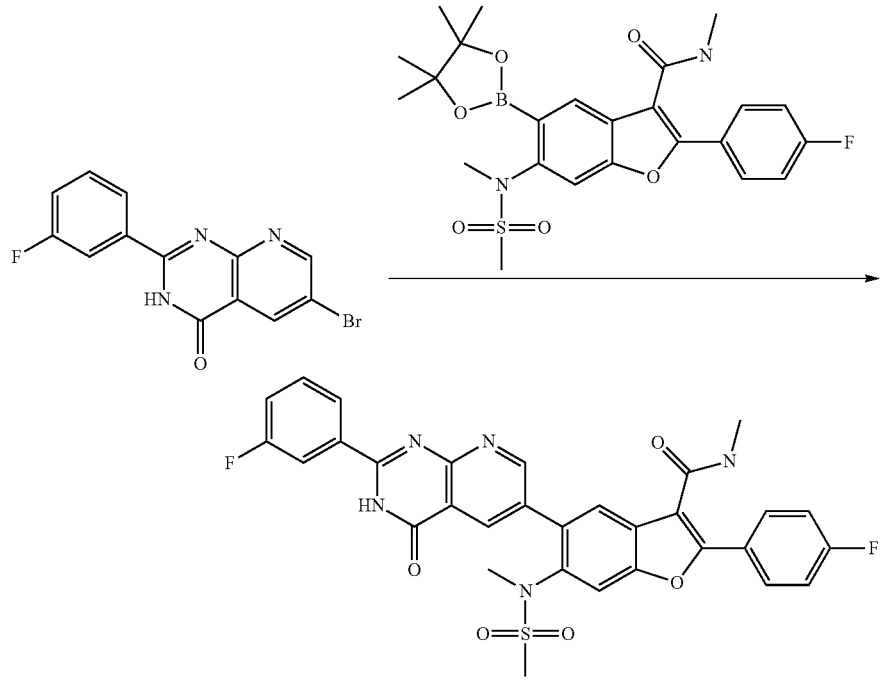

To a mixture of 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (90 mg, 0.18 mmol), 2-(3-fluorophenyl)pyrido[2,3-d]pyrimidin-4(3H)-one (63 mg, 0.19 mmol) and K$_3$PO$_4$·3H$_2$O (143 mg, 0.54 mmol) in 1,4-dioxane/H$_2$O (3 mL/0.3 mL), Pd$_2$(dba)$_3$ and X-Phos (10 mg/10 mg) were added under N$_2$ protection. After being stirred at 80° C. for 5 h, the reaction mixture was concentrated in vacuo, suspended in water and extracted with EtOAc. The organic layer was washed with brine, dried over Na$_2$SO$_4$ and concentrated. The residue was purified by prep-HPLC give the product of 2-(4-fluorophenyl)-5-(2-(3-fluorophenyl)-4-oxo-3,4-dihydropyrido[2,3-d]pyrimidin-6-yl)-N-methyl-6-(N-methylmethylsulfonamido)benzofuran-3-carboxamide (15 mg, yield: 13%). $^1$H-NMR (DMSO-d$_6$, 400 MHz) δ 12.97 (br s, 1H), 9.03 (d, J=2.4 Hz, 1H), 8.50~8.60 (m, 2H), 8.16 (s, 1H), 8.12 (d, J=7.6 Hz, 1H), 8.00~8.09 (m, 3H), 7.79 (s, 1H), 7.65 (dd, J=14.0, 8.0 Hz, 1H), 7.46~7.52 (m, 1H), 7.43 (t, J=8.8 Hz, 2H), 3.26 (s, 3H), 3.02 (s, 3H), 2.85 (d, J=4.8 Hz, 3H). MS (M+H)$^+$: 616.

Example 18

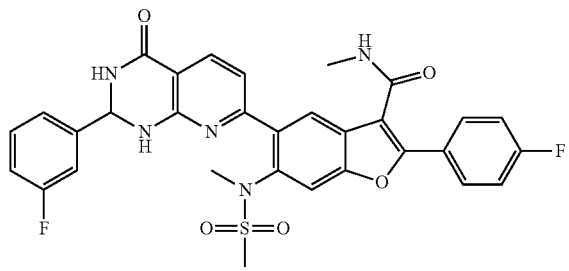 [SMILES: CNC(=O)c1c(-c2ccc(F)cc2)oc2cc(N(C)S(C)(=O)=O)c(-c3ccc4c(n3)NC(c3cccc(F)c3)NC4=O)cc12]

Step 1—Synthesis of 2-amino-6-chloronicotinamide

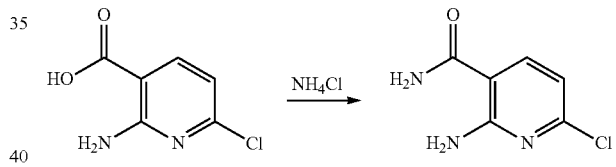

To a solution of 2-amino-6-chloronicotinic acid (1.0 g, 5.79 mmol), HOBT (932 mg, 6.95 mmol) and EDCI (2.22 g, 11.6 mmol) in 15 mL of DMF was added triethylamine (5.86 g, 57.9 mmol) and NH$_4$Cl (1.55 g, 28.9 mmol). Then the mixture was stirred at room temperature for 16 h. The solution was concentrated in vacuo to remove DMF and the residue was suspended in saturated NaHCO$_3$ Finally the 2-amino-6-chloronicotinamide (800 mg, yield: 81%) was obtained by filtration without further purification. $^1$H-NMR (DMSO-d$_6$, 400 MHz) δ 7.95 (d, J=8.4 Hz, 1H), 7.62 (s, 2H), 7.39 (s, 2H), 6.59 (d, J=8.4 Hz, 1H). MS (M+H)$^+$: 172/174.

Step 2—Synthesis of 7-chloro-2-(3-fluorophenyl)-2,3-dihydropyrido[2,3-d]pyrimidin-4(1H)-one

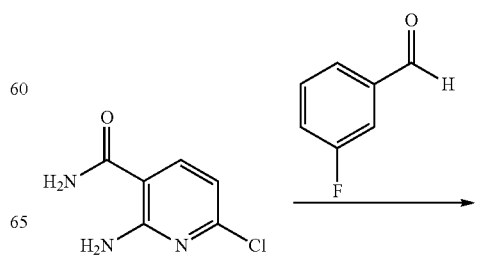

-continued

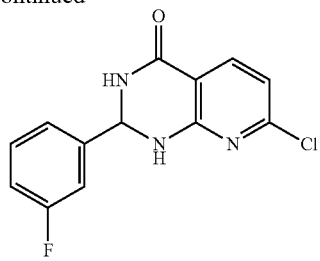

To a solution of 2-amino-6-chloronicotinamide (200 mg, 1.17 mmol) and 3-fluorobenzaldehyde (160 mg, 1.29 mmol) in 20 mL of EtOH was added PTSA (20 mg, 0.12 mmol), and then the mixture was heated at reflux for 16 h. The solution was cooled to room temperature and filtered to give the product of 7-chloro-2-(3-fluorophenyl)-2,3-dihydropyrido[2,3-d]pyrimidin-4(1H)-one (170 mg, yield: 52%) without further purification. $^1$H-NMR (CDCl$_3$, 400 MHz) δ 8.09 (d, J=8.0 Hz, 1H), 7.41~7.44 (m, 1H), 7.29~7.36 (m, 2H), 7.15~7.19 (m, 1H), 6.84 (d, J=8.0 Hz, 1H), 6.03 (s, 1H), 5.75 (s, 1H), 5.35 (s, 1H). MS (M+H)$^+$: 278/280.

Step 3—Synthesis of 2-(4-fluorophenyl)-5-(2-(3-fluorophenyl)-4-oxo-1,2,3,4-tetrahydropyrido[2,3-d]pyrimidin-7-yl)-N-methyl-6-(N-methylmethylsulfonamido)benzofuran-3-carboxamide To a solution of 7-chloro-2-(3-fluorophenyl)-2,3-dihydropyrido[2,3-d]pyrimidin-4(1H)-one (66 mg, 0.237 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (100 mg, 0.199 mmol) and K$_3$PO$_4$.3H$_2$O (106 mg, 0.398 mmol) in 1 mL of dioxane and 0.1 mL of water were added X-phos (10 mg) and Pd$_2$(dba)$_3$ (10 mg) under nitrogen. The mixture was heated at 100° C. for 6 h, concentrated in vacuo and the residue was suspended in water. The mixture was extracted with EtOAc and the organic phase was washed with brine, then dried over sodium sulfate. 2-(4-fluorophenyl)-5-(2-(3-fluorophenyl)-4-oxo-1,2,3,4-tetrahydropyrido[2,3-d]pyrimidin-7-yl)-N-methyl-6-(N-methylmethylsulfonamido)benzofuran-3-carboxamide (60 mg, yield: 49%) was obtained by the prep-TLC (PE:EtOAc=1:2). $^1$H-NMR (CD$_3$OD, 400 MHz) δ 8.06 (d, J=7.6 Hz, 1H), 7.91~7.95 (m, 2H), 7.81 (s, 1H), 7.77 (s, 1H), 7.37~7.40 (m, 1H), 7.32 (d, J=8.0 Hz, 1H), 7.21~7.27 (m, 3H), 7.02~7.08 (m, 2H), 5.96 (s, 1H), 3.27 (d, J=6.0 Hz, 3H), 2.90 (s, 3H), 2.80 (s, 3H). MS (M+H)$^+$: 618.

Example 19

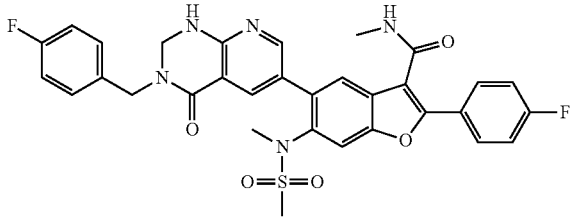 [SMILES: CNC(=O)c1c(-c2ccc(F)cc2)oc2cc(N(C)S(C)(=O)=O)c(-c3cnc4c(c3)C(=O)N(Cc3ccc(F)cc3)CN4)cc12]

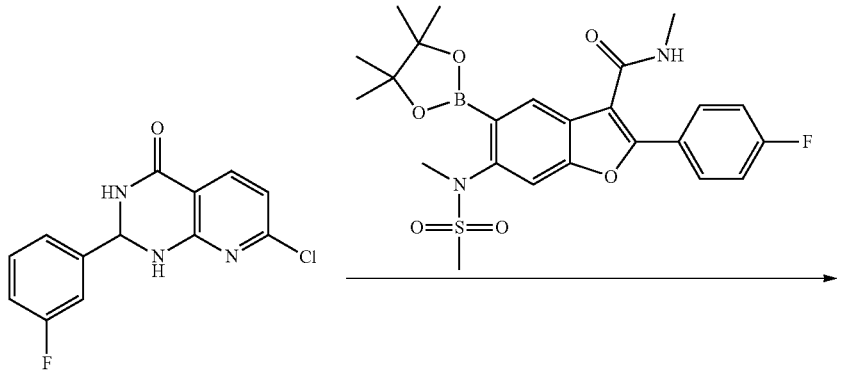

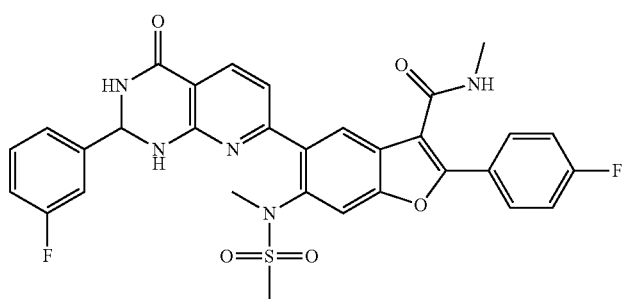

Step 1—Synthesis of 2-amino-5-bromo-N-(4-fluorobenzyl)nicotinamide

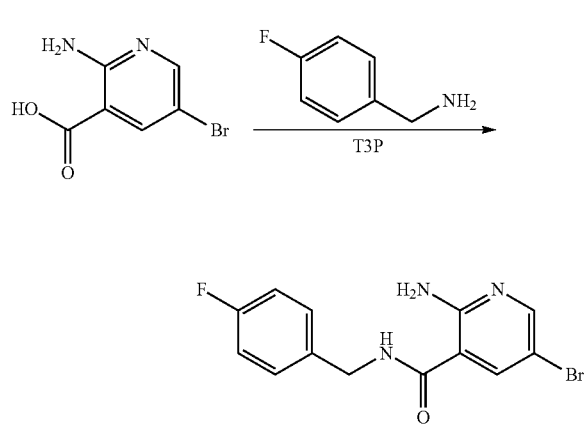

To a degassed solution of (4-fluorophenyl)methanamine (500 mg, 4.0 mmol), 2-amino-5-bromonicotinic acid (867 mg, 4.0 mmol) and Et$_3$N (1.21 g, 12.0 mmol) in dry DCM (10 mL) was added T3P (2.54 g, 8.0 mmol) at 0° C. under N$_2$ protection. The mixture was stirred at 0° C. for 20 minutes. The mixture was diluted with water, and then it was extracted with EtOAc, dried over Na$_2$SO$_4$, filtrated and concentrated to give the crude product of 2-amino-5-bromo-N-(4-fluorobenzyl)nicotinamide (1.05 g, yield: 81%). $^1$H-NMR (CDCl$_3$, 400 MHz) δ 8.18 (s, 1H), 7.64 (d, J=2.0 Hz, 1H), 7.31 (t, J=8.0 Hz, 2H), 7.05 (d, J=8.8 Hz, 2H), 6.38 (d, J=4.0 Hz, 2H), 6.17 (d, J=5.2 Hz, 1H), 5.12 (d, J=6.4 Hz, 2H). MS (M+H)$^+$: 324/326.

Step 2—Synthesis of 6-bromo-3-(4-fluorobenzyl)-2,3-dihydropyrido[2,3-d]pyrimidin-4(1H)-one

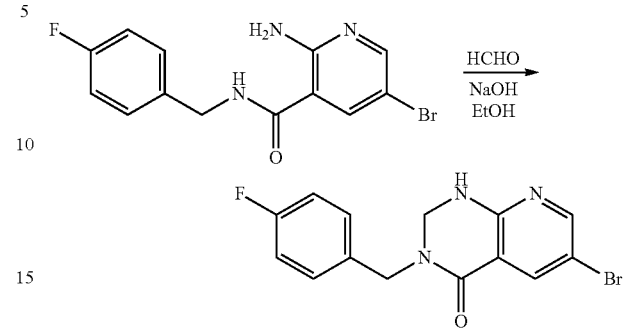

To a solution of 2-amino-5-bromo-N-(4-fluorobenzyl)nicotinamide (200 mg, 0.62 mmol) and NaOH (50 mg, 1.23 mmol) in 10 mL of EtOH was added HCHO (1 mL, 37% in water) and then the mixture was heated at reflux for 30 minutes. After being concentrated in vacuo, the residue was suspended in water and extracted with EtOAc. The organic phase was washed with brine, dried over sodium sulfate and concentrated in vacuo to give the crude product of 6-bromo-3-(4-fluorobenzyl)-2,3-dihydropyrido[2,3-d]pyrimidin-4(1H)-one (180 mg, yield: 87%) without further purification. $^1$H-NMR (CDCl$_3$, 400 MHz) δ 8.28~8.32 (m, 2H), 7.26~7.31 (m, 2H), 7.02 (t, J=8.4 Hz, 2H), 5.01 (s, 2H), 4.68 (d, J=2.4 Hz, 2H). MS (M+H)$^+$: 336/338.

Step 3—Synthesis of 5-(3-(4-fluorobenzyl)-4-oxo-1,2,3,4-tetrahydropyrido[2,3-d]pyrimidin-6-yl)-2-(4-fluorophenyl)-N-methyl-6-(N-methylmethylsulfonamido)benzofuran-3-carboxamide

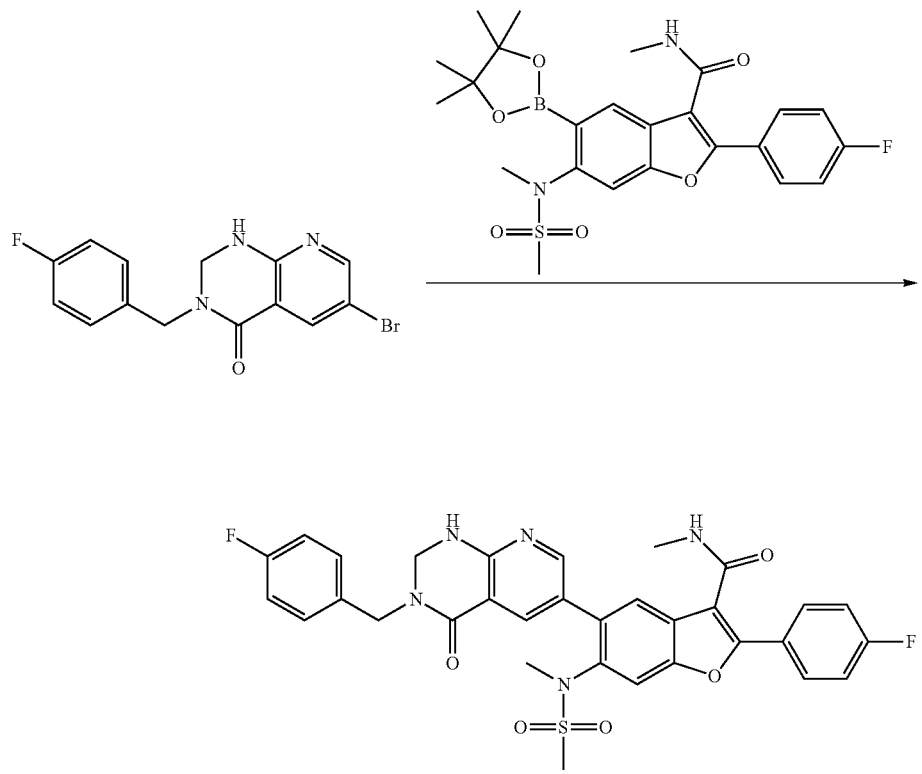

To a solution of 6-bromo-3-(4-fluorobenzyl)-2,3-dihydropyrido[2,3-d]pyrimidin-4(1H)-one (110 mg, 0.33 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (150 mg, 0.30 mmol) and K$_3$PO$_4$.3H$_2$O (159 mg, 0.60 mmol) in dioxane/water (2 mL/0.2 mL) was added Pd(dppf)Cl$_2$ (10 mg) under nitrogen. The mixture was heated at 100° C. for 5 h, and after being concentrated in vacuo, the residue was suspended in water. The suspension was extracted with EtOAc and the organic phase was washed with brine and dried over sodium sulfate. Finally, 5-(3-(4-fluorobenzyl)-4-oxo-1,2,3,4-tetrahydropyrido[2,3-d]pyrimidin-6-yl)-2-(4-fluorophenyl)-N-methyl-6-(N-methylmethylsulfonamido)benzofuran-3-carboxamide (80 mg, yield: 42%) was obtained by the prep-HPLC. $^1$H-NMR (CDCl$_3$, 400 MHz) δ 8.27~9.00 (m, 2H), 7.93~7.96 (m, 2H), 7.80 (s, 1H), 7.64 (s, 1H), 7.33~7.36 (m, 2H), 7.20 (t, J=8.8 Hz, 2H), 7.05 (t, J=8.4 Hz, 2H), 5.85 (br s, 1H), 5.26 (br s, 1H), 4.72 (s, 4H), 3.19 (s, 3H), 3.02 (d, J=4.8 Hz, 3H), 2.87 (s, 3H). MS (M+H)$^+$: 632.

Example 20

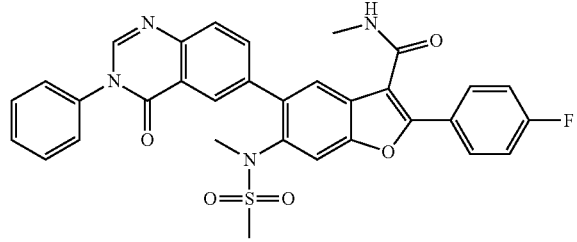 [SMILES: CNC(=O)c1c(-c2ccc(F)cc2)oc2cc(N(C)S(C)(=O)=O)c(-c3ccc4ncn(-c5ccccc5)c(=O)c4c3)cc12]

Step 1—Synthesis of 2-amino-5-bromo-N-phenylbenzamide

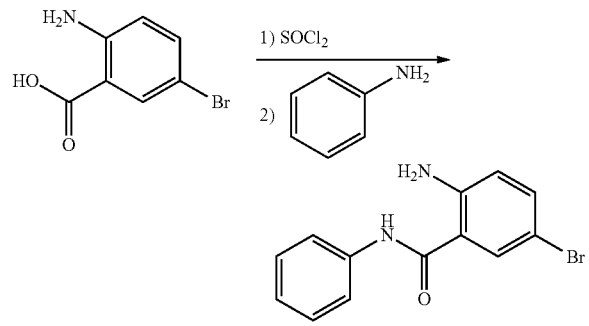

A mixture of 2-amino-5-bromo-benzoic acid (2 g, 9.26 mmol) and SOCl$_2$ (4 mL) in toluene (20 mL) was stirred at 130° C. for 2 h. After being concentrated, the residue was dissolved in tetrahydrofuran (50 mL) and phenylamine was added dropwise at 0° C. Then the reaction mixture was heated to 90° C. for 4 h. The mixture was cooled to room temperature, quenched with saturated aqueous K$_2$CO$_3$ (20 mL) and extracted with ethyl acetate (50 mL*3), the combined organic layers were washed with brine, dried over anhydrous sodium sulfate, filtered and concentrated. The residue was purified with silica gel column chromatograph (PE:EtOAc=4:1) to give 2-amino-5-bromo-N-phenylbenzamide (2.82 g, yield: 99%) as white solid. MS (M+H)$^+$: 291/293.

Step 2—Synthesis of 6-bromo-3-phenylquinazolin-4(3H)-one

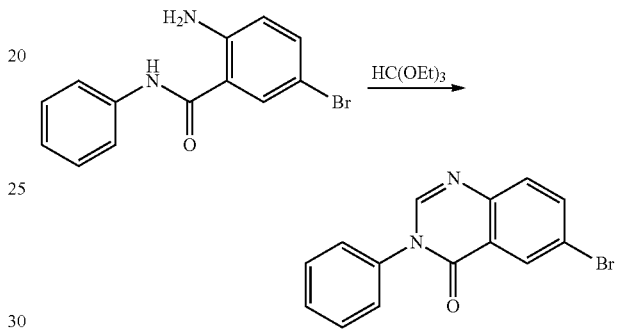

A mixture of 2-amino-5-bromo-N-phenylbenzamide (2.82 g, 9.7 mmol) and triethyl orthoformate (20 mL) was stirred at 130° C. for 15 h. The reaction mixture was cooled to RT and petroleum ether was added. After filtration, the filtrate was extracted with ethyl acetate (100 mL*3), the combined organic layers were washed with brine, dried over anhydrous sodium sulfate, filtered and concentrated. The residue was purified with silica gel column chromatograph (PE:EtOAc=5:1) to give 6-bromo-3-phenylquinazolin-4(3H)-one (1.5 g, yield: 50%) as white solid. $^1$H-NMR (CDCl$_3$, 400 MHz) δ 8.50 (d, J=2.4 Hz, 1H), 8.13 (s, 1H), 7.87~7.90 (m, 1H), 7.65 (d, J=8.8 Hz, 1H), 7.55~7.58 (m, 2H), 7.51~7.53 (m, 1H), 7.41~7.43 (m, 2H). MS (M+H)$^+$:301/303.

Step 3—Synthesis of 2-(4-fluorophenyl)-N-methyl-6-(N-methylmethylsulfonamido)-5-(4-oxo-3-phenyl-3,4-dihydroquinazolin-6-yl)benzofuran-3-carboxamide

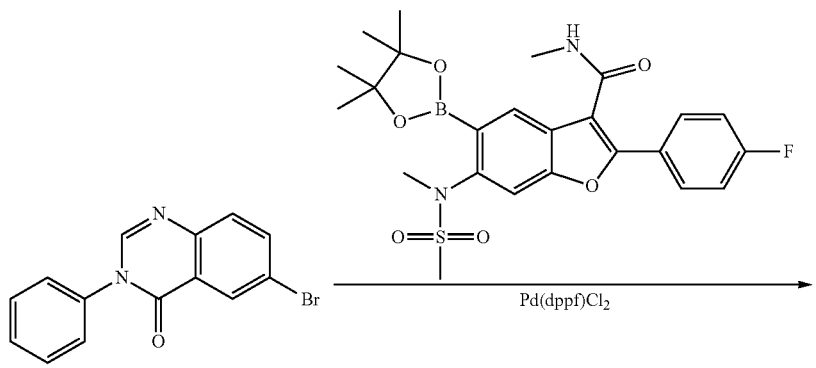

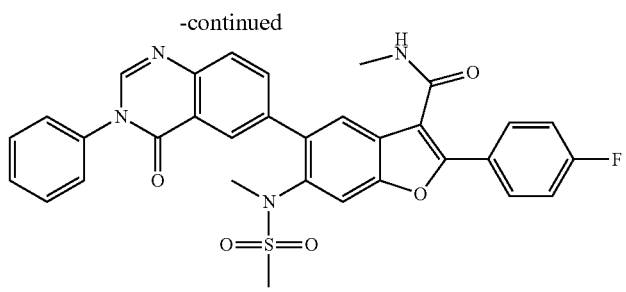

To a degassed mixture of 6-bromo-3-phenylquinazolin-4 (3H)-one (150 mg, 0.498 mmol) and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (100 mg, 0.199 mmol) in N,N-dimethyl-formamide (4 mL) were added Pd(dppf)Cl$_2$ (15 mg) and K$_3$PO$_4$ (211 mg, 0.994 mmol) under N$_2$. After being heated to 90° C. overnight, the reaction mixture was cooled to RT and filtered. The filtrate was concentrated and the residue was purified by prep-HPLC to give the product of 2-(4-fluorophenyl)-N-methyl-6-(N-methylmethylsulfonamido)-5-(4-oxo-3-phenyl-3,4-dihydroquinazolin-6-yl)benzofuran-3-carboxamide (10.28 mg, yield: 10%). $^1$H-NMR (CDCl$_3$, 400 MHz) δ 8.41 (d, J=2.0 Hz, 1H), 8.31 (s, 1H), 7.99~7.92 (m, 3H), 7.88 (t, J=3.6 Hz, 2H), 7.64 (s, 1H), 7.60~7.52 (m, 3H), 7.46 (d, J=7.2 Hz, 2H), 7.21 (t, J=8.8 Hz, 2H), 5.96 (d, J=4.8 Hz, 1H), 3.18 (s, 3H), 3.00 (d, J=5.2 Hz, 3H), 2.79 (s, 3H). MS (M+H)$^+$: 597.

Example 21

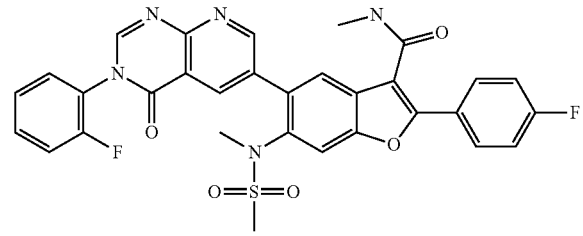 [SMILES: CNC(=O)c1c(-c2ccc(F)cc2)oc2cc(N(C)S(C)(=O)=O)c(-c3cnc4ncn(-c5ccccc5F)c(=O)c4c3)cc12]

Step 1—Synthesis of 2-amino-5-bromonicotinic acid

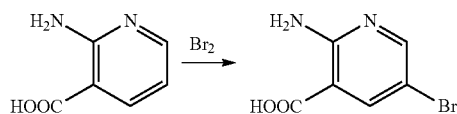

2-Amino-nicotinic acid (2 g, 14.48 mmol) was dispersed in glacial acetic acid. To this suspension was added a solution of bromine (1.2 mL) in glacial acetic acid (5 mL). The mixture was stirred at room temperature for 20 h. The mixture was filtered and washed with glacial acetic acid (10 mL) and water in several portions. The precipitate was collected and dried to give 2-amino-5-bromonicotinic acid (3.0 g, 95% yield) as yellow solid. $^1$H-NMR (DMSO-d$_6$, 400 MHz) δ 8.31 (d, J=2.4 Hz, 1H), 8.18 (d, J=2.8 Hz, 1H), 5.06~5.27 (m, 2H). MS (M+H)$^+$: 218/220.

Step 2—Synthesis of 2-amino-5-bromo-N-(2-fluorophenyl)nicotinamide

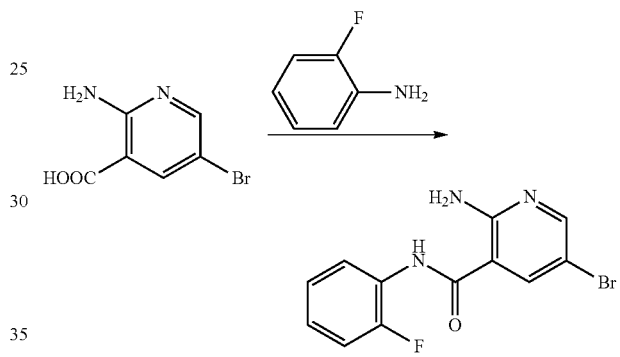

A mixture of 2-Amino-5-bromo-nicotinic acid (1 g, 4.61 mmol) and SOCl$_2$ (5 mL) in toluene (15 mL) was stirred at 130° C. for 2 h. After concentrated, the residue was dissolved in tetrahydrofuran (20 mL), and then 2-fluoro-phenylamine (1.09 g, 9.81 mmol) was added dropwise at 0° C. The reaction mixture was heated to 90° C. for 4 h. After being cooled to room temperature and quenched with saturated aqueous K$_2$CO$_3$ (10 mL), the mixture was extracted with ethyl acetate (50 mL*3). The combined organic layers were washed with brine, dried over anhydrous sodium sulfate, filtered and concentrated. The residue was purified with silica gel column chromatograph (PE:EtOAc=2:1) to give 2-amino-5-bromo-N-(2-fluorophenyl)nicotinamide (1.0 g, 70% yield) as yellow solid. $^1$H-NMR (CDCl$_3$, 400 MHz) δ 8.25~8.28 (m, 2H), 7.86 (d, J=2.4 Hz, 2H), 7.13~7.22 (m, 3H), 6.36 (s, 2H). MS (M+H)$^+$: 311/313.

Step 3—Synthesis of 6-bromo-3-(2-fluorophenyl) pyrido[2,3-d]pyrimidin-4(3H)-one

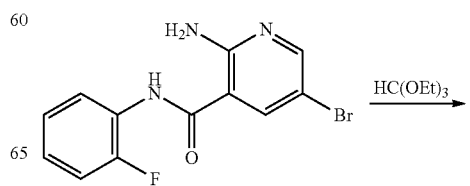

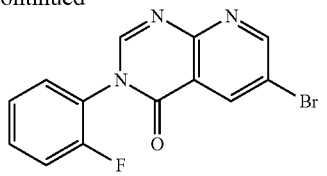

A mixture of 2-amino-5-bromo-N-(2-fluorophenyl)nicotinamide (100 mg, 0.32 mmol) and triethoxymethane (5 mL) was stirred at 130° C. for 15 h. The mixture was cooled to room temperature and extracted with ethyl acetate (10 mL*3), the combined organic layers were washed with brine, dried over anhydrous sodium sulfate, filtered and concentrated to afford 6-bromo-3-(2-fluorophenyl)pyrido[2,3-d]pyrimidin-4(3H)-one (100 mg, 97% yield), which was used for the next step without further purification. MS (M+H)$^+$:320/322.

Step 4—Synthesis of 2-(2,4-difluorophenyl)-N-methyl-6-(N-methylmethylsulfonamido)-5-(4,4,5,5-tetramethyl-1,3,2-dioxaborolan-2-yl)benzofuran-3-carboxamide To a degassed mixture of 6-bromo-3-(2-fluorophenyl)pyrido[2,3-d]pyrimidin-4(3H)-one (100 mg, 0.313 mmol), and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (100 mg, 0.199 mmol) in N, N-dimethyl-formamide (5 mL) were added Pd(dppf)Cl$_2$ (15 mg) and K$_3$PO$_4$ (135 mg, 0.637 mmol) under N$_2$. The mixture was heated to 80° C. overnight. The reaction mixture was cooled to RT and filtered. The filtrate was concentrated, and the residue was purified by prep-HPLC to give 2-(4-fluorophenyl)-5-(3-(2-fluorophenyl)-4-oxo-3,4-dihydropyrido[2,3-d]pyrimidin-6-yl)-N-methyl-6-(N-methylmethylsulfonamido)benzofuran-3-carboxamide (11.78 mg, yield: 10%). $^1$H-NMR (CDCl$_3$, 400 MHz) δ 9.12 (d, J=2.0 Hz, 1H), 8.77 (d, J=2.0 Hz, 1H), 8.33 (s, 1H), 7.94 (t, J=6.8 Hz, 3H), 7.68 (s, 1H), 7.54~7.59 (m, 1H), 7.47 (t, J=6.8 Hz, 1H), 7.33~7.39 (m, 2H), 7.21 (t, J=8.4 Hz, 2H), 6.04 (d, J=4.4 Hz, 1H), 3.27 (s, 3H), 3.01 (d, J=4.8 Hz, 3H), 2.83 (s, 3H). MS (M+H)$^+$: 616.

Examples 22~25, depicted in the table below, were prepared using the method described above.

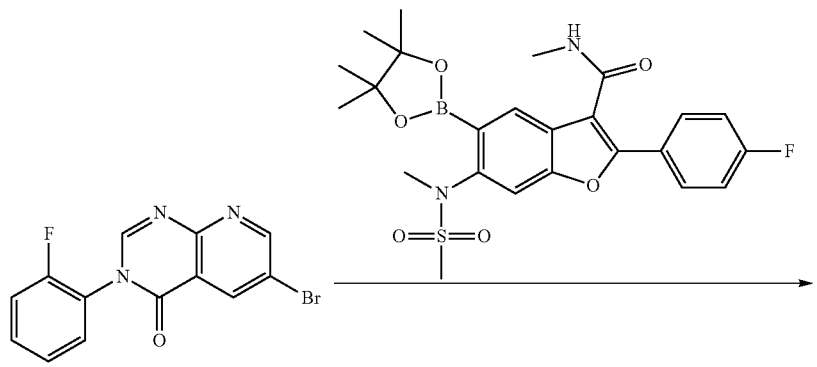

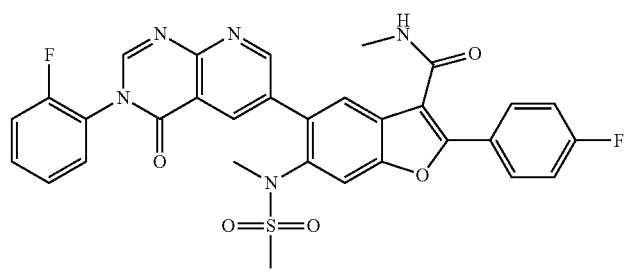

| Example | Structure | NMR | MS (M + H)+ |
|---|---|---|---|
| 22 | 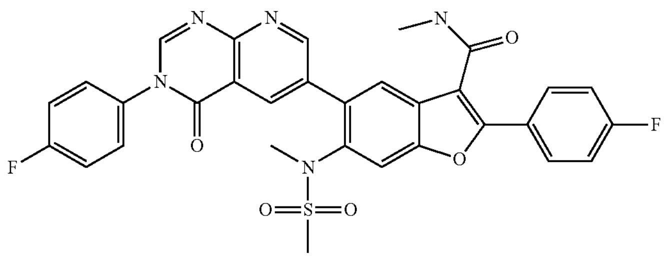 [SMILES: CNC(=O)c1c(-c2ccc(F)cc2)oc2cc(N(C)S(C)(=O)=O)c(-c3cnc4ncn(-c5ccc(F)cc5)c(=O)c4c3)cc12] | ¹H-NMR (CDCl₃, 400 MHz) δ 9.10 (s, 1H), 8.74 (s, 1H), 8.37 (s, 1H), 7.92~7.96 (m, 3H), 7.67 (s, 1H), 7.46 (s, 2H), 7.27 (s, 2H), 7.21 (t, J = 8.4 Hz, 2H), 6.04 (s, 1H), 3.26 (s, 3H), 3.01 (s, 3H), 2.83 (s, 3H). | 616 |
| 23 | 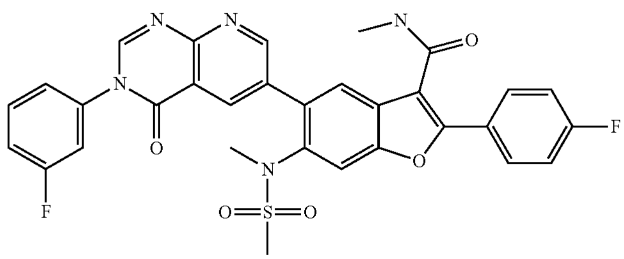 [SMILES: CNC(=O)c1c(-c2ccc(F)cc2)oc2cc(N(C)S(C)(=O)=O)c(-c3cnc4ncn(-c5cccc(F)c5)c(=O)c4c3)cc12] | ¹H-NMR (CDCl₃, 400 MHz) δ 9.14 (d, J = 2.0 Hz, 1H), 8.78 (d, J = 2.4 Hz, 1H), 8.41 (s, 1H), 7.92~7.97 (m, 3H), 7.68 (s, 1H), 7.55~7.61 (m, 1H), 7.28 (d, J = 7.6 Hz, 2H), 7.23 (t, J = 8.4 Hz, 3H), 5.92 (d, J = 4.4 Hz, 1H), 3.29 (s, 3H), 3.01 (d, J = 4.8 Hz, 3H), 2.84 (s, 3H). | 616 |
| 24 | 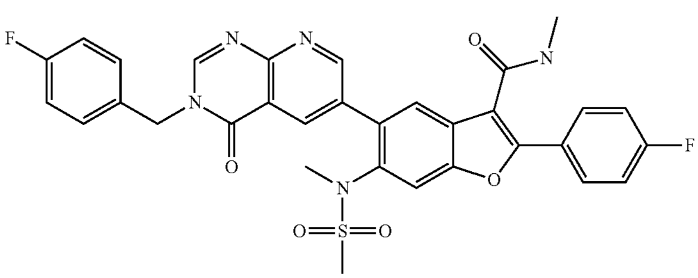 [SMILES: CNC(=O)c1c(-c2ccc(F)cc2)oc2cc(N(C)S(C)(=O)=O)c(-c3cnc4ncn(Cc5ccc(F)cc5)c(=O)c4c3)cc12] | ¹H-NMR (CDCl₃, 400 MHz) δ 8.91 (s, 1H), 8.62 (d, J = 2.4 Hz, 1H), 8.25 (s, 1H), 7.76~7.91 (m, 3H), 7.57 (s, 1H), 7.44~7.46 (m, 2H), 7.12 (t, J = 8.4 Hz, 2H), 7.01 (t, J = 8.8 Hz, 2H), 6.18~6.21 (m, 1H), 5.12 (s, 2H), 3.15 (s, 3H), 2.94 (d, J = 4.8 Hz, 3H), 2.73 (s, 3H). | 630 |
| 25 | 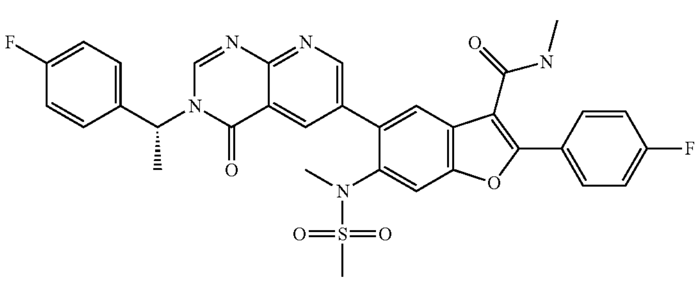 [SMILES: CNC(=O)c1c(-c2ccc(F)cc2)oc2cc(N(C)S(C)(=O)=O)c(-c3cnc4ncn([C@H](C)c5ccc(F)cc5)c(=O)c4c3)cc12] | ¹H-NMR (CDCl₃, 400 MHz) δ 8.99 (d, J = 2.4 Hz, 1H), 8.66 (d, J = 2.4 Hz, 1H), 8.14 (s, 1H), 7.85~7.90 (m, 3H), 7.61 (s, 1H), 7.32~7.37 (m, 2H), 7.13~7.16 (m, 2H), 7.05 (t, J = 8.8 Hz, 2H), 6.23 (q, J = 7.2 Hz, 1H), 6.85 (d, J = 5.6 Hz, 1H), 5.79 (br s, 1H), 3.17 (s, 3H), 2.94 (d, J = 4.8 Hz, 3H), 2.75 (s, 3H), 1.82 (d, J = 7.2 Hz, 3H). | 644 |

Example 26

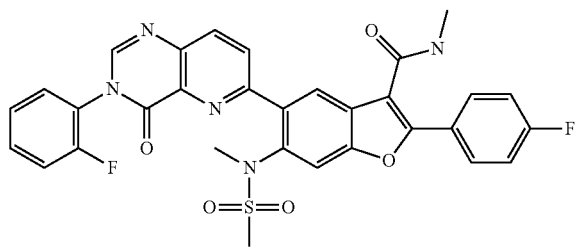 [SMILES: CNC(=O)c1c(-c2ccc(F)cc2)oc2cc(N(C)S(C)(=O)=O)c(-c3ccc4ncn(-c5ccccc5F)c(=O)c4n3)cc12]

Step 1—Synthesis of 3-amino-6-bromo-N-(2-fluorophenyl)picolinamide

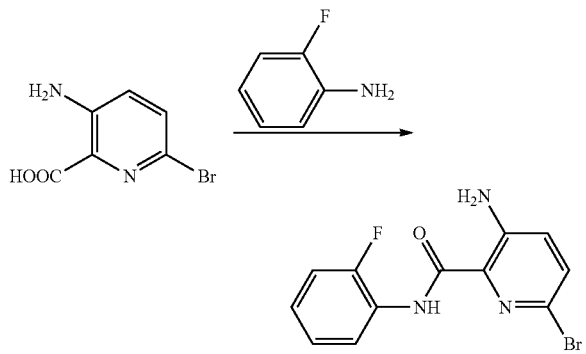

A mixture of 3-amino-6-bromopicolinic acid (250 mg, 1.152 mmol) and SOCl$_2$ (5 mL) in toluene (10 mL) was stirred at 130° C. for 2 h, then evaporated and dissolved in tetrahydrofuran (20 mL). 2-fluoro-phenylamine (256 mg, 2.3 mmol) was added dropwise maintaining the temperature at 5° C. The reaction mixture was heated to 90° C. for 15 h. The mixture was cooled to room temperature and quenched with saturated aqueous K$_2$CO$_3$ (10 mL) and extracted with ethyl acetate (10 mL*3), the combined organic layers were washed with brine, dried over anhydrous sodium sulfate, filtered and concentrated. The residue was purified with column chromatograph (PE:EtOAc=3:1) to give 3-amino-6-bromo-N-(2-fluorophenyl)picolinamide (160 mg, yield: 45%). MS (M+H)$^+$: 311/313.

Step 2—Synthesis of 6-bromo-3-(2-fluorophenyl)pyrido[3,2-d]pyrimidin-4(3H)-one

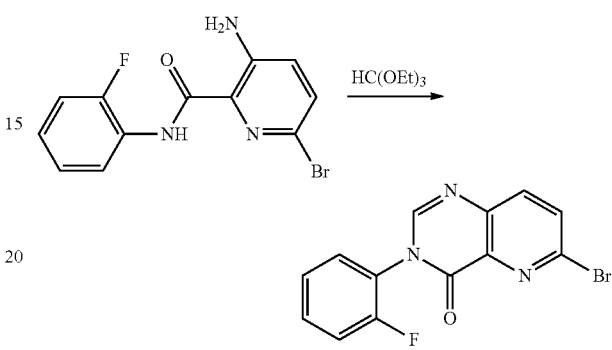

A mixture of 3-amino-6-bromo-N-(2-fluorophenyl)picolinamide (160 mg, 0.516 mmol) in triethoxymethane (5 mL) was stirred at 130° C. for 15 h. The mixture was cooled to room temperature and extracted with ethyl acetate (10 mL*3), the combined organic layers were washed with brine, dried over anhydrous sodium sulfate, filtered and concentrated to afford 6-bromo-3-(2-fluorophenyl)pyrido[3,2-d]pyrimidin-4(3H)-one (75 mg, yield: 45%), which was used for the next step without further purification. MS (M+H)$^+$:320/322

Step 3—Synthesis of 2-(4-fluorophenyl)-5-(3-(2-fluorophenyl)-4-oxo-3,4-dihydropyrido[3,2-d]pyrimidin-6-yl)-N-methyl-6-(N-methylmethylsulfonamido)benzofuran-3-carboxamide

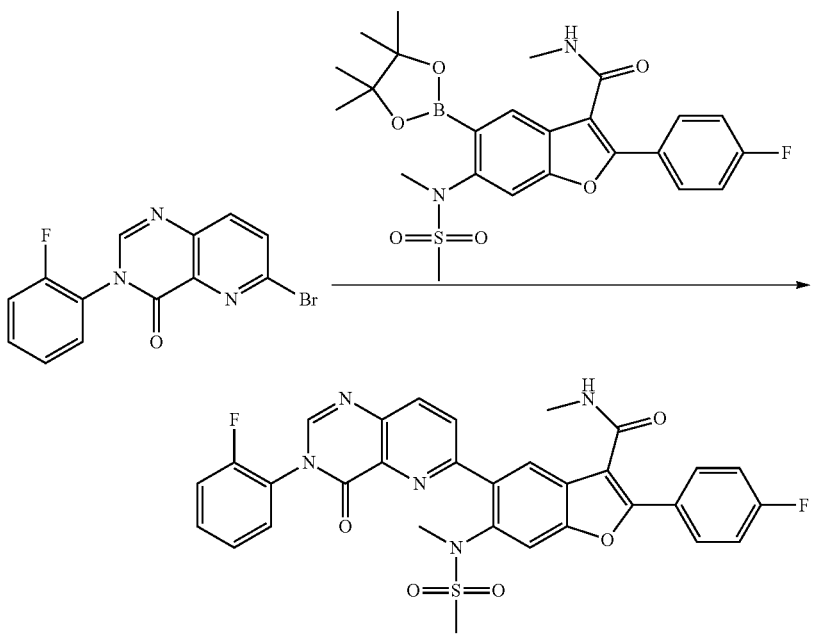

To a degassed mixture of 6-bromo-3-(2-fluorophenyl)pyrido[2,3-d]pyrimidin-4(3H)-one (75 mg, 0.234 mmol) and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (100 mg, 0.199 mmol) in N,N-dimethyl-formamide (5 mL) were added Pd(dppf)Cl$_2$ (15 mg) and K$_3$PO$_4$ (127 mg, 0.468 mmol) under N$_2$. The mixture was heated to 80° C. overnight. The reaction mixture was cooled to room temperature and filtered. The filtrate was concentrated, and the residue was purified by prep-HPLC to give 2-(4-fluorophenyl)-5-(3-(2-fluorophenyl)-4-oxo-3,4-dihydropyrido[3,2-d]pyrimidin-6-yl)-N-methyl-6-(N-methylmethylsulfonamido)benzofuran-3-carboxamide (30 mg, yield: 30%). $^1$H-NMR (CDCl$_3$, 400 MHz) δ 8.22 (d, J=8.8 Hz, 1H), 8.08~8.14 (m, 3H), 7.96~7.99 (m, 2H), 7.65 (s, 1H), 7.47~7.57 (m, 2H), 7.32~7.38 (m, 2H), 7.19 (t, J=8.8 Hz, 2H), 6.47 (br s, 1H), 3.27 (s, 3H), 2.98 (d, J=4.8 Hz, 3H), 2.93 (s, 3H). MS (M+H)$^+$: 616.

Example 27

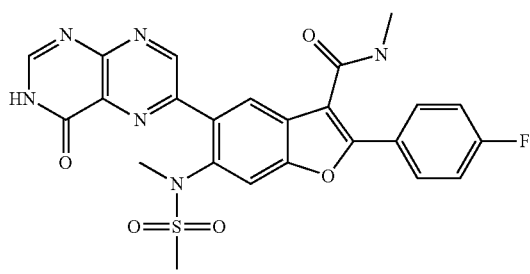 [SMILES: CNC(=O)c1c(-c2ccc(F)cc2)oc2cc(N(C)S(C)(=O)=O)c(-c3cnc4nc[nH]c(=O)c4n3)cc12]

Step 1—Synthesis of 3-amino-6-bromopyrazine-2-carboxamide

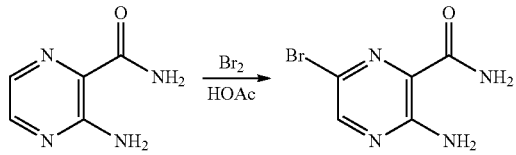

To a stirred solution of 3-aminopyrazine-2-carboxamide (1 g, 7.24 mmol, prepared according to International Patent Application Publication No. WO2011054922) and NaOAc (200 mg, 2.44 mmol) in HOAc (15 mL) was added Br$_2$ (0.45 mL) dropwise at 0° C. for 1 hour, and then it was stirred at 50° C. for 8 hours. After the mixing, it was poured into ice-water and filtrated, the crude product of 3-amino-6-bromopyrazine-2-carboxamide as brown solid (1.5 g, yield: 95%) was obtained. $^1$H-NMR (DMSO-d$_6$, 400 MHz) δ 8.30 (s, 1H), 7.93 (s, 2H), 7.66 (s, 2H). MS (M+H)$^+$: 217/219.

Step 2—Synthesis of 6-bromopteridin-4(3H)-one

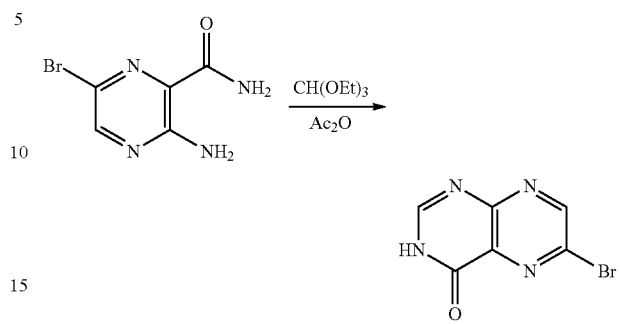

To a solution of 3-amino-6-bromopyrazine-2-carboxamide (200 mg, 0.92 mmol) in triethoxymethane (10 mL) was added Ac$_2$O (2 mL). The mixture was stirred at 130° C. for 1 h and 90° C. for 3 h. After being cooled to RT and extracted with EtOAc, the combined organic phases were basified to pH=8 with a.q. NaHCO$_3$, washed with brine, dried over Na$_2$SO$_4$, filtered and evaporated. The crude product was purified by prep-TLC (DCM:MeOH=50:1) to give the product of 6-bromopteridin-4(3H)-one (100 mg, yield: 48%). $^1$H-NMR (DMSO-d$_6$, 400 MHz) δ 8.59 (s, 1H), 7.89 (s, 1H). MS (M+H)$^+$: 227/229.

Step 3—Synthesis of 2-(4-fluorophenyl)-N-methyl-6-(N-methylmethylsulfonamido)-5-(4-oxo-3,4-dihydropteridin-6-yl)benzofuran-3-carboxamide

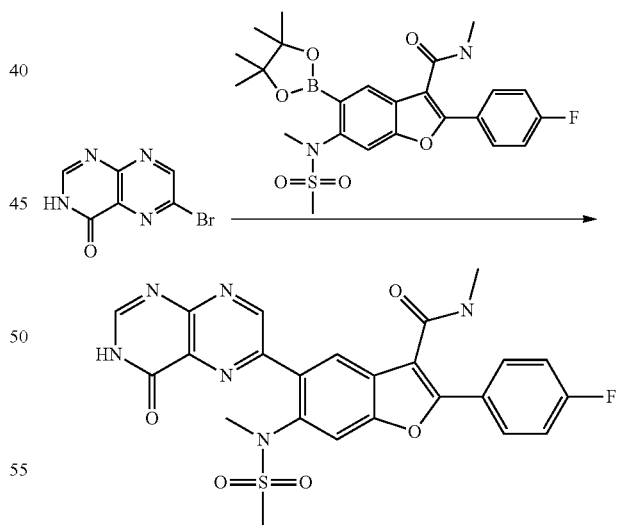

To a stirring mixture of ethyl 6-bromopteridin-4(3H)-one (50 mg, 0.22 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (110 mg, 0.22 mmol) and Na$_2$CO$_3$ (35 mg, 0.33 mmol) in dioxane/H$_2$O (2 mL/0.2 mL) was added Pd(dppf)Cl$_2$ (10 mg) under N$_2$ protection. The mixture was stirred at 100° C. overnight. The mixture was concentrated in vacuo and extracted with EtOAc.

After the organic layer was washed with brine, dried over Na₂SO₄, filtered and evaporated, the crude product was purified by prep-HPLC to give the product of 2-(4-fluorophenyl)-N-methyl-6-(N-methylmethylsulfonamido)-5-(4-oxo-3,4-dihydropteridin-6-yl)benzofuran-3-carboxamide (30 mg, yield: 26%). ¹H-NMR (DMSO-d₆, 400 MHz) δ 9.19 (s, 1H), 8.61 (d, J=4.8 Hz, 1H), 8.39 (s, 1H), 8.19 (s, 1H), 7.97~7.99 (m, 3H), 7.42 (t, J=8.4 Hz, 2H), 3.37 (s, 3H), 3.00 (s, 3H), 2.83 (d, J=4.0 Hz, 3H). MS (M+H)⁺: 523.

Example 28

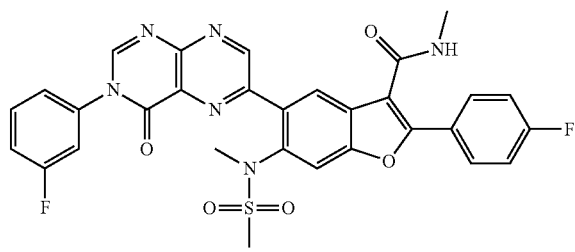 [SMILES: CNC(=O)c1c(-c2ccc(F)cc2)oc2cc(N(C)S(C)(=O)=O)c(-c3cnc4ncn(-c5cccc(F)c5)c(=O)c4n3)cc12]

Step 1—Synthesis of methyl 3-amino-6-bromopyrazine-2-carboxylate

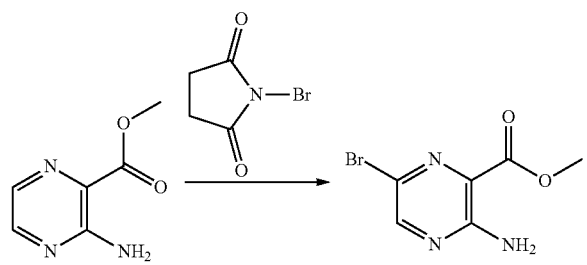

A solution of methyl 3-aminopyrazine-2-carboxylate (3.0 g, 19.6 mmol) and NBS (3.5 g, 23.5 mol) in MeCN (70 mL) was stirred at 70° C. for 5 h. Then the mixture was concentrated and extracted with EtOAc. The organic layer was washed with Na₂SO₃ (a.q.) and brine, dried over Na₂SO₄ and concentrated in vacuo. The crude product of methyl 3-amino-6-bromopyrazine-2-carboxylate (3.0 g, yield: 92%) was used for next step without further purification. ¹H-NMR (CDCl₃, 400 MHz) δ 8.18 (s, 1H), 6.54~6.93 (m, 2H), 3.86 (s, 3H). MS (M+H)⁺: 232/234.

Step 2—Synthesis of 3-amino-6-bromopyrazine-2-carboxylic acid

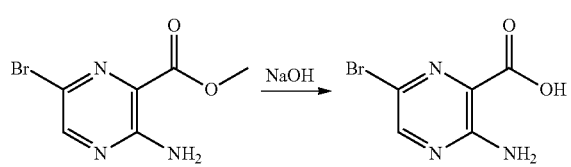

To a solution of methyl 3-amino-6-bromopyrazine-2-carboxylate (100 mg, 0.43 mmol) in MeOH (5 mL) was added 2 mL of NaOH aqueous solution (5 N). After being stirred at 50° C. for 4 h, the mixture was cooled and acidified with 1 M HCl to a pH of 2. The precipitate was collected by filtration and washed with water to afford the product of 3-amino-6-bromopyrazine-2-carboxylic acid (90 mg, yield: 96%). ¹H-NMR (DMSO-d₆, 400 MHz) δ 8.38 (s, 1H), 7.51~7.56 (m, 2H). MS (M+H)⁺: 218/220.

Step 3—Synthesis of 3-amino-6-bromo-N-(3-fluorophenyl)pyrazine-2-carboxamide

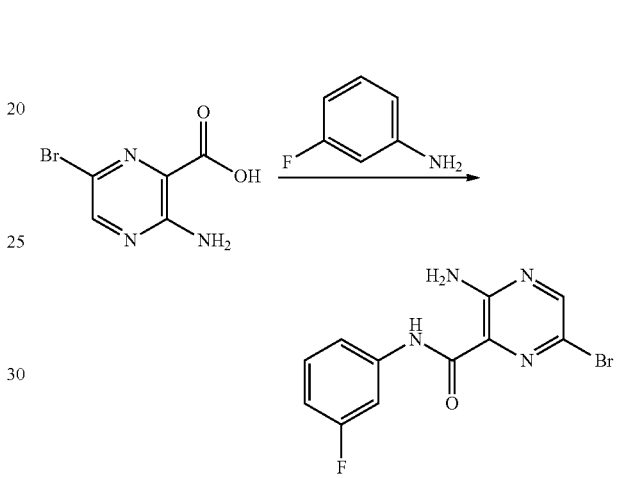

3-amino-6-bromopyrazine-2-carboxylic acid (500 mg, 2.29 mmol), HOBT (464 mg, 3.44 mmol) and EDCI (660 mg, 3.44 mmol) were dissolved in dry DMF (20 mL), and the resulting solution was stirred for 6 hours. Then 3-fluoroaniline (305 mg, 2.75 mmol) and Et₃N (0.43 mL) was added to the mixture. After being stirred overnight, the mixture was diluted with water and extracted with EtOAc. The combined organic phases were washed with brine, dried over Na₂SO₄, filtered and evaporated. The crude product was purified by prep-TLC (PE:EtOAc=6:1) to give the pure product of 3-amino-6-bromo-N-(3-fluorophenyl)pyrazine-2-carboxamide (500 mg, yield: 68%). ¹H-NMR (CDCl₃, 400 MHz) δ 9.44 (s, 1H), 8.22 (s, 1H), 7.59 (d, J=11.2 Hz, 1H), 7.24~7.27 (m, 2H), 6.79~6.82 (m, 1H), 3.21 (s, 2H). MS (M+H)⁺: 311/313.

Step 4—Synthesis of 6-bromo-3-(3-fluorophenyl)pteridin-4(3H)-one

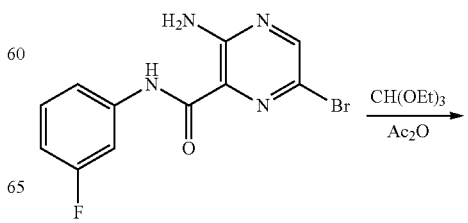

-continued

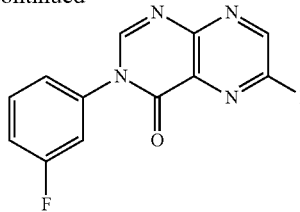

To a solution of 3-amino-6-bromo-N-(3-fluorophenyl)pyrazine-2-carboxamide (100 mg, 0.29 mmol) in triethoxymethane (5 mL) was added Ac$_2$O (1 mL). The mixture was stirred at 130° C. for 1 h and 90° C. for 3 h. After being cooled and extracted with EtOAc, the combined organic phases were washed with brine, dried over Na$_2$SO$_4$, filtered and evaporated. The crude product was purified by prep-TLC (PE:EtOAc=1:1) to give the pure product of 6-bromo-3-(3-fluorophenyl)pteridin-4(3H)-one (60 mg, yield: 60%). $^1$H-NMR (CDCl$_3$, 400 MHz) δ 8.98 (s, 1H), 8.35 (s, 1H), 7.49~7.55 (m, 1H), 7.15~7.24 (m, 3H). MS (M+H)$^+$: 321/323.

Step 5—Synthesis of 2-(4-fluorophenyl)-5-(3-(3-fluorophenyl)-4-oxo-3,4-dihydropteridin-6-yl)-N-methyl-6-(N-methylmethylsulfonamido)benzofuran-3-carboxamide To a stirring mixture of 6-bromo-3-(3-fluorophenyl)pteridin-4(3H)-one (32 mg, 0.099 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (50 mg, 0.099 mmol) and Na$_2$CO$_3$ (18 mg, 0.199 mmol) in dioxane/H$_2$O (1 mL/0.1 mL) was added Pd(dppf)Cl$_2$ (10 mg) under N$_2$ protection. The mixture was stirred in a pre-heated oil-bath at 120° C. for 5 h. The mixture was cooled and extracted with EtOAc. The combined organic phases were washed with brine, dried over Na$_2$SO$_4$, filtered and evaporated. The crude product was purified by prep-HPLC to give the pure product of 2-(4-fluorophenyl)-5-(3-(3-fluorophenyl)-4-oxo-3,4-dihydropteridin-6-yl)-N-methyl-6-(N-methylmethylsulfonamido)benzofuran-3-carboxamide (40 mg, yield: 50%). $^1$H-NMR (CDCl$_3$, 400 MHz) δ 9.20 (s, 1H), 8.36 (s, 1H), 8.13 (s, 1H), 7.87~7.92 (m, 2H), 7.63 (s, 1H), 7.43~7.55 (m, 1H), 7.33~7.38 (m, 1H), 7.13~7.25 (m, 4H), 6.07 (br s, 1H), 3.30 (s, 3H), 2.94 (d, J=4.8 Hz, 3H), 2.86 (s, 3H). MS (M+H)$^+$: 617.

Example 29

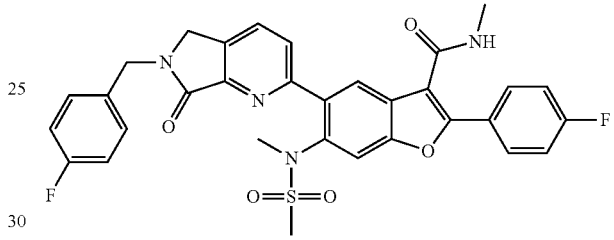

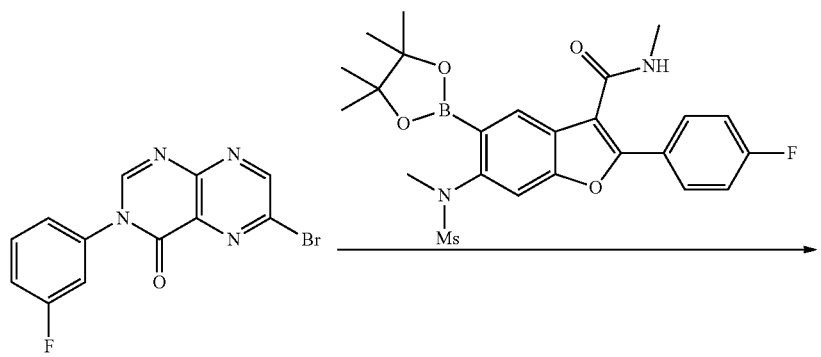

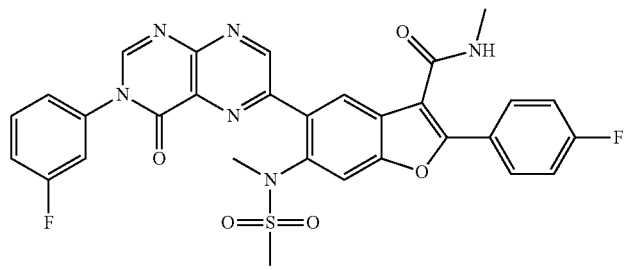

Step 1—Synthesis of 2-(methoxycarbonyl)-3-methylpyridine 1-oxide

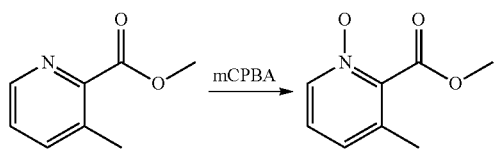

A mixture of methyl 3-methylpicolinate (2 g, 14.8 mmol) and m-CPBA (3 g, 17.8 mmol) in DCM (35 mL) was stirred at RT overnight. Then the mixture was washed with NaHSO$_3$ (a.q.) and concentrated in vacuum. The residue was purified by column chromatography (DCM:MeOH=200:1) to give the product of 2-(methoxycarbonyl)-3-methylpyridine 1-oxide (1.89 g, yield: 79%). $^1$H-NMR (CDCl$_3$, 400 MHz) δ 8.05 (d, J=6.0 Hz, 1H), 7.18 (t, J=8.4 Hz, 1H), 7.10 (d, J=8.0 Hz, 1H), 3.95 (s, 3H), 2.23 (s, 3H). MS (M+H)$^+$: 168.

Step 2—Synthesis of methyl 6-chloro-3-methylpicolinate

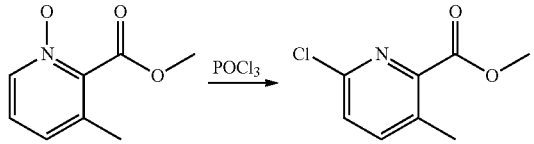

A solution of 2-(methoxycarbonyl)-3-methylpyridine 1-oxide (2 g, 6.0 mmol) in POCl$_3$ (5 mL) was stirred at 100° C. for 3 hours. After being concentrated, the residue was purified by column chromatography (PE:EtOAc=1:1) to give the product of methyl 6-chloro-3-methylpicolinate (380 mg, yield: 37%). $^1$H-NMR (CDCl$_3$, 400 MHz) δ 7.59 (d, J=8.0 Hz, 1H), 7.38 (d, J=8.0 Hz, 1H), 3.96 (s, 3H), 2.56 (s, 3H). MS (M+H)$^+$: 186/188.

Step 3—Synthesis of methyl 3-(bromomethyl)-6-chloropicolinate

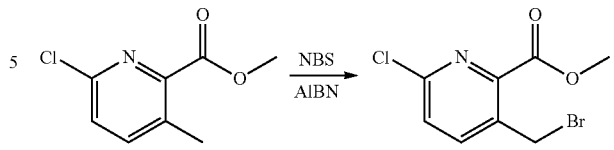

A solution of 6-chloro-3-methylpicolinate (100 mg, 0.58 mmol), NBS (104 mg, 0.58 mmol) and AIBN (2 mg, 11 μmol) in CCl$_4$ (10 mL) was stirred at 80° C. overnight. After reaction, the mixture was concentrated and the residue was purified by prep-TLC (PE:EtOAc=5:1) to give the product of methyl 3-(bromomethyl)-6-chloropicolinate (100 mg, yield: 65%). $^1$H-NMR (CDCl$_3$, 400 MHz) δ 7.85 (d, J=8.0 Hz, 1H), 7.49 (d, J=8.0 Hz, 1H), 4.81 (s, 2H), 4.01 (s, 3H). MS (M+H)$^+$: 264/266/268.

Step 4—Synthesis of 2-chloro-6-(4-fluorobenzyl)-5H-pyrrolo[3,4-b]pyridin-7(6H)-one

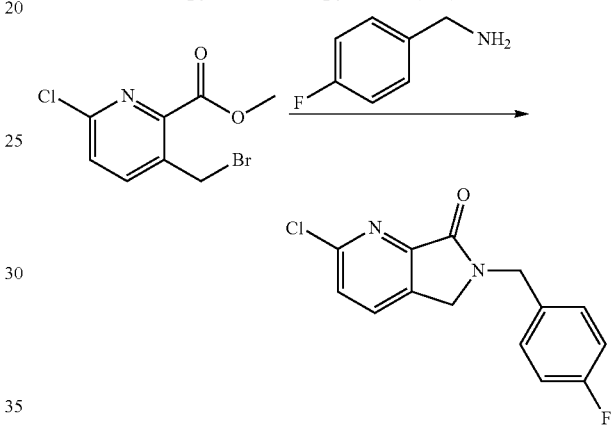

A solution of methyl 3-(bromomethyl)-6-chloropicolinate (100 mg, 0.38 mmol) and 4-fluorobenzylamine (237 mg, 1.89 mmol) in MeOH (10 mL) was stirred at 15° C. overnight. After the reaction, it was filtered to afford crude 2-chloro-6-(4-fluorobenzyl)-5H-pyrrolo[3,4-b]pyridin-7(6H)-one (75 mg, yield: 72%). $^1$H-NMR (CDCl$_3$, 400 MHz) δ 7.73 (d, J=8.0 Hz, 1H), 7.47 (d, J=8.0 Hz, 1H), 7.28~7.31 (m, 2H), 7.05 (t, J=8.4 Hz, 2H), 4.82 (s, 2H), 4.25 (s, 2H). MS (M+H)$^+$: 277/279.

Step 5—Synthesis of 5-(6-(4-fluorobenzyl)-7-oxo-6,7-dihydro-5H-pyrrolo[3,4-b]pyridin-2-yl)-2-(4-fluorophenyl)-N-methyl-6-(N-methylmethylsulfonamido)benzofuran-3-carboxamide

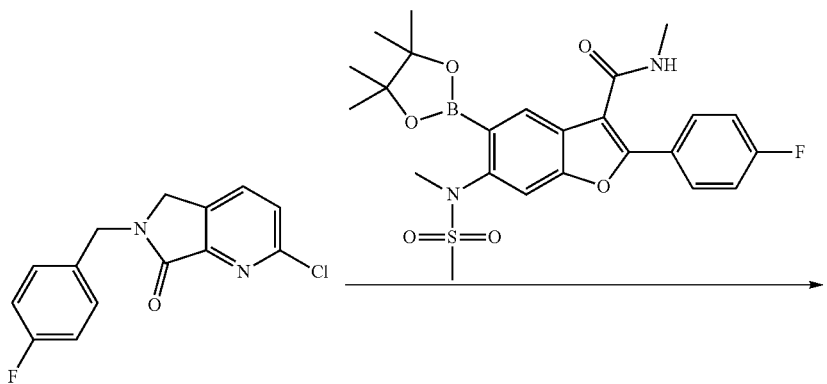

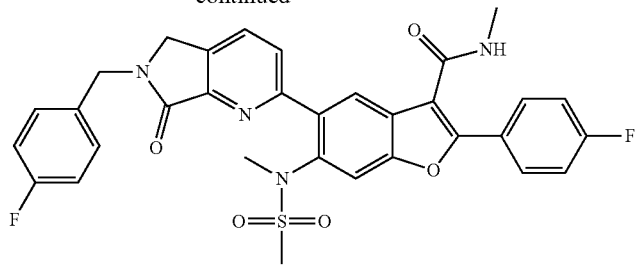

A solution of 2-chloro-6-(4-fluorobenzyl)-5H-pyrrolo[3,4-b]pyridin-7(6H)-one (70 mg, 0.25 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (152 mg, 0.30 mmol), $K_3PO_4 \cdot 3H_2O$ (200 mg, 0.76 mmol), $Pd_2(dba)_3$ (23 mg, 0.03 mmol) and X-Phos (23 mg, 0.06 mmol) in dioxane/$H_2O$ (2 mL/0.5 mL) was stirred at 110° C. for 1 hour. After the reaction, the mixture was filtered and the filtrate was diluted with water (20 mL) and extracted with EtOAc (20 mL*3). The organic layer was washed with brine (10 mL*3), dried over $Na_2SO_4$ and concentrated. The residue was purified by prep-HPLC to afford the product of 5-(6-(4-fluorobenzyl)-7-oxo-6,7-dihydro-5H-pyrrolo[3,4-b]pyridin-2-yl)-2-(4-fluorophenyl)-N-methyl-6-(N-methylmethylsulfonamido)benzofuran-3-carboxamide (42 mg, yield: 27%). $^1$H-NMR (CDCl$_3$, 400 MHz) δ 7.97~8.02 (m, 3H), 7.82~7.88 (m, 2H), 7.64 (s, 1H), 7.33~7.36 (m, 2H), 7.22 (t, J=8.8 Hz, 2H) 7.18 (t, J=8.4 Hz, 2H), 6.08 (br s, 1H), 4.86 (s, 2H), 4.34 (s, 2H), 3.16 (s, 3H), 3.01 (d, J=4.8 Hz, 3H), 2.99 (s, 3H). MS (M+H)$^+$: 617.

Example 30

Step 1—Synthesis of 3-(benzyloxy)-6-(2-(4-fluorophenyl)-3-(methylcarbamoyl)-6-(N-methylmethylsulfonamido)benzofuran-5-yl)picolinic acid

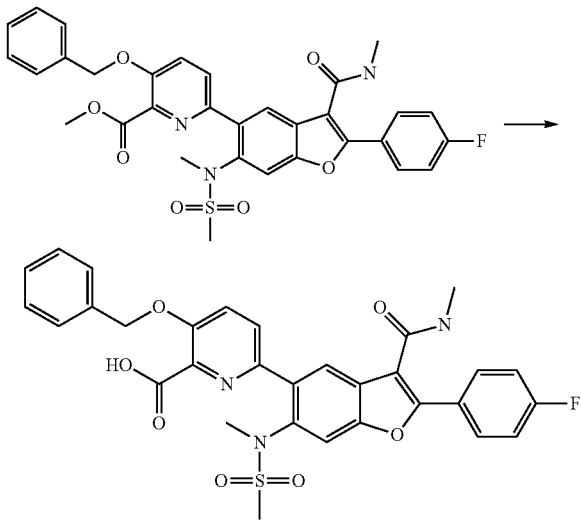

To a suspension of methyl 3-(benzyloxy)-6-(2-(4-fluorophenyl)-3-(methylcarbamoyl)-6-(N-methylmethylsulfonamido)benzofuran-5-yl)picolinate (430 mg, 0.70 mmol) in MeOH (4 mL) was added 1N NaOH (2.10 ml, 2.09 mmol). The resulting mixture was stirred at RT overnight, then added 1N HCl (2.10 ml, 2.09 mmol) was added. The reaction was concentrated in vacuo. The resulting residue was treated with EtOH/DCM (1:1) and filtered to remove the solid. The filtrate was concentrated in vacuo to provide 3-(benzyloxy)-6-(2-(4-fluorophenyl)-3-(methylcarbamoyl)-6-(N-methylmethylsulfonamido)benzofuran-5-yl)picolinic acid (430 mg, yield: 102%). MS (M+H)$^+$: 604.

Step 2—Synthesis of (R)-3-(benzyloxy)-6-(2-(4-fluorophenyl)-3-(methylcarbamoyl)-6-(N-methylmethylsulfonamido)benzofuran-5-yl)-N-(1-(4-fluorophenyl)ethyl)picolinamide

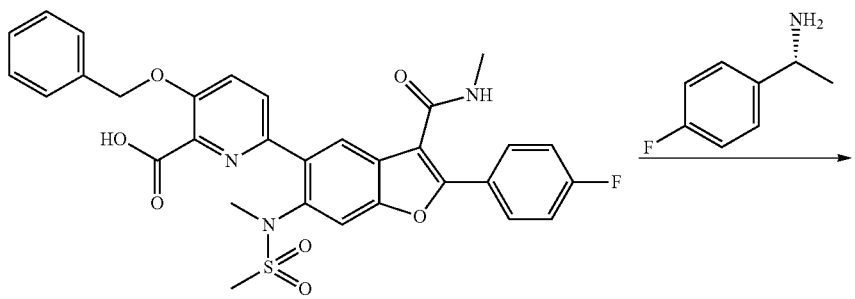

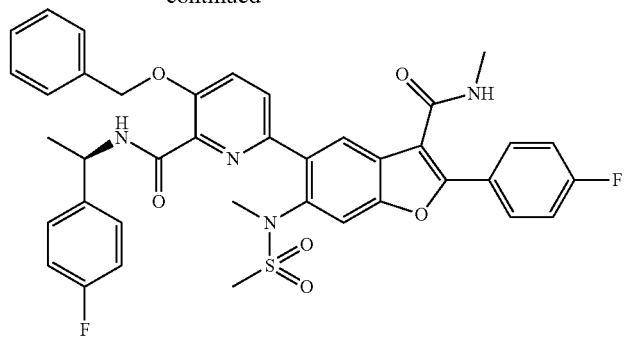

3-(benzyloxy)-6-(2-(4-fluorophenyl)-3-(methylcarbamoyl)-6-(N-methylmethylsulfonamido)benzofuran-5-yl)picolinic acid (110 mg, 0.18 mmol) was suspended in THF (2 ml), cooled to 0° C., then 4-methylmorpholine (55.3 mg, 0.55 mmol) and ethylchloroformate (27.7 mg, 0.26 mmol) were added. The resulting mixture was stirred at 0° C. for 1 h, then (R)-1-(4-fluorophenyl)ethylamine was added. The reaction was warmed to RT and stirred for 1 h, then concentrated in vacuo. The resulting residue was purified using column chromatography (eluted with 0-5% MeOH/DCM) to provide (R)-3-(benzyloxy)-6-(2-(4-fluorophenyl)-3-(methylcarbamoyl)-6-(N-methylmethylsulfonamido)benzofuran-5-yl)-N-(1-(4-fluorophenyl)ethyl)picolinamide (100 mg, yield: 76%). MS (M+H)+: 724.

Step 3—Synthesis of (R)-6-(2-(4-fluorophenyl)-3-(methylcarbamoyl)-6-(N-methylmethylsulfonamido)benzofuran-5-yl)-N-(1-(4-fluorophenyl)ethyl)-3-hydroxypicolinamide

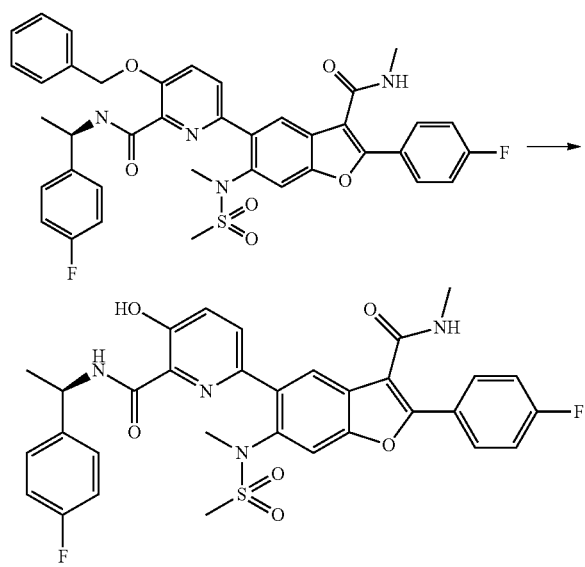

To a solution of (R)-6-(2-(4-fluorophenyl)-3-(methylcarbamoyl)-6-(N-methylmethylsulfonamido)benzofuran-5-yl)-N-(1-(4-fluorophenyl)ethyl)-3-hydroxypicolinamide (100 mg, 0.14 mmol) in MeOH (1 mL) and ethyl acetate (6 ml) was added 20% Pd(OH)2 on carbon (39 mg, 0.28 mmol) under H2 balloon. The resulting mixture was stirred at RT for 30 min. The reaction was filtered through a pad of celite and washed with ethyl acetate. The combined filtrate was evaporated in vacuo to provide (R)-6-(2-(4-fluorophenyl)-3-(methylcarbamoyl)-6-(N-methylmethylsulfonamido)benzofuran-5-yl)-N-(1-(4-fluorophenyl)ethyl)-3-hydroxypicolinamide (80 mg, yield: 91%) MS (M+H)+: 634.

Step 4—Synthesis of (R)-2-(4-fluorophenyl)-5-(3-(1-(4-fluorophenyl)ethyl)-4-oxo-3,4-dihydro-2H-pyrido[2,3-e][1,3]oxazin-6-yl)-N-methyl-6-(N-methylmethylsulfonamido)benzofuran-3-carboxamide

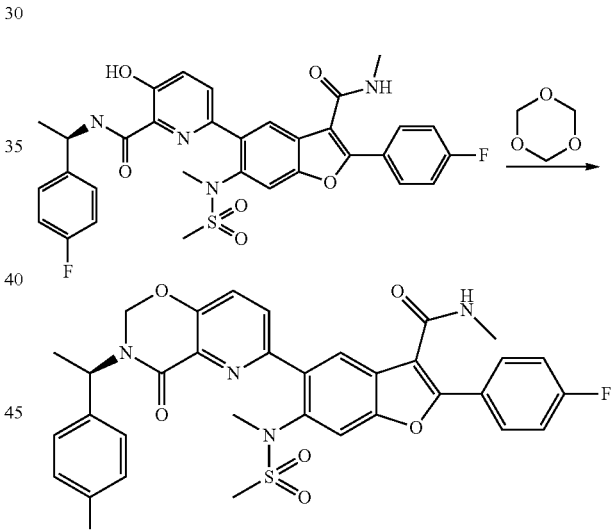

(R)-6-(2-(4-fluorophenyl)-3-(methylcarbamoyl)-6-(N-methylmethylsulfonamido)benzofuran-5-yl)-N-(1-(4-fluorophenyl)ethyl)-3-hydroxypicolinamide (80 mg, 0.13 mmol), 1,3,5-trioxane (114 mg, 1.26 mmol), H2SO4 (20 μl, 0.38 mmol) and sodium sulfate (159 mg, 1.26 mmol) in 1,2-dichloroethane (5 ml) were sealed in a tube. The mixture was microwaved at 80° C. for 1 h. 1N NaOH (10 ml) was added and the mixture extracted with ethyl acetate, dried over Na2SO4, filtered and concentrated in vacuo. Preparative TLC gave (R)-2-(4-fluorophenyl)-5-(3-(1-(4-fluorophenyl)ethyl)-4-oxo-3,4-dihydro-2H-pyrido[2,3-e][1,3]oxazin-6-yl)-N-methyl-6-(N-methylmethylsulfonamido)benzofuran-3-carboxamide (17 mg, yield: 21%). MS (M+H)+: 647.

Examples 31-34, depicted in the table below, were prepared using the method described above.

| Example | Structure | IUPAC Name | MS (M+H)+ |
|---|---|---|---|
| 31 | 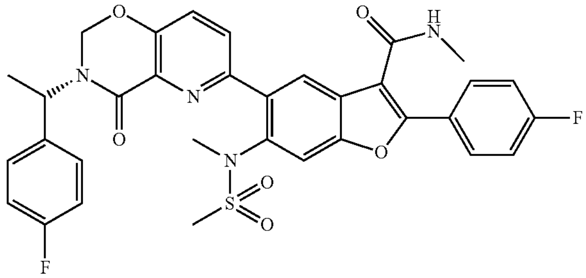 | (S)-2-(4-fluorophenyl)-5-(3-(1-(4-fluorophenyl)ethyl)-4-oxo-3,4-dihydro-2H-pyrido[2,3-e][1,3]oxazin-6-yl)-N-methyl-6-(N-methylmethylsulfonamido)benzofuran-3-carboxamide | 647 |
| 32 | 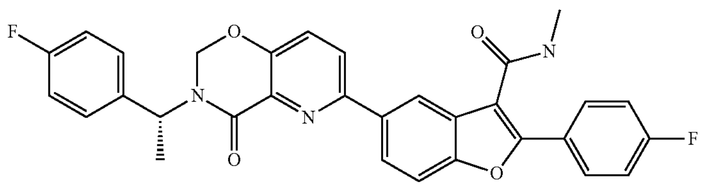 [SMILES: CNC(=O)c1c(-c2ccc(F)cc2)oc2ccc(-c3ccc4c(n3)C(=O)N([C@H](C)c3ccc(F)cc3)CO4)cc12] | (R)-2-(4-fluorophenyl)-5-(3-(1-(4-fluorophenyl)ethyl)-4-oxo-3,4-dihydro-2H-pyrido[2,3-e][1,3]oxazin-6-yl)-N-methylbenzofuran-3-carboxamide | 540 |
| 33 | 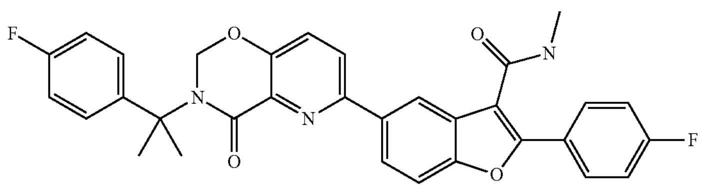 [SMILES: CNC(=O)c1c(-c2ccc(F)cc2)oc2ccc(-c3ccc4c(n3)C(=O)N(C(C)(C)c3ccc(F)cc3)CO4)cc12] | 2-(4-fluorophenyl)-5-(3-(2-(4-fluorophenyl)propan-2-yl)-4-oxo-3,4-dihydro-2H-pyrido[2,3-e][1,3]oxazin-6-yl)-N-methylbenzofuran-3-carboxamide | 554 |
| 34 | 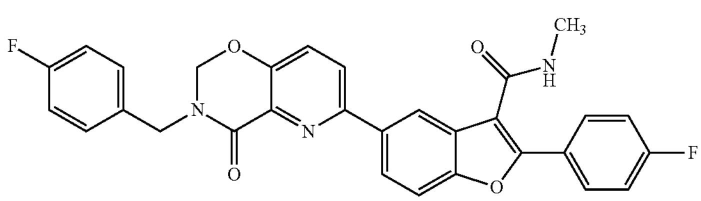 [SMILES: CNC(=O)c1c(-c2ccc(F)cc2)oc2ccc(-c3ccc4c(n3)C(=O)N(Cc3ccc(F)cc3)CO4)cc12] | 5-(3-(4-fluorobenzyl)-4-oxo-3,4-dihydro-2H-pyrido[2,3-e][1,3]oxazin-6-yl)-2-(4-fluorophenyl)-N-methylbenzofuran-3-carboxamide | 526 |

Example 35

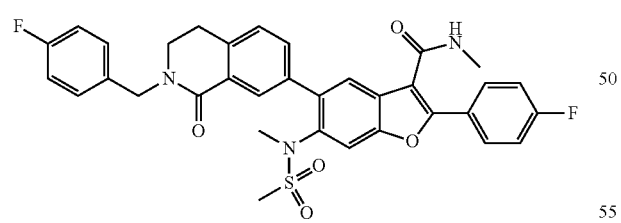

Step 1—Synthesis of 7-bromo-2-(4-fluorobenzyl)-3,4-dihydroisoquinolin-1(2H)-one

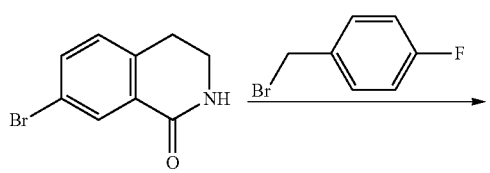

-continued

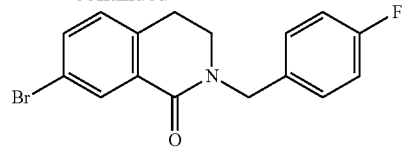

To a solution of 7-bromo-3,4-dihydroisoquinolin-1(2H)-one (150 mg, 0.66 mmol) and 1-(bromomethyl)-4-fluorobenzene (151 mg, 0.80 mmol) in 1,4-dioxane (5 ml) was added potassium t-butoxide (112 mg, 1.00 mmol). The resulting mixture was stirred at RT overnight. Solids were removed by filtration. Then the mixture was concentrated in vacuo to give 7-bromo-2-(4-fluorobenzyl)-3,4-dihydroisoquinolin-1(2H)-one (222 mg, yield: 100%). MS (M+H)+: 335.

Step 2—Synthesis of 5-(2-(4-fluorobenzyl)-1-oxo-1,2,3,4-tetrahydroisoquinolin-7-yl)-2-(4-fluorophenyl)-N-methyl-6-(N-methylmethylsulfonamido)benzofuran-3-carboxamide

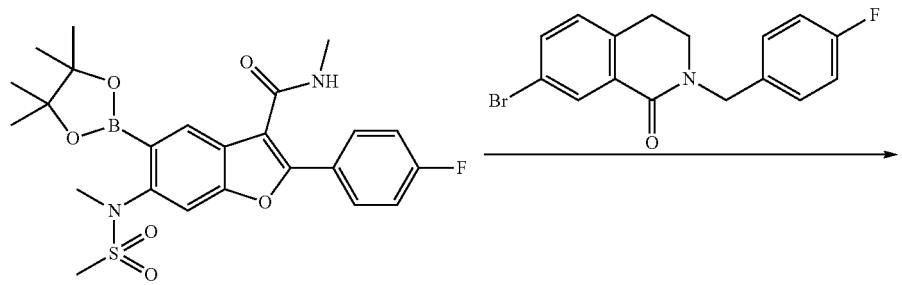

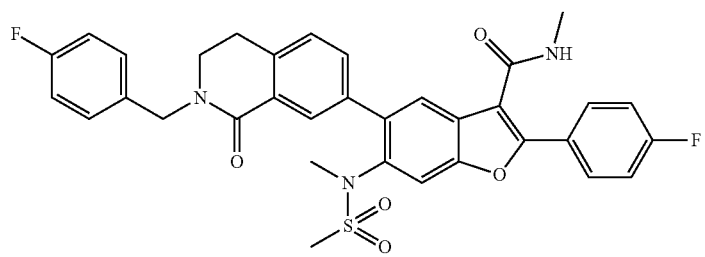

To a degassed solution of 7-bromo-2-(4-fluorobenzyl)-3,4-dihydroisoquinolin-1(2H)-one (222 mg, 0.66 mmol) and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (200 mg, 0.40 mmol) in 1,4-dioxane (5 mL) and water (200 μl) was added Cs$_2$CO$_3$ (260 mg, 0.80 mmol) and 1,1'-bis(di-tert-butylphosphino)ferrocene palladium dichloride (26 mg, 0.04 mmol) under N$_2$ protection. The resulting mixture was heated to 90° C. and stirred at this temperature for 3 h. The reaction was cooled, filtered through a pad of celite and washed with ethyl acetate. The combined filtrate was evaporated in vacuo. The resulting residue was purified using column chromatography (eluted with 0-30% EtOAc/DCM) to provide 5-(2-(4-fluorobenzyl)-1-oxo-1,2,3,4-tetrahydroisoquinolin-7-yl)-2-(4-fluorophenyl)-N-methyl-6-(N-methylmethylsulfonamido)benzofuran-3-carboxamide (240 mg, yield: 96%). MS (M+H)$^+$: 630.

Example 36, depicted in the table below, was prepared using the method described above.

| Example | Structure | IUPAC Name | MS (M+H)$^+$ |
|---|---|---|---|
| 36 | 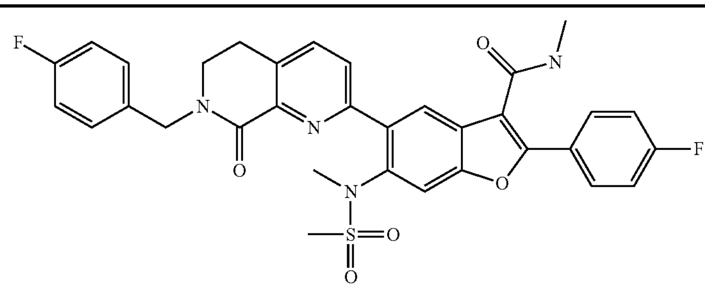 | 5-(7-(4-fluorobenzyl)-8-oxo-5,6,7,8-tetrahydro-1,7-naphthyridin-2-yl)-2-(4-fluorophenyl)-N-methyl-6-(N-methylmethylsulfonamido)benzofuran-3-carboxamide | 631 |
| 37 | 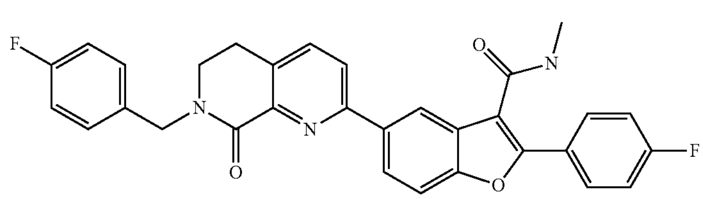 [SMILES: CNC(=O)c1c(-c2ccc(F)cc2)oc2ccc(-c3ccc4c(n3)C(=O)N(Cc3ccc(F)cc3)CC4)cc12] | 5-(7-(4-fluorobenzyl)-8-oxo-5,6,7,8-tetrahydro-1,7-naphthyridin-2-yl)-2-(4-fluorophenyl)-N-methylbenzofuran-3-carboxamide | 524 |

Example 38

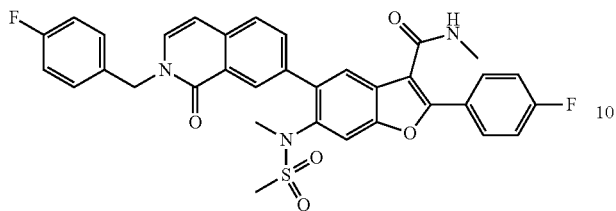

To a solution of 7-bromoisoquinolin-1(2H)-one (300 mg, 1.34 mmol) and 1-(bromomethyl)-4-fluorobenzene (380 mg, 2.01 mmol) in THF (8 ml) was added potassium t-butoxide (300 mg, 2.68 mmol) and tetrabutylammonium iodide (50 mg, 0.13 mmol). The resulting mixture was stirred at RT for 3 h. The solid was removed by filtration, then concentrated in vacuo. The resulting residue was purified using column chromatography (eluted with 0-30% EtOAc/DCM) to provide 7-bromo-2-(4-fluorobenzyl)-3,4-dihydroisoquinolin-1(2H)-one (410 mg, yield: 92%) (M+H)$^+$: 333.

Step 2—Synthesis of 5-(2-(4-fluorobenzyl)-1-oxo-1,2-dihydroisoquinolin-7-yl)-2-(4-fluorophenyl)-N-methyl-6-(N-methylmethylsulfonamido)benzofuran-3-carboxamide

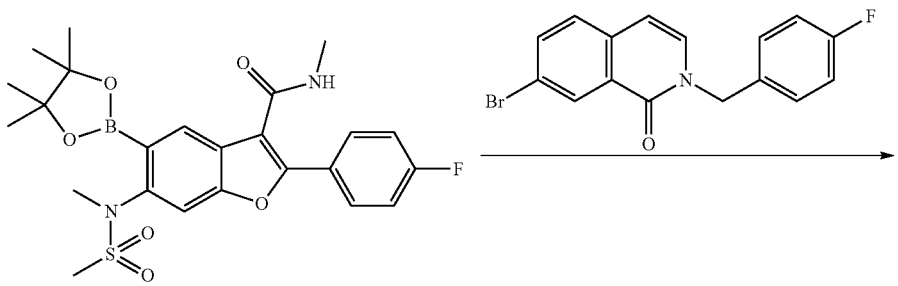

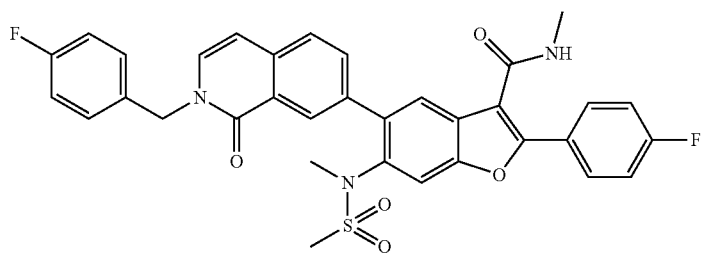

Step 1—Synthesis of 7-bromo-2-(4-fluorobenzyl)isoquinolin-1(2H)-one

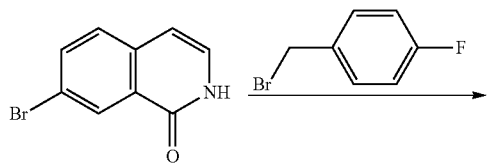

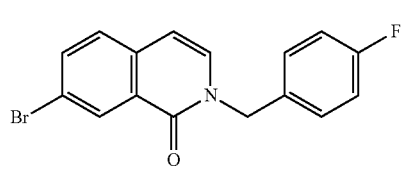

To a degassed solution of 7-bromo-2-(4-fluorobenzyl)isoquinolin-1(2H)-one (149 mg, 0.45 mmol) and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (150 mg, 0.30 mmol) in 1,4-dioxane (5 mL) and water (300 µl) was added Cs$_2$CO$_3$ (195 mg, 0.60 mmol) and 1,1'-bis(di-tert-butylphosphino)ferrocene palladium dichloride (19 mg, 0.03 mmol) under N$_2$ protection. The resulting mixture was heated to 90° C. and stirred at this temperature for 3 h. The reaction was cooled, filtered through a pad of celite and washed with ethyl acetate. The combined filtrate was evaporated in vacuo. The resulting residue was purified using column chromatography (eluted with 0-30% EtOAc/DCM) to provide 5-(2-(4-fluorobenzyl)-1-oxo-1,2-dihydroisoquinolin-7-yl)-2-(4-fluorophenyl)-N-methyl-6-(N-methylmethylsulfonamido)benzofuran-3-carboxamide (140 mg, yield: 75%). (M+H)$^+$: 628.

Example 39

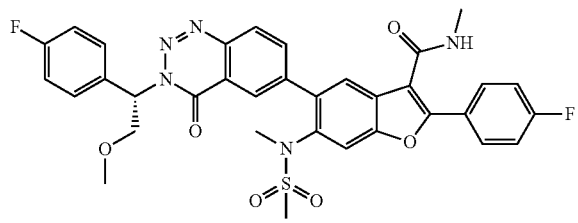 [SMILES: CNC(=O)c1c(-c2ccc(F)cc2)oc2cc(N(C)S(C)(=O)=O)c(-c3ccc4nnn([C@H](COC)c5ccc(F)cc5)c(=O)c4c3)cc12]

Step 1—Synthesis of (S)-2-(4-fluorophenyl)-5-(3-(1-(4-fluorophenyl)-2-methoxyethyl)-4-oxo-3,4-dihydrobenzo[d][1,2,3]triazin-6-yl)-N-methyl-6-(N-methylmethylsulfonamido)benzofuran-3-carboxamide To a solution of 6-bromo-1H-benzo[d][1,3]oxazine-2,4-dione (22 mg, 0.09 mmol) in 1 ml dioxane was added DIEA (31 µl) followed by (S)-1-(4-fluorophenyl)-2-methoxyethanamine (15 mg, 0.09 mmol). The mixture was microwaved at 100° C. for 30 min. Then 250 µl 2N HCl (aq.) was added followed by a solution of NaNO$_2$ (12.4 mg in 250 µl water). The mixture was stirred at RT for 1 h. To this mixture, 0.5 mL EtOAc was added and stirred for 5 min. Then, the stirring was stopped and the layers were allowed to separate. The bottom aqueous layer was removed by a pipette and was then 250 µl 1N K3PO4 (aq.) was added. To this mixture was added 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (30 mg, 0.06 mmol) followed by Pd(dtbpf)Cl$_2$ (2 mg). The vial was sealed and microwaved at 80° C. for 2 h. The reaction mixtures were diluted with 0.5 mL H$_2$O and the aq. layers were separated. The organic was diluted with 0.5 mL DMF and filtered. The filtrate was purified using semi-prep HPLC to provide (S)-2-(4-fluorophenyl)-5-(3-(1-(4-fluorophenyl)-2-methoxyethyl)-4-oxo-3,4-dihydrobenzo[d][1,2,3]triazin-6-yl)-N-methyl-6-(N-methylmethylsulfonamido)benzofuran-3-carboxamide. (M+H)$^+$: 674.

Examples 40-48, depicted in the table below, were prepared using the method described above.

| Example | Structure | IUPAC Name | MS (M + H)$^+$ |
|---|---|---|---|
| 40 | 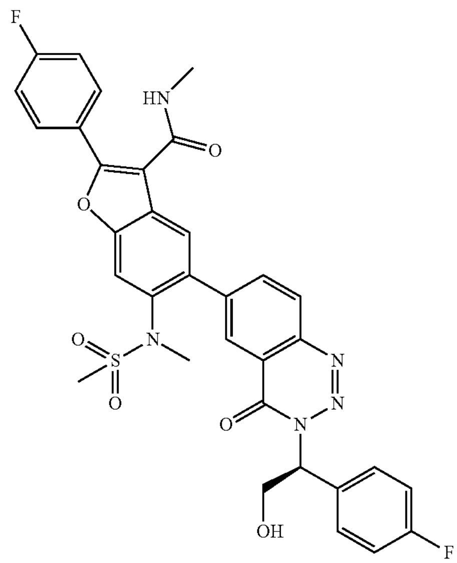 [SMILES: CNC(=O)c1c(-c2ccc(F)cc2)oc2cc(N(C)S(C)(=O)=O)c(-c3ccc4nnn([C@H](CO)c5ccc(F)cc5)c(=O)c4c3)cc12] | 2-(4-fluorophenyl)-5-{3-[(1S)-1-(4-fluorophenyl)-2-hydroxyethyl]-4-oxo-3,4-dihydro-1,2,3-benzotriazin-6-yl}-N-methyl-6-[methyl(methylsulfonyl)amino]-1-benzofuran-3-carboxamide | 660 |
| 41 | 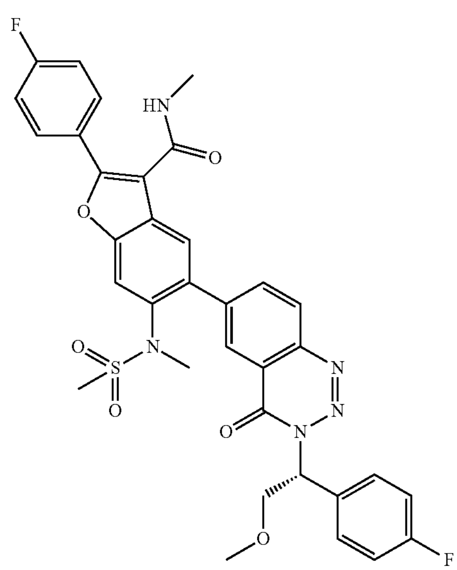 [SMILES: CNC(=O)c1c(-c2ccc(F)cc2)oc2cc(N(C)S(C)(=O)=O)c(-c3ccc4nnn([C@@H](COC)c5ccc(F)cc5)c(=O)c4c3)cc12] | 2-(4-fluorophenyl)-5-{3-[(1R)-1-(4-fluorophenyl)-2-methoxyethyl]-4-oxo-3,4-dihydro-1,2,3-benzotriazin-6-yl}-N-methyl-6-[methyl(methylsulfonyl)amino]-1-benzofuran-3-carboxamide | 674 |

-continued
| Example | Structure | IUPAC Name | MS (M + H)+ |
|---|---|---|---|
| 42 | 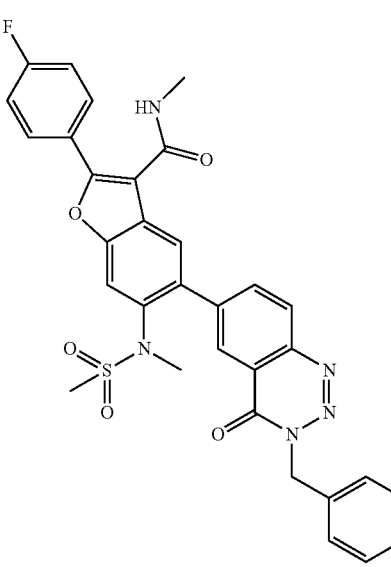 | 5-(3-benzyl-4-oxo-3,4-dihydro-1,2,3-benzotriazin-6-yl)-2-(4-fluorophenyl)-N-methyl-6-[methyl(methylsulfonyl)amino]-1-benzofuran-3-carboxamide | 612 |
| 43 | 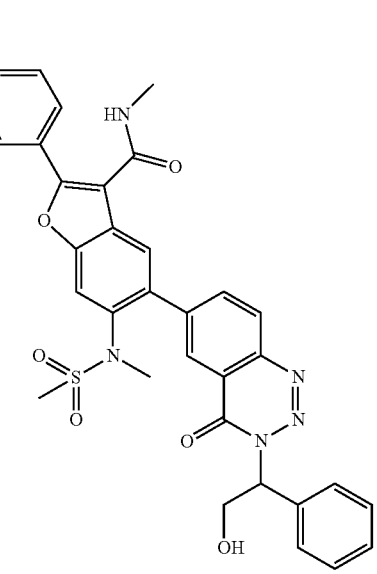 | 2-(4-fluorophenyl)-5-[3-(2-hydroxy-1-phenylethyl)-4-oxo-3,4-dihydro-1,2,3-benzotriazin-6-yl]-N-methyl-6-[methyl(methylsulfonyl)amino]-1-benzofuran-3-carboxamide | 642 |

-continued

| Example | Structure | IUPAC Name | MS (M + H)+ |
|---|---|---|---|
| 44 | 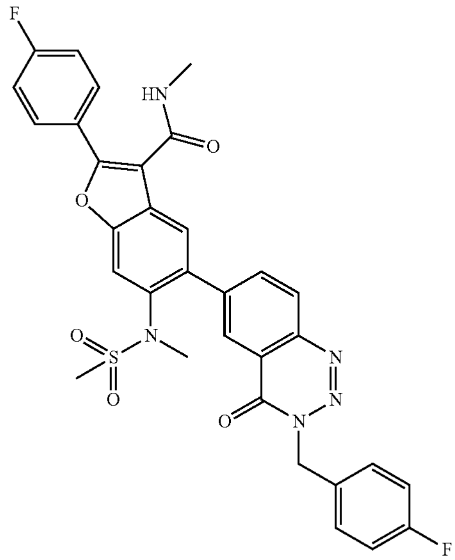 [SMILES: CNC(=O)c1c(-c2ccc(F)cc2)oc2cc(N(C)S(C)(=O)=O)c(-c3ccc4nnn(Cc5ccc(F)cc5)c(=O)c4c3)cc12] | 5-[3-(4-fluorobenzyl)-4-oxo-3,4-dihydro-1,2,3-benzotriazin-6-yl]-2-(4-fluorophenyl)-N-methyl-6-[methyl(methylsulfonyl)amino]-1-benzofuran-3-carboxamide | 630 |
| 45 | 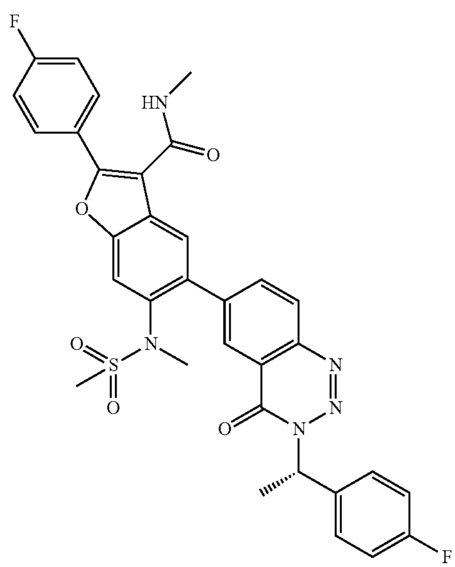 [SMILES: CNC(=O)c1c(-c2ccc(F)cc2)oc2cc(N(C)S(C)(=O)=O)c(-c3ccc4nnn([C@@H](C)c5ccc(F)cc5)c(=O)c4c3)cc12] | 2-(4-fluorophenyl)-5-{3-[(1S)-1-(4-fluorophenyl)ethyl]-4-oxo-3,4-dihydro-1,2,3-benzotriazin-6-yl}-N-methyl-6-[methyl(methylsulfonyl)amino]-1-benzofuran-3-carboxamide | 644 |

-continued

| Example | Structure | IUPAC Name | MS (M + H)+ |
|---------|-----------|------------|-------------|
| 46 | 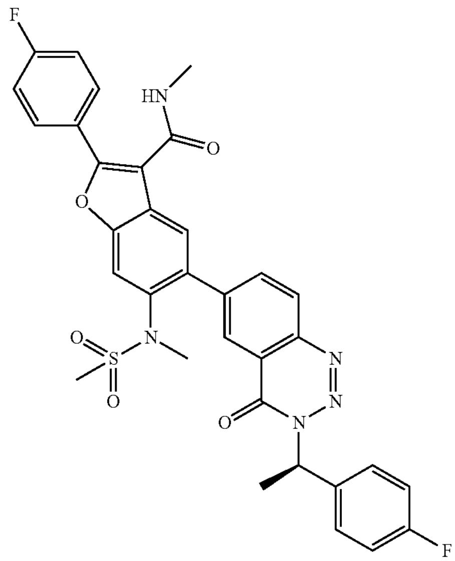 [SMILES: CNC(=O)c1c(-c2ccc(F)cc2)oc2cc(N(C)S(C)(=O)=O)c(-c3ccc4nnn([C@H](C)c5ccc(F)cc5)c(=O)c4c3)cc12] | 2-(4-fluorophenyl)-5-{3-[(1R)-1-(4-fluorophenyl)ethyl]-4-oxo-3,4-dihydro-1,2,3-benzotriazin-6-yl}-N-methyl-6-[methyl(methylsulfonyl)amino]-1-benzofuran-3-carboxamide | 644 |
| 47 | 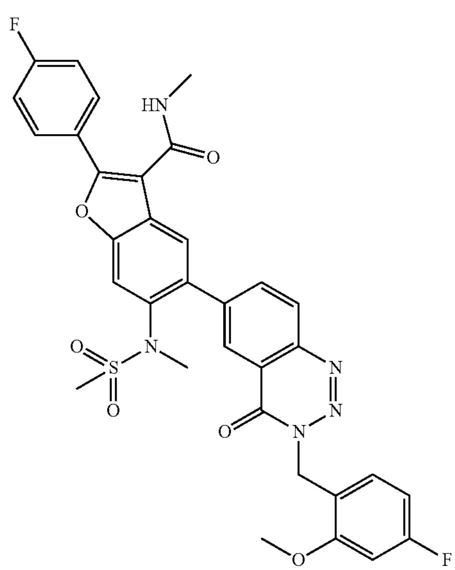 [SMILES: CNC(=O)c1c(-c2ccc(F)cc2)oc2cc(N(C)S(C)(=O)=O)c(-c3ccc4nnn(Cc5ccc(F)cc5OC)c(=O)c4c3)cc12] | 5-[3-(4-fluoro-2-methoxybenzyl)-4-oxo-3,4-dihydro-1,2,3-benzotriazin-6-yl]-2-(4-fluorophenyl)-N-methyl-6-[methyl(methylsulfonyl)amino]-1-benzofuran-3-carboxamide | 660 |

| Example | Structure | IUPAC Name | MS (M + H)+ |
|---|---|---|---|
| 48 | 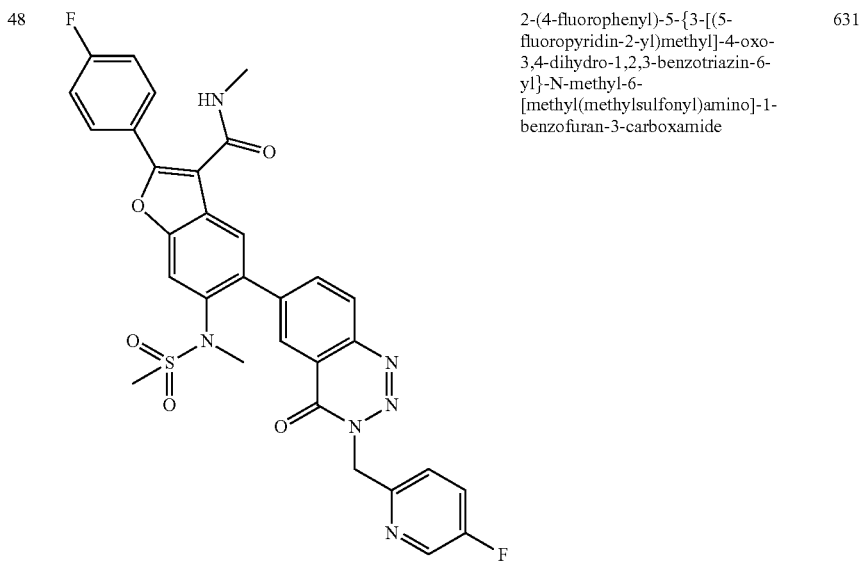 | 2-(4-fluorophenyl)-5-{3-[(5-fluoropyridin-2-yl)methyl]-4-oxo-3,4-dihydro-1,2,3-benzotriazin-6-yl}-N-methyl-6-[methyl(methylsulfonyl)amino]-1-benzofuran-3-carboxamide | 631 |

Example 49

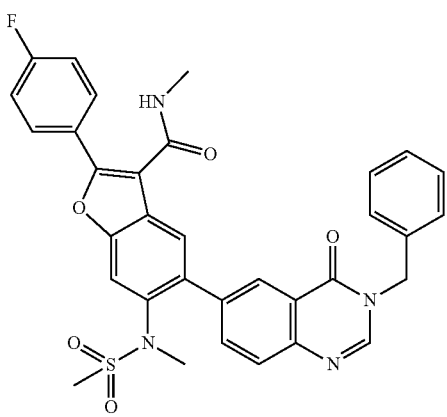 [SMILES: CNC(=O)c1c(-c2ccc(F)cc2)oc2cc(N(C)S(C)(=O)=O)c(-c3ccc4ncn(Cc5ccccc5)c(=O)c4c3)cc12]

Step 1—Synthesis of 5-(3-benzyl-4-oxo-3,4-dihydroquinazolin-6-yl)-2-(4-fluorophenyl)-N-methyl-6-(N-methylmethylsulfonamido)benzofuran-3-carboxamide To a solution of 6-bromo-1H-benzo[d][1,3]oxazine-2,4-dione in 1 mL trimethoxymethane was added DIEA (31 μL) followed by phenylmethanamine. The mixture was microwaved at 100° C. for 30 min. 100 mg polymer bound TsOH was then added to the reaction and sealed and microwaved at 140° C. for 1 h. The reaction mixture was then filtered and the polymer washed with 1 mL EtOAc. The filtrate was concentrated in Genevac. The residue was dissolved in 1 ml dioxane, followed by 0.25 mL 1N $K_3PO_4$ aq. To this mixture was added 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (30 mg) followed by Pd(dtbpf)Cl$_2$ (2 mg). The vial was sealed and microwaved at 90° C. for 30 min. The reaction mixtures were diluted with 0.5 ml $H_2O$ and 2 ml EtOAc. The aq. layers were separated. The organic layer was treated with 200 mg SilicycleTMD and stirred overnight. The reaction was then filtered and the silicycle residue washed with 4 ml EtOAc. The organic filtrates were combined and concentrated in Genevac. The residue was dissolved in 1.4 mL DMF and filtered. The filtrate was purified using semi-prep HPLC to provide 5-(3-benzyl-4-oxo-3,4-dihydroquinazolin-6-yl)-2-(4-fluorophenyl)-N-methyl-6-(N-methylmethylsulfonamido)benzofuran-3-carboxamide. (M+H)+: 611.

Examples 50-52, depicted in the table below, were prepared using the method described above.

| Example | Structure | IUPAC Name | MS (M + H)+ |
|---|---|---|---|
| 50 | 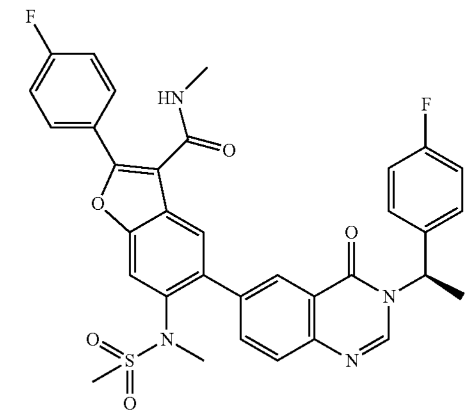 [SMILES: CNC(=O)c1c(-c2ccc(F)cc2)oc2cc(N(C)S(C)(=O)=O)c(-c3ccc4ncn([C@H](C)c5ccc(F)cc5)c(=O)c4c3)cc12] | 2-(4-fluorophenyl)-5-{3-[(1R)-1-(4-fluorophenyl)ethyl]-4-oxo-3,4-dihydroquinazolin-6-yl}-N-methyl-6-[methyl(methylsulfonyl)amino]-1-benzofuran-3-carboxamide | 643 |
| 51 | 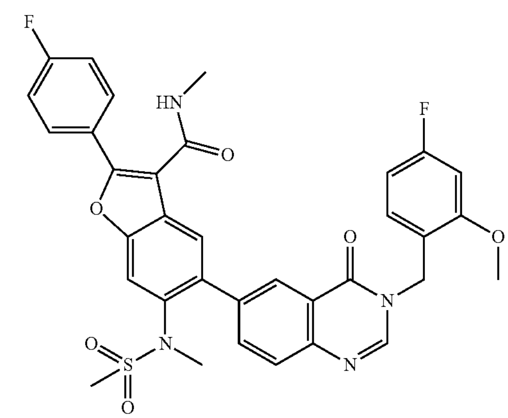 [SMILES: CNC(=O)c1c(-c2ccc(F)cc2)oc2cc(N(C)S(C)(=O)=O)c(-c3ccc4ncn(Cc5ccc(F)cc5OC)c(=O)c4c3)cc12] | 5-[3-(4-fluoro-2-methoxybenzyl)-4-oxo-3,4-dihydroquinazolin-6-yl]-2-(4-fluorophenyl)-N-methyl-6-[methyl(methylsulfonyl)amino]-1-benzofuran-3-carboxamide | 659 |
| 52 | 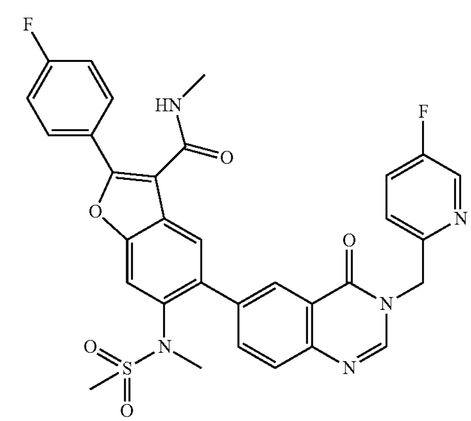 [SMILES: CNC(=O)c1c(-c2ccc(F)cc2)oc2cc(N(C)S(C)(=O)=O)c(-c3ccc4ncn(Cc5ccc(F)cn5)c(=O)c4c3)cc12] | 2-(4-fluorophenyl)-5-{3-[(5-fluoropyridin-2-yl)methyl]-4-oxo-3,4-dihydroquinazolin-6-yl}-N-methyl-6-[methyl(methylsulfonyl)amino]-1-benzofuran-3-carboxamide | 630 |

Example 53

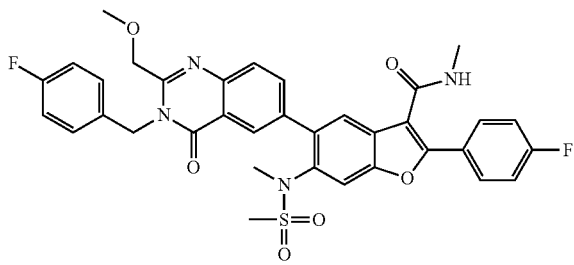 [SMILES: CNC(=O)c1c(-c2ccc(F)cc2)oc2cc(N(C)S(C)(=O)=O)c(-c3ccc4nc(COC)n(Cc5ccc(F)cc5)c(=O)c4c3)cc12]

Step 1—Synthesis of 5-(3-(4-fluorobenzyl)-2-(methoxymethyl)-4-oxo-3,4-dihydroquinazolin-6-yl)-2-(4-fluorophenyl)-N-methyl-6-(N-methylmethylsulfonamido)benzofuran-3-carboxamide To a solution of 2-amino-5-bromo-benzoic acid (19.4 mg, 0.09 mmol) in 1 ml dioxane in 10 mL microwave vial was added a stirring bar, 52 µl DIEA followed by 2-methoxyacetic acid (5.4 mg, 0.06 mmol), followed by $T_3P$ (250 µl, 50% in EtOAc). The mixture was stirred at room temp for 16 h. Then 4-fluorophenylmethanamine (15.0 mg, 0.12 mmol) was added. The mixture was stirred for 2 h at room temp then at 50° C. for 16 h. The mixture was then diluted with 0.5 mL EtOAc followed by addition of 1 mL water. The mixture was stirred at room temp for 10 min then the bottom aq layers were removed using a pipette. To the organic layer was added 0.25 mL 1 M $K_3PO_4$ aq. followed by 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (30 mg) then $Pd(dtbpf)Cl_2$ (2 mg). The vial was sealed and was microwaved at 90° C. for 2 h. The reaction mixtures were allowed to cool to room temp, diluted with 1 mL $H_2O$ and 2 mL EtOAc. The organic was separated and concentrated. The residue was purified by Prep TLC using 10% $MeOH/CH_2Cl_2$ as eluent to provide 5-(3-(4-fluorobenzyl)-2-(methoxymethyl)-4-oxo-3,4-dihydroquinazolin-6-yl)-2-(4-fluorophenyl)-N-methyl-6-(N-methylmethylsulfonamido)benzofuran-3-carboxamide. $(M+H)^+$: 673.

Examples 54-69, depicted in the table below, were prepared using the method described above.

| Example | Structure | IUPAC Name | MS (M + H)+ |
|---|---|---|---|
| 54 | 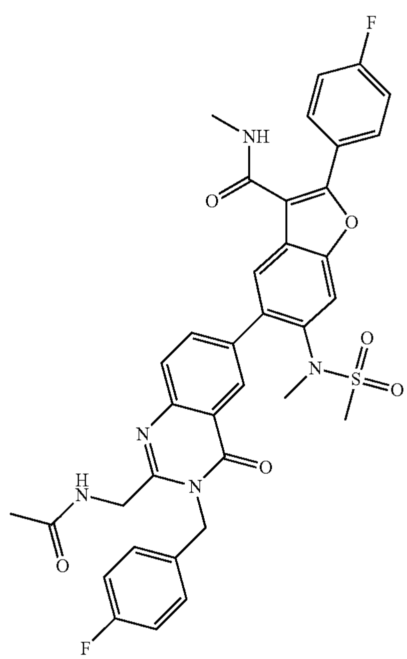 [SMILES: CNC(=O)c1c(-c2ccc(F)cc2)oc2cc(N(C)S(C)(=O)=O)c(-c3ccc4nc(CNC(C)=O)n(Cc5ccc(F)cc5)c(=O)c4c3)cc12] | 5-{2-[(acetylamino)methyl]-3-(4-fluorobenzyl)-4-oxo-3,4-dihydroquinazolin-6-yl}-2-(4-fluorophenyl)-N-methyl-6-[methyl(methylsulfonyl)amino]-1-benzofuran-3-carboxamide | 700 |

| Example | Structure | IUPAC Name | MS (M + H)+ |
|---|---|---|---|
| 55 | 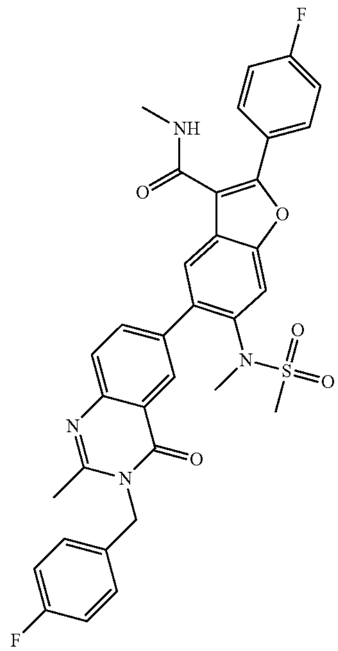 [SMILES: CNC(=O)c1c(-c2ccc(F)cc2)oc2cc(N(C)S(C)(=O)=O)c(-c3ccc4nc(C)n(Cc5ccc(F)cc5)c(=O)c4c3)cc12] | 5-[3-(4-fluorobenzyl)-2-methyl-4-oxo-3,4-dihydroquinazolin-6-yl]-2-(4-fluorophenyl)-N-methyl-6-[methyl(methylsulfonyl)amino]-1-benzofuran-3-carboxamide | 643 |
| 56 | 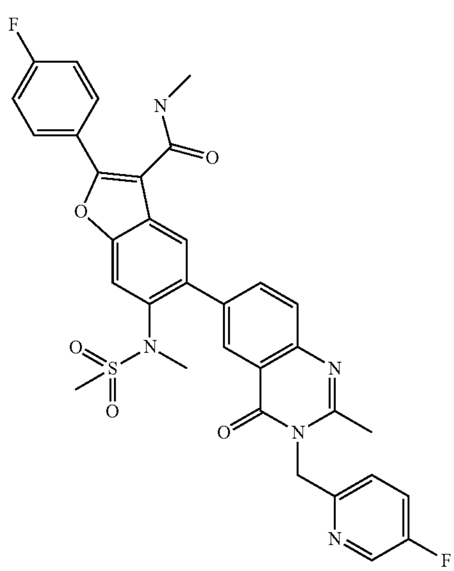 [SMILES: CNC(=O)c1c(-c2ccc(F)cc2)oc2cc(N(C)S(C)(=O)=O)c(-c3ccc4nc(C)n(Cc5ccc(F)cn5)c(=O)c4c3)cc12] | 2-(4-fluorophenyl)-5-(3-((5-fluoropyridin-2-yl)methyl)-2-methyl-4-oxo-3,4-dihydroquinazolin-6-yl)-N-methyl-6-(N-methylmethylsulfonamido)benzofuran-3-carboxamide | 644 |

-continued
| Example | Structure | IUPAC Name | MS (M + H)+ |
|---|---|---|---|
| 57 | 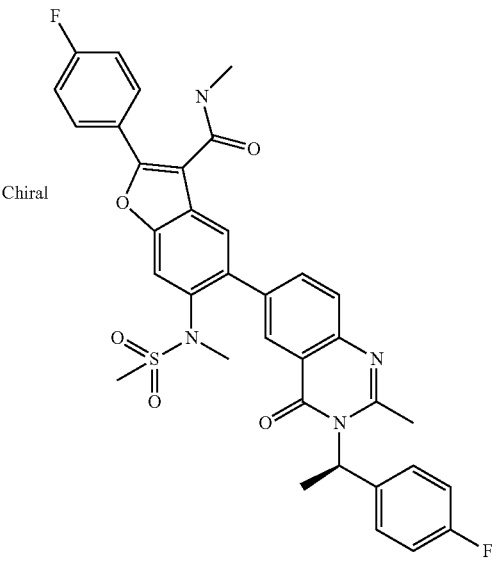 [SMILES: CNC(=O)c1c(-c2ccc(F)cc2)oc2cc(N(C)S(C)(=O)=O)c(-c3ccc4nc(C)n([C@H](C)c5ccc(F)cc5)c(=O)c4c3)cc12] | (R)-2-(4-fluorophenyl)-5-(3-(1-(4-fluorophenyl)ethyl)-2-methyl-4-oxo-3,4-dihydroquinazolin-6-yl)-N-methyl-6-(N-methylmethylsulfonamido)benzofuran-3-carboxamide | 657 |
| 58 | 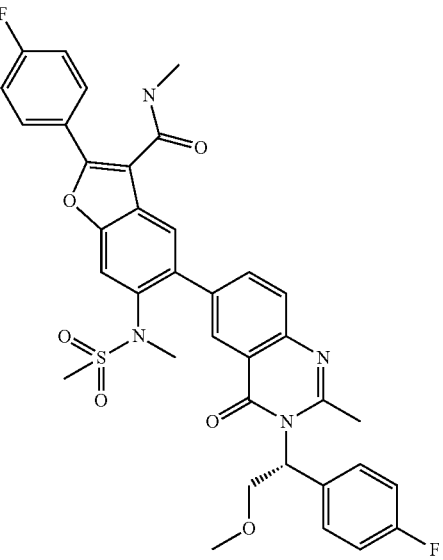 | (R)-2-(4-fluorophenyl)-5-(3-(1-(4-fluorophenyl)-2-methoxyethyl)-2-methyl-4-oxo-3,4-dihydroquinazolin-6-yl)-N-methyl-6-(N-methylmethylsulfonamido)benzofuran-3-carboxamid | 687 |

| Example | Structure | IUPAC Name | MS (M + H)+ |
|---|---|---|---|
| 59 | 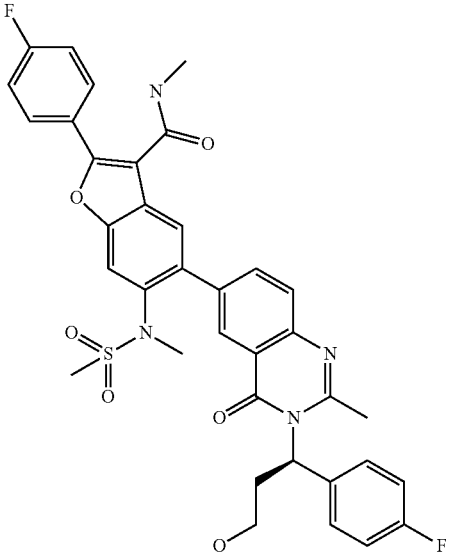 | (R)-2-(4-fluorophenyl)-5-(3-(1-(4-fluorophenyl)-3-hydroxypropyl)-2-methyl-4-oxo-3,4-dihydroquinazolin-6-yl)-N-methyl-6-(N-methylmethylsulfonamido)benzofuran-3-carboxamide | 687 |
| 60 | 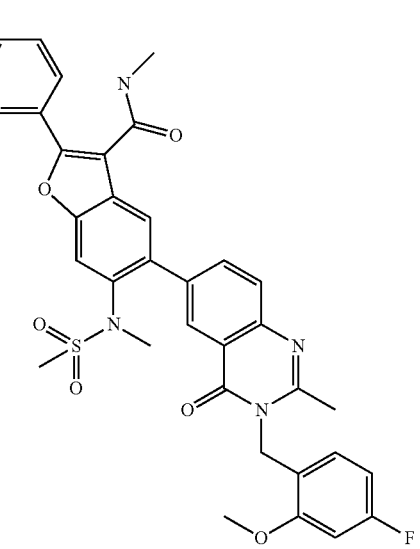 | 5-(3-(4-fluoro-2-methoxybenzyl)-2-methyl-4-oxo-3,4-dihydroquinazolin-6-yl)-2-(4-fluorophenyl)-N-methyl-6-(N-methylmethylsulfonamido)benzofuran-3-carboxamide | 673 |

-continued
| Example | Structure | IUPAC Name | MS (M + H)+ |
|---|---|---|---|
| 61 | 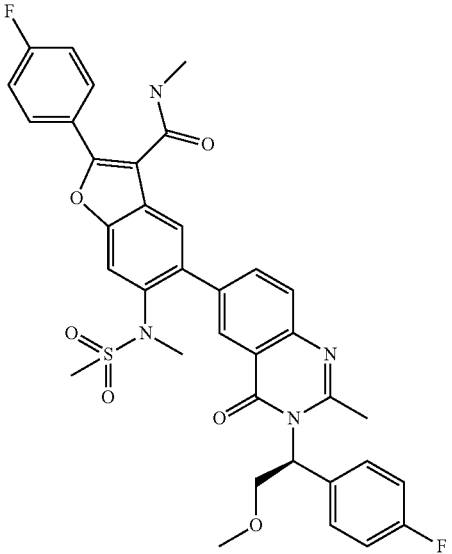 | (S)-2-(4-fluorophenyl)-5-(3-(1-(4-fluorophenyl)-2-methoxyethyl)-2-methyl-4-oxo-3,4-dihydroquinazolin-6-yl)-N-methyl-6-(N-methylmethylsulfonamido)benzofuran-3-carboxamide | 687 |
| 62 | 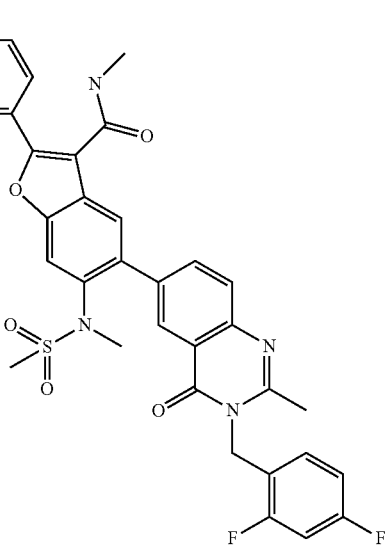 | 5-(3-(2,4-difluorobenzyl)-2-methyl-4-oxo-3,4-dihydroquinazolin-6-yl)-2-(4-fluorophenyl)-N-methyl-6-(N-methylmethylsulfonamido)benzofuran-3-carboxamide | 661 |

-continued

| Example | Structure | IUPAC Name | MS (M + H)+ |
|---|---|---|---|
| 63 | 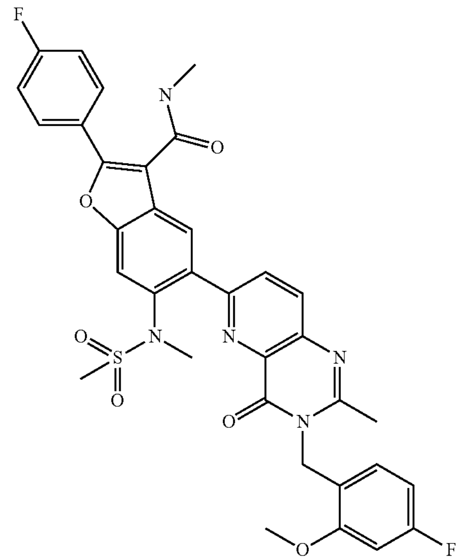 [SMILES: CNC(=O)c1c(-c2ccc(F)cc2)oc2cc(N(C)S(C)(=O)=O)c(-c3ccc4nc(C)n(Cc5ccc(F)cc5OC)c(=O)c4c3)cc12] | 5-(3-(4-fluoro-2-methoxybenzyl)-2-methyl-4-oxo-3,4-dihydropyrido[3,2-d]pyrimidin-6-yl)-2-(4-fluorophenyl)-N-methyl-6-(N-methylmethylsulfonamido)benzofuran-3-carboxamide | 674 |
| 64 | 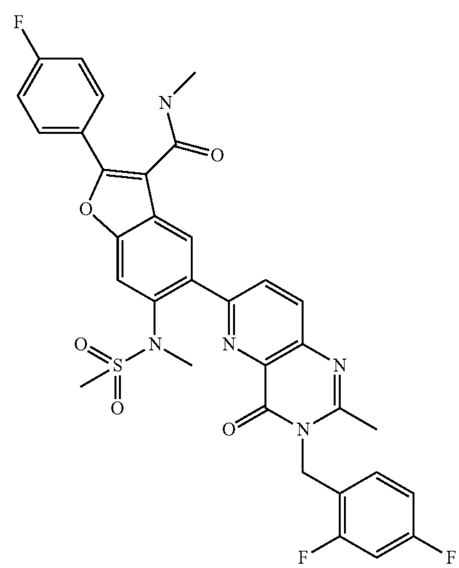 [SMILES: CNC(=O)c1c(-c2ccc(F)cc2)oc2cc(N(C)S(C)(=O)=O)c(-c3ccc4nc(C)n(Cc5ccc(F)cc5F)c(=O)c4n3)cc12] | 5-(3-(2,4-difluorobenzyl)-2-methyl-4-oxo-3,4-dihydropyrido[3,2-d]pyrimidin-6-yl)-2-(4-fluorophenyl)-N-methyl-6-(N-methylmethylsulfonamido)benzofuran-3-carboxamide | 662 |

| Example | Structure | IUPAC Name | MS (M + H)+ |
|---|---|---|---|
| 65 | 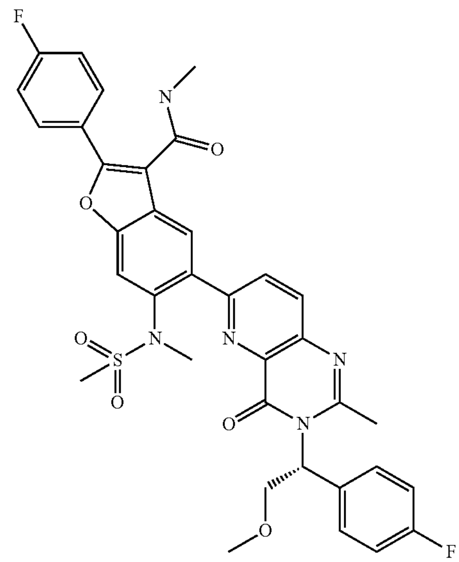 | (R)-2-(4-fluorophenyl)-5-(3-(1-(4-fluorophenyl)-2-methoxyethyl)-2-methyl-4-oxo-3,4-dihydropyrido[3,2-d]pyrimidin-6-yl)-N-methyl-6-(N-methylmethylsulfonamido)benzofuran-3-carboxamide | 688 |
| 66 | 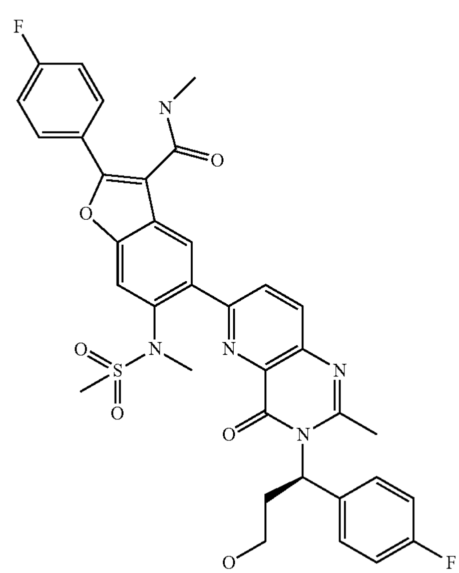 [SMILES: CNC(=O)c1c(-c2ccc(F)cc2)oc2cc(N(C)S(C)(=O)=O)c(-c3ccc4nc(C)n([C@H](CCO)c5ccc(F)cc5)c(=O)c4n3)cc12] | (R)-2-(4-fluorophenyl)-5-(3-(1-(4-fluorophenyl)-3-hydroxypropyl)-2-methyl-4-oxo-3,4-dihydropyrido[3,2-d]pyrimidin-6-yl)-N-methyl-6-(N-methylmethylsulfonamido)benzofuran-3-carboxamide | 688 |

-continued

| Example | Structure | IUPAC Name | MS (M + H)+ |
|---|---|---|---|
| 67 | 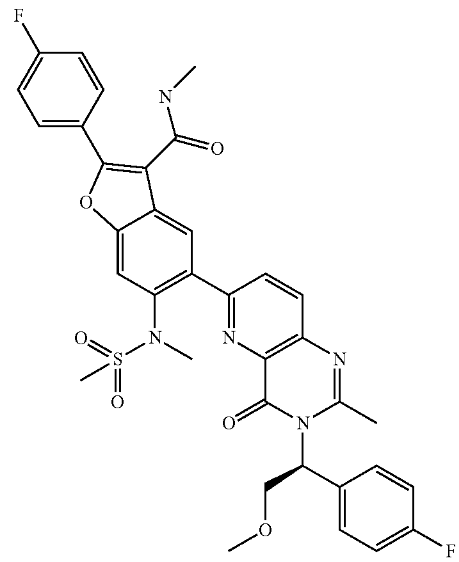 | (S)-2-(4-fluorophenyl)-5-(3-(1-(4-fluorophenyl)-2-methoxyethyl)-2-methyl-4-oxo-3,4-dihydropyrido[3,2-d]pyrimidin-6-yl)-N-methyl-6-(N-methylmethylsulfonamido)benzofuran-3-carboxamide | 688 |
| 68 | 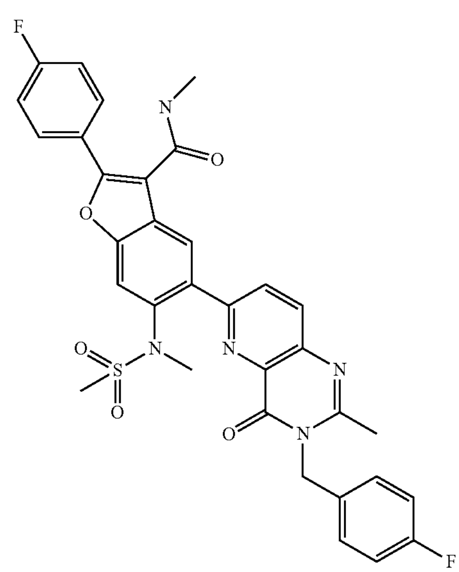 [SMILES: CNC(=O)c1c(-c2ccc(F)cc2)oc2cc(N(C)S(C)(=O)=O)c(-c3ccc4nc(C)n(Cc5ccc(F)cc5)c(=O)c4n3)cc12] | 5-(3-(4-fluorobenzyl)-2-methyl-4-oxo-3,4-dihydropyrido[3,2-d]pyrimidin-6-yl)-2-(4-fluorophenyl)-N-methyl-6-(N-methylmethylsulfonamido)benzofuran-3-carboxamide | 644 |

| Example | Structure | IUPAC Name | MS (M + H)+ |
|---|---|---|---|
| 69 | 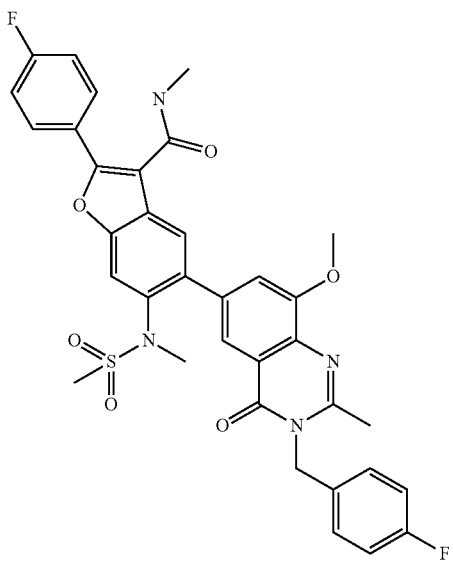 [SMILES: CNC(=O)c1c(-c2ccc(F)cc2)oc2cc(N(C)S(C)(=O)=O)c(-c3cc(OC)c4nc(C)n(Cc5ccc(F)cc5)c(=O)c4c3)cc12] | 5-(3-(4-fluorobenzyl)-8-methoxy-2-methyl-4-oxo-3,4-dihydroquinazolin-6-yl)-2-(4-fluorophenyl)-N-methyl-6-(N-methylmethylsulfonamido)benzofuran-3-carboxamide | 673 |

Example 70

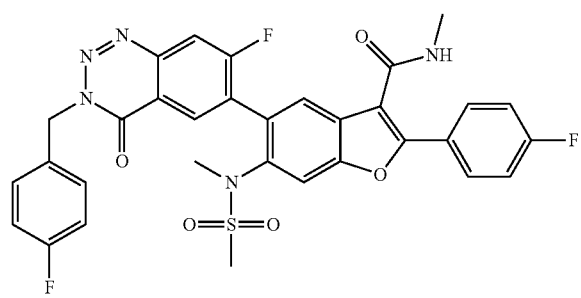 [SMILES: CNC(=O)c1c(-c2ccc(F)cc2)oc2cc(N(C)S(C)(=O)=O)c(-c3cc4c(=O)n(Cc5ccc(F)cc5)nnc4cc3F)cc12]

Step 1—Synthesis of 5-(7-fluoro-3-(4-fluorobenzyl)-4-oxo-3,4-dihydrobenzo[d][1,2,3]triazin-6-yl)-2-(4-fluorophenyl)-N-methyl-6-(N-methylmethylsulfonamido)benzofuran-3-carboxamide To a solution of substituted 2-amino-5-bromo-benzoic acids in 1 ml dioxane was added DIEA (31 µL) followed by 4-fluorobenzylamine. The mixture was microwaved at 100° C. for 30 min. Then 250 µL 2N HCl (aq.) was added followed by solution of NaNO$_2$ (12.4 mg in 250 µl water). The mixture was stirred at room temp for 1 h. To this mixture, 0.5 mL EtOAc was added and stirred for 5 min. Then, the stirring was stopped and the layers were allowed to separate. The bottom aqueous layer was removed by a pipette and then added 250 µL 1N K$_3$PO$_4$ (aq.) was added. To this mixture was added 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (25 mg) followed by Pd(dtbpf)Cl$_2$ (2 mg). The vial was sealed and microwaved at 90° C. for 30 min. The reaction mixtures were diluted with 0.5 mL H$_2$O and the aq. layers were separated. The organic layer was diluted with 0.5 ml DMF and filtered. The filtrate was purified using semi-prep HPLC to provide 5-(7-fluoro-3-(4-fluorobenzyl)-4-oxo-3,4-dihydrobenzo[d][1,2,3]triazin-6-yl)-2-(4-fluorophenyl)-N-methyl-6-(N-methylmethylsulfonamido)benzofuran-3-carboxamide. (M+H)+: 648.

Examples 71-74, depicted in the table below, were prepared using the method described above.

| Examples | Structure | IUPAC Name | MS (M + H)+ |
|---|---|---|---|
| 71 | 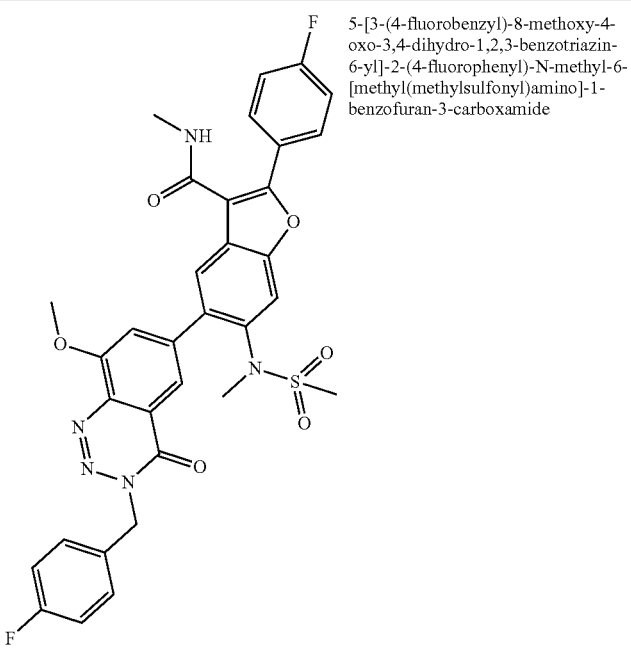 | 5-[3-(4-fluorobenzyl)-8-methoxy-4-oxo-3,4-dihydro-1,2,3-benzotriazin-6-yl]-2-(4-fluorophenyl)-N-methyl-6-[methyl(methylsulfonyl)amino]-1-benzofuran-3-carboxamide | 660 |
| 72 | 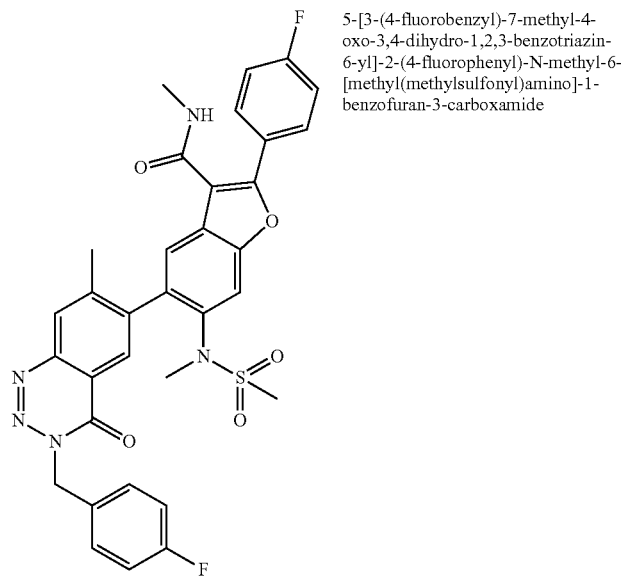 | 5-[3-(4-fluorobenzyl)-7-methyl-4-oxo-3,4-dihydro-1,2,3-benzotriazin-6-yl]-2-(4-fluorophenyl)-N-methyl-6-[methyl(methylsulfonyl)amino]-1-benzofuran-3-carboxamide | 644 |

| Examples | Structure | IUPAC Name | MS (M + H)+ |
|---|---|---|---|
| 73 | 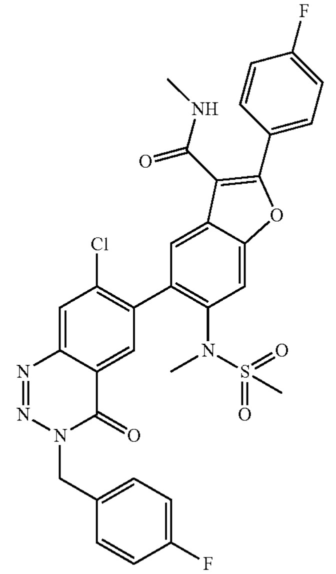 [SMILES: CNC(=O)c1c(-c2ccc(F)cc2)oc2cc(N(C)S(C)(=O)=O)c(-c3cc4c(=O)n(Cc5ccc(F)cc5)nnc4cc3Cl)cc12] | 5-[7-chloro-3-(4-fluorobenzyl)-4-oxo-3,4-dihydro-1,2,3-benzotriazin-6-yl]-2-(4-fluorophenyl)-N-methyl-6-[methyl(methylsulfonyl)amino]-1-benzofuran-3-carboxamide | 664 |
| 74 | 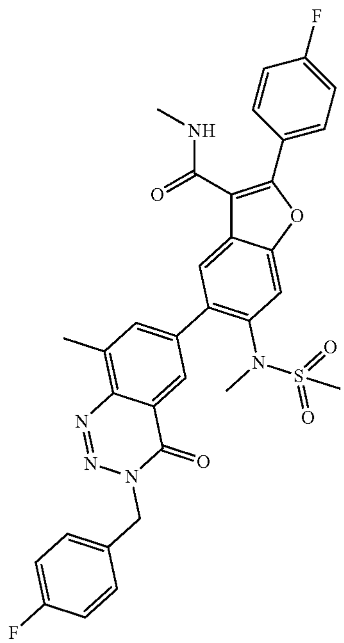 [SMILES: CNC(=O)c1c(-c2ccc(F)cc2)oc2cc(N(C)S(C)(=O)=O)c(-c3cc(C)c4nnn(Cc5ccc(F)cc5)c(=O)c4c3)cc12] | 5-[3-(4-fluorobenzyl)-8-methyl-4-oxo-3,4-dihydro-1,2,3-benzotriazin-6-yl]-2-(4-fluorophenyl)-N-methyl-6-[methyl(methylsulfonyl)amino]-1-benzofuran-3-carboxamide | 644 |

Example 75

Measuring Compound Inhibitory Potency

Measurement of inhibition by compounds was performed using the HCV replicon system. Several different replicons encoding different HCV genotypes or mutations were used. In addition, potency measurements were made using different formats of the replicon assay, including different ways of measurements and different plating formats. See Jan M. Vrolijk et al., *A replicons-based bioassay for the measurement of interferons in patients with chronic hepatitis C*, 110 J. VIROLOGICAL METHODS 201 (2003); Steven S. Carroll et al., *Inhibition of Hepatitis C Virus RNA Replication by 2'-Modified Nucleoside Analogs*, 278(14) J. BIOLOGICAL CHEMISTRY 11979 (2003). However, the underlying principles are common to all of these determinations, and are outlined below.

Stable neomycin phosphotransferase encoding replicons-harboring cell lines were used, so all cell lines were maintained under G418 selection prior to the assay. Potency was deteremined using a cell ELISA assay with an antibody to the replicons encoded NS3/4a protease. See Caterina Trozzi et al., *In Vitro Selection and Characterization of Hepatitis C Virus Serine Protease Variants Resistant to an Active-Site Peptide Inhibitor*, 77(6) J. Virol. 3669 (2003). To initiate an assay, replicon cells were plated in the presence of a dilution series of test compound in the absence of G418. Typically, the assays were performed in a 96-well plate formate for manual operation, or a 384-well plate format for automated assay. Replicon cells and compound were incubated for 96 hours. At the end of the assay, cells were washed free of media and compound, and the cells were then lysed. RNA was quantified indirectly through detection of replicon-encoded NS3/4A protein levels, through an ELISA-based assay with an antibody specific for NS3/4A. $IC_{50}$ determinations were calculated as a percentage of a DMSO control by fitting the data to a four-parameter fit function and the data obtained is provided in the table below.

Data for selected compounds of the present invention was obtained for genotypes 1a and 1b using this method and is provided in the table below:

| Compound No. | 1a $IC_{50}$ (nM) | 1b $IC_{50}$ (nM) |
|---|---|---|
| 1 | 3.218 | 2.435 |
| 2 | 24.83 | 3.341 |
| 3 | 4.826 | 2.842 |
| 4 | 39.9 | 15.22 |
| 5 | 3.055 | 1.592 |
| 6 | 2.782 | 1.933 |
| 7 | 1.481 | 1.063 |
| 8 | 5.873 | 2.618 |
| 9 | 8.032 | 3.912 |
| 10 | 0.7678 | 1.79 |
| 11 | 15.32 | 7.68 |
| 12 | 7.019 | 2.953 |
| 13 | 2.551 | 2.059 |
| 14 | 434.9 | 35.9 |
| 15 | 395.4 | 39.17 |
| 16 | 128.4 | 39.19 |
| 17 | 161.5 | 48.53 |
| 18 | 10.51 | 3.737 |
| 19 | 1.601 | 1.747 |
| 20 | 4.936 | 2.794 |
| 21 | 6.321 | 2.509 |
| 22 | 16.24 | 4.123 |
| 23 | 3.978 | 3.24 |
| 24 | 2.588 | 2.571 |
| 25 | 16.33 | 11.89 |
| 26 | 44.65 | 5.887 |
| 27 | 352.9 | 567.7 |
| 28 | 4.957 | 4.17 |
| 29 | 7.211 | 0.8856 |
| 30 | 0.9806 | 2.227 |
| 31 | 41.78 | 12.49 |
| 33 | 708.3 | 1692 |
| 34 | 8928 | 10430 |
| 35 | 2.147 | 1.709 |
| 36 | 1.081 | 0.527 |
| 37 | 77.35 | 11.42 |
| 38 | 1.375 | 1.139 |
| 39 | 4.035 | 9.268 |
| 40 | 6.19 | 9.029 |
| 41 | 18.13 | 16.22 |
| 42 | 9.482 | 9.549 |
| 43 | 15.08 | 9.659 |
| 44 | 5.619 | 10.53 |
| 45 | 35.03 | 17.5 |
| 46 | 7.646 | 10.17 |
| 47 | 20.16 | 20.64 |
| 48 | 6.928 | 5.971 |
| 49 | 6.245 | 10.19 |
| 50 | 3.176 | 4.227 |
| 51 | 8.978 | 2.351 |
| 52 | 6.369 | 2.112 |
| 53 | 2.566 | 2.45 |
| 54 | 2.343 | 2.725 |
| 55 | 1.934 | 2.421 |
| 57 | 9.65 | 9.816 |
| 63 | 23.72 | 8.996 |
| 64 | 4.122 | 3.629 |
| 65 | 9.279 | 2.947 |
| 66 | 7.286 | 4.059 |
| 67 | 4.971 | 3.768 |

-continued

| Compound No. | 1a $IC_{50}$ (nM) | 1b $IC_{50}$ (nM) |
|---|---|---|
| 68 | 2.004 | 2.244 |
| 69 | 6.645 | 10.06 |
| 70 | 11.3 | 2.609 |
| 71 | 3.486 | 0.7817 |
| 72 | 8.621 | 6.475 |
| 73 | 11.59 | 7.652 |
| 74 | 11.94 | 7.079 |

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A compound having the formula:

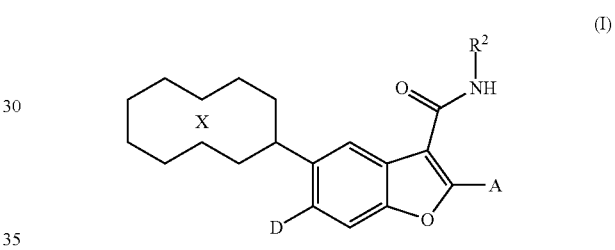

or a pharmaceutically acceptable salt thereof, wherein:

X is

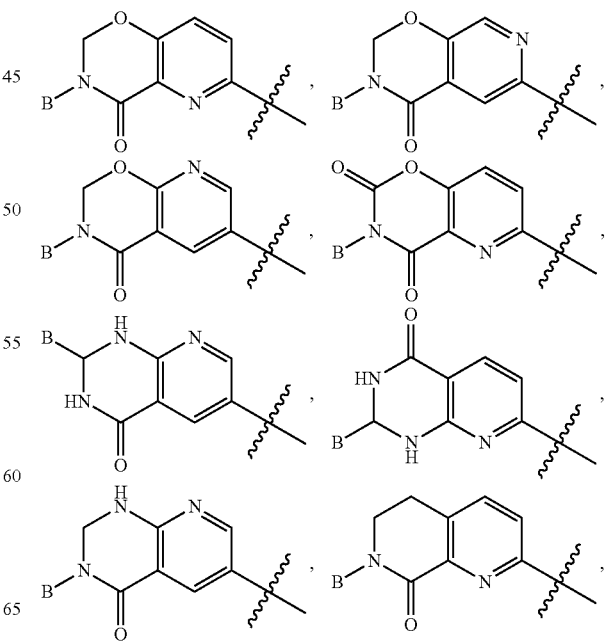

-continued

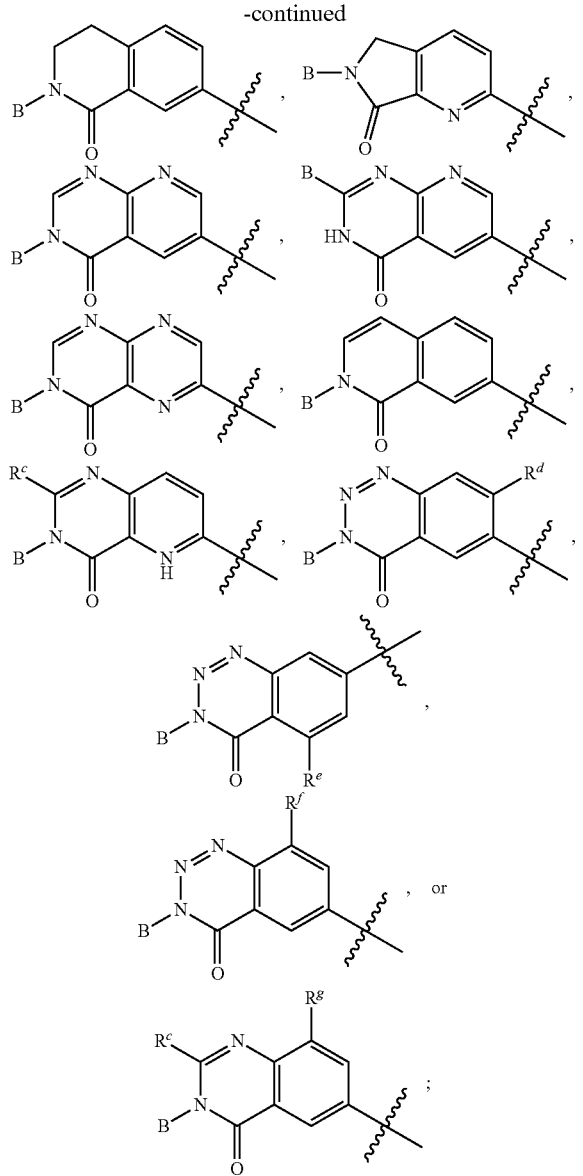

A is fluorophenyl;
B is a) hydrogen;
  b) Ar;
  c) $C_1$-$C_6$ alkyl-Ar;
  d) —CHR$^a$—Ar; or
  e) cyclopropyl;
Ar is a 5-6 membered monocyclic aromatic ring with 0 or 1 heteroatom ring atoms independently selected from N and S, optionally substituted with 1 or 2 substituents independently selected from $C_1$-$C_6$ alkoxy, halo, and cyano;
D is H or NR$^3$SO$_2$R$^4$;
R$^2$ is $C_1$-$C_6$ alkyl;
R$^3$ is $C_1$-$C_6$ alkyl;
R$^4$ is $C_1$-$C_6$ alkyl;
R$^a$ is $C_1$-$C_6$ hydroxyalkyl, or alkylalkoxy;
R$^c$ is hydrogen, $C_1$-$C_6$ alkyl, alkylalkoxy, or —CH$_2$NHC(O)CH$_3$;
R$^d$ is hydrogen, F, Cl or $C_1$-$C_6$ alkyl;
R$^e$ and R$^f$ are independently hydrogen or $C_1$-$C_6$ alkyl; and
R$^g$ is hydrogen or $C_1$-$C_6$ alkoxy.

2. The compound of claim 1, wherein R$^2$, R$^3$ and R$^4$ are methyl.

3. The compound of any one of claims 1 to 2, wherein D is N(CH$_3$)SO$_2$CH$_3$.

4. The compound of any one of claims 1 to 3, wherein each halo is F.

5. The compound of any one of claims 1 to 4, wherein B is —CH$_2$—Ar, —CH$_2$CH$_2$—Ar, —CH(CH$_3$)—Ar, or —C(CH$_3$)$_2$—Ar.

6. The compound of claim 1, or a pharmaceutically acceptable salt thereof, having the formula:

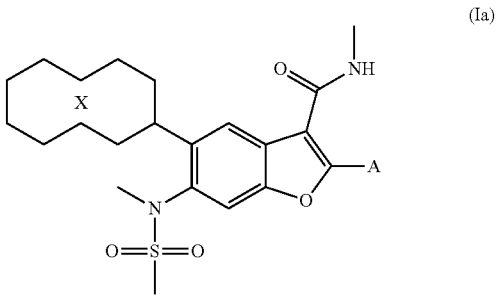

(Ia)

or a pharmaceutically acceptable salt thereof.

7. The compound of any one of claims 1 to 6, wherein X is

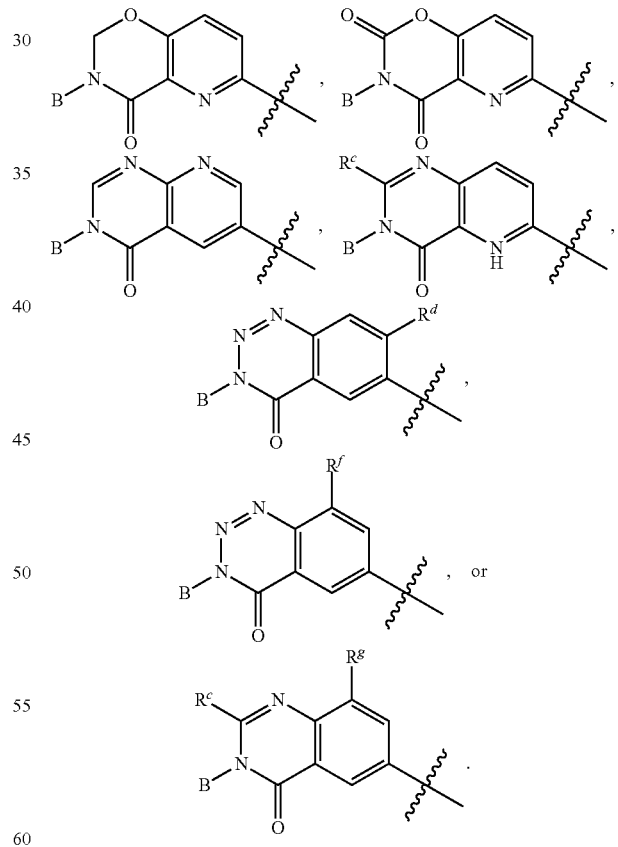

8. The compound of any one of claims 1 to 7, wherein R$^c$ is hydrogen or methyl and R$^g$ is hydrogen.

9. The compound of any one of claims 1 to 4 or 6 to 8, wherein B is
hydrogen;
phenyl;

fluorophenyl;
—(CH$_2$)$_{1-2}$-phenyl;
—CH$_2$-fluorophenyl;
—CH(CH$_3$)-fluorophenyl;
—C(CH$_3$)$_2$-fluorophenyl;
—CH$_2$-chlorophenyl;
—CH$_2$-phenyl-OCH$_3$;
—CH$_2$-phenyl-cyano;
—CH$_2$-fluoropyridine;
thiophene;
cyclopropyl;
—CH(CH$_2$OCH$_3$)-fluorophenyl;
—CH(CH$_2$OH)-phenyl;
—CH(CH$_2$OH)-fluorophenyl;
—CH(CH$_2$CH$_2$OH)-fluorophenyl;
—CH$_2$-4-fluoro-2-methoxyphenyl; or
—CH$_2$-difluorophenyl.

10. The compound of claim 1 which is any one of

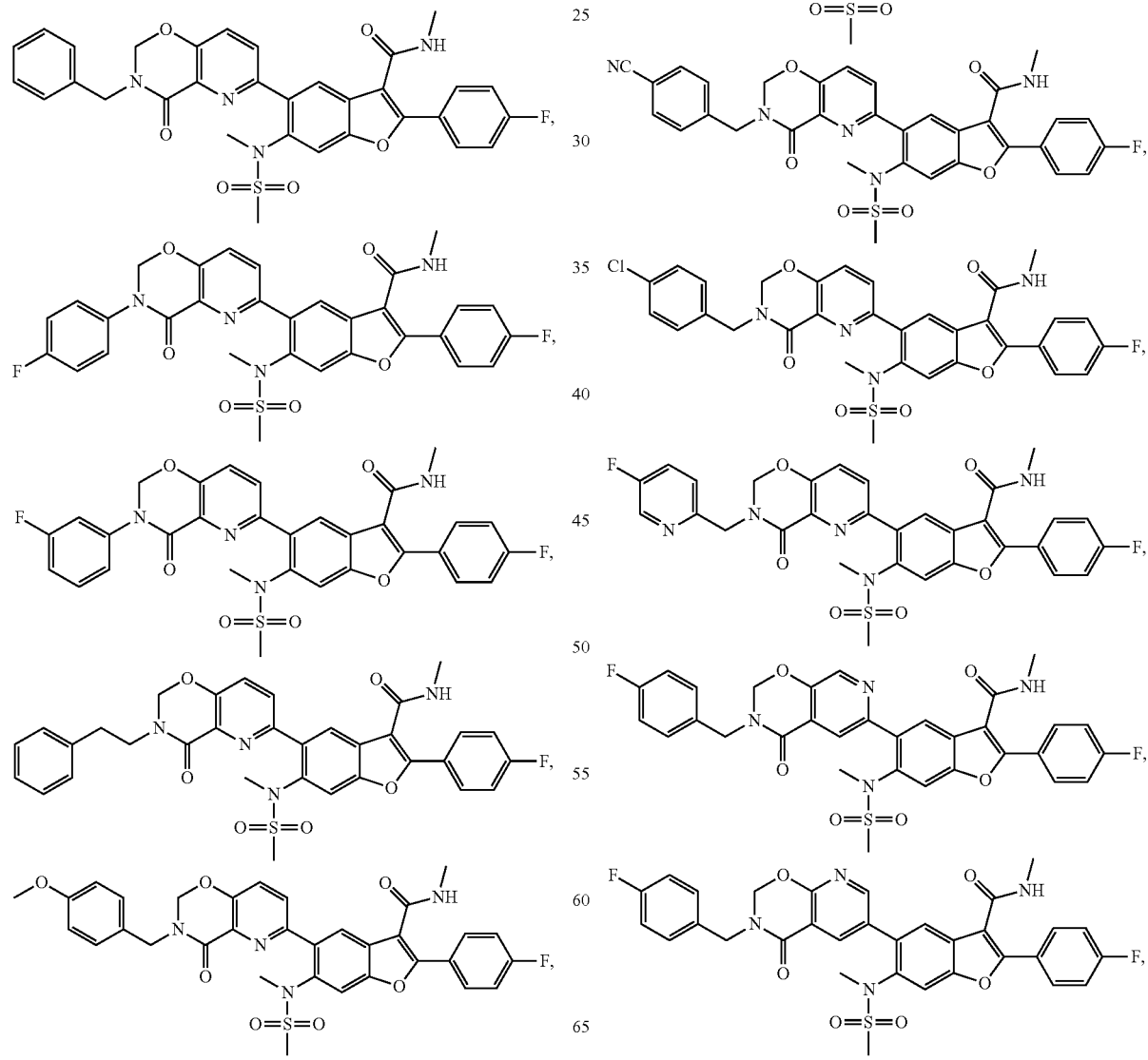
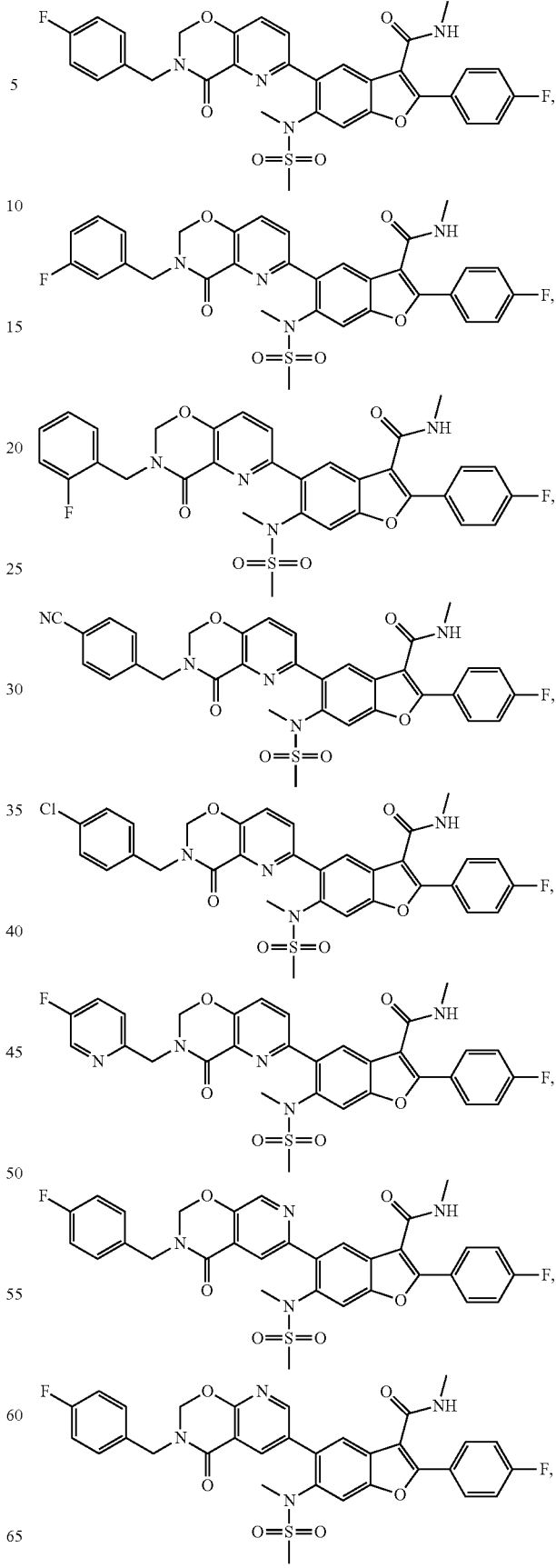

151
-continued
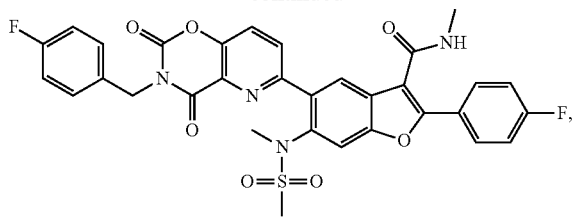
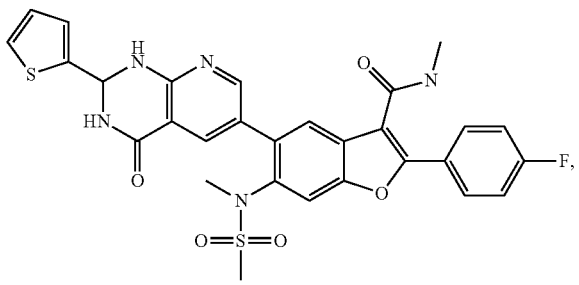
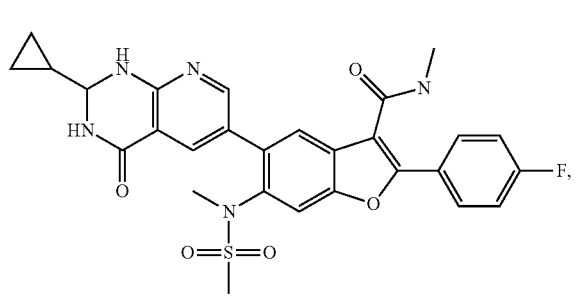
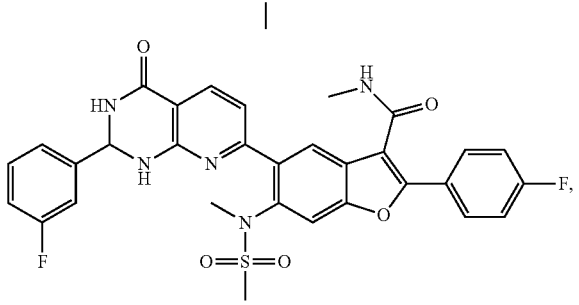
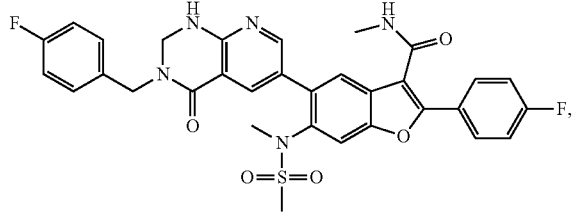
152
-continued
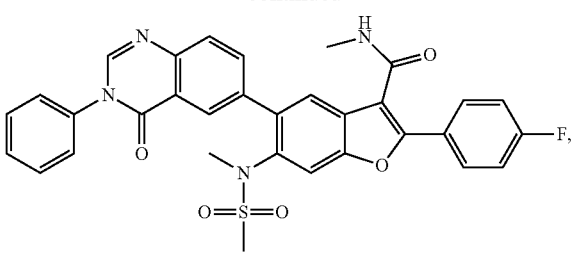
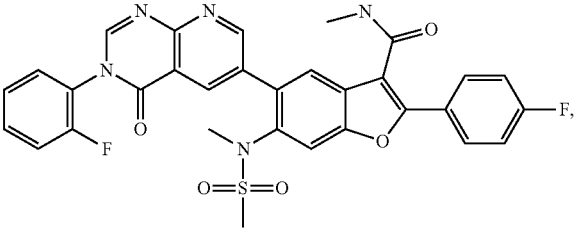
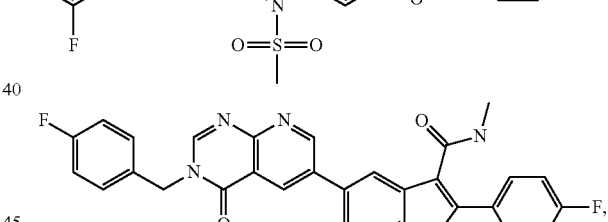
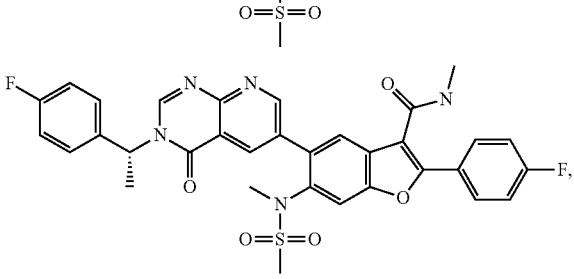

153
-continued
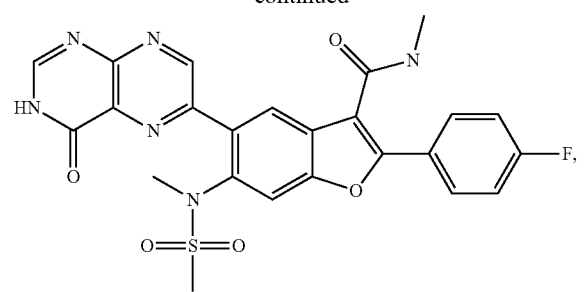
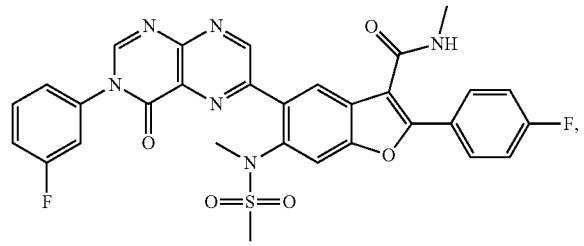
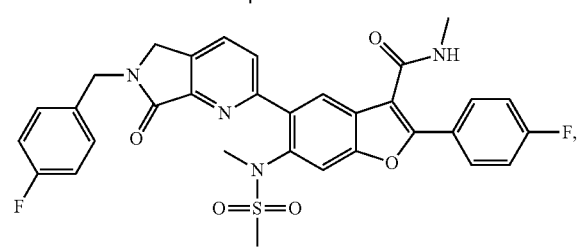
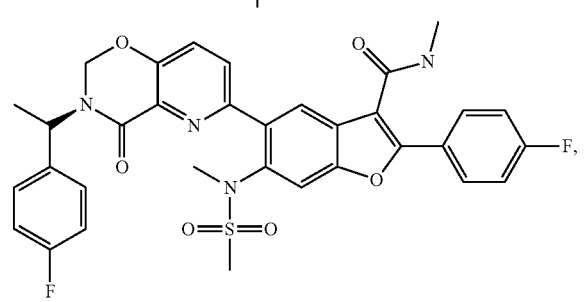
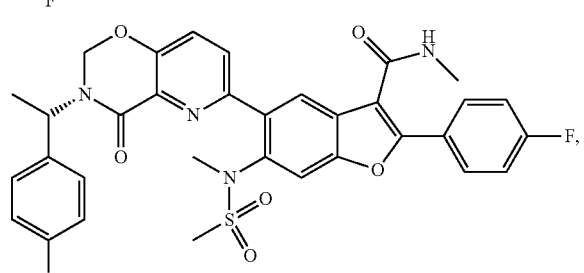
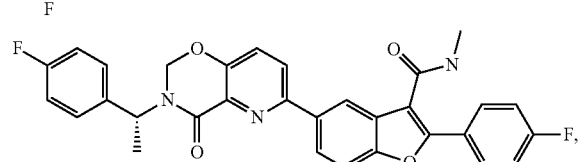
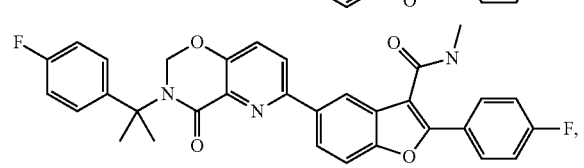
154
-continued
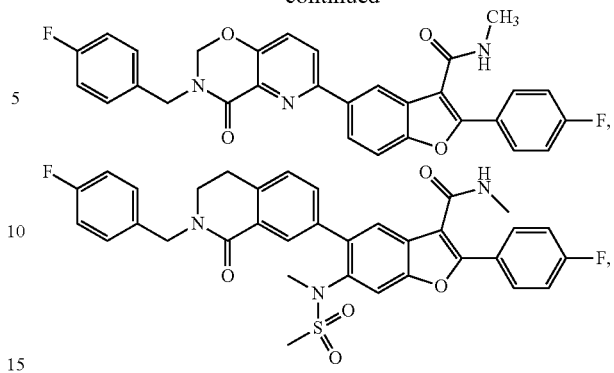
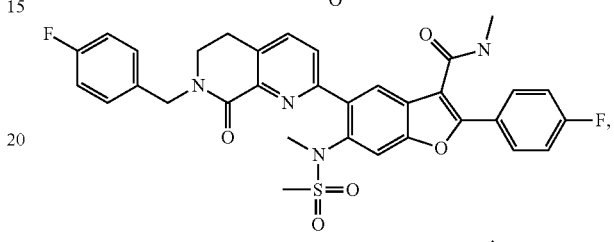
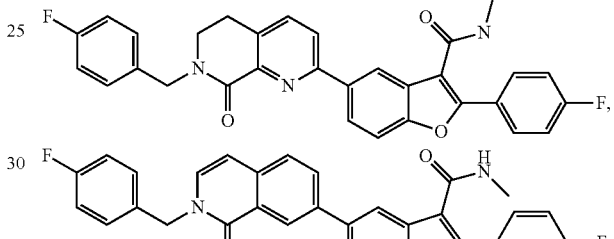
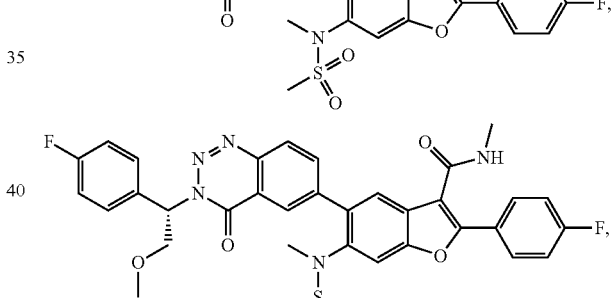
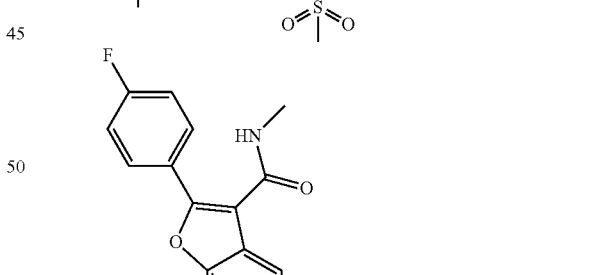
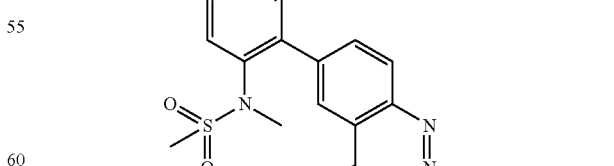
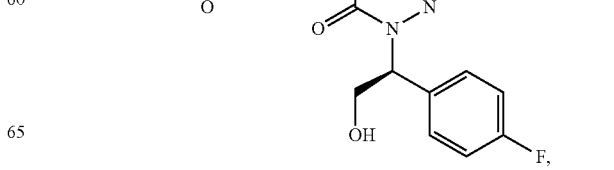

155
-continued
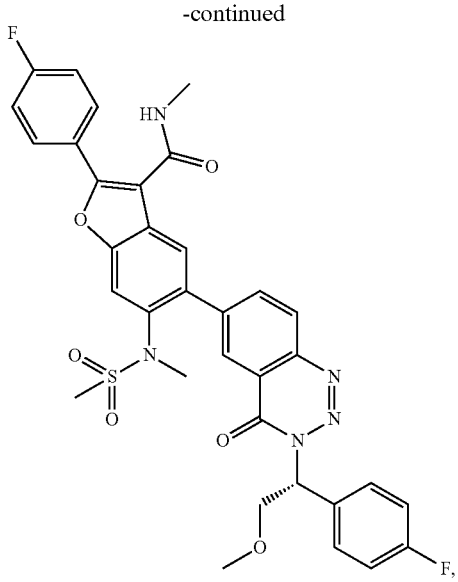
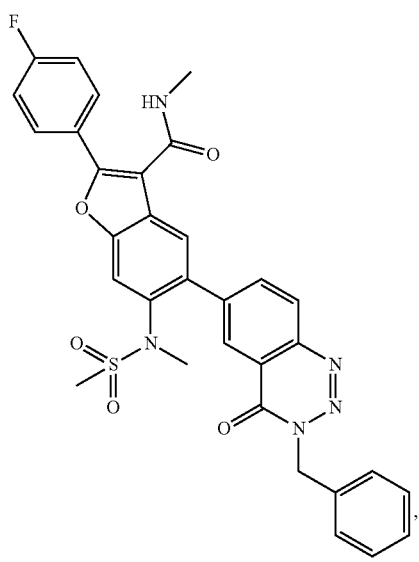
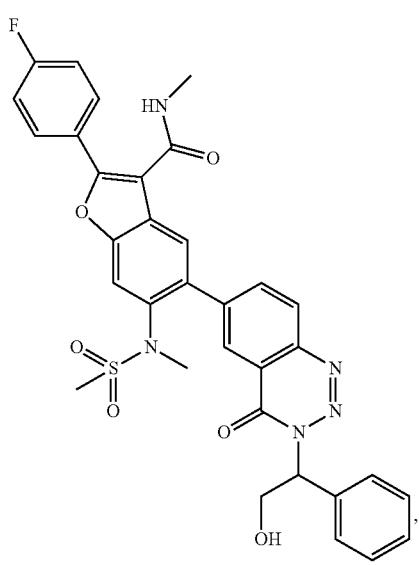
156
-continued
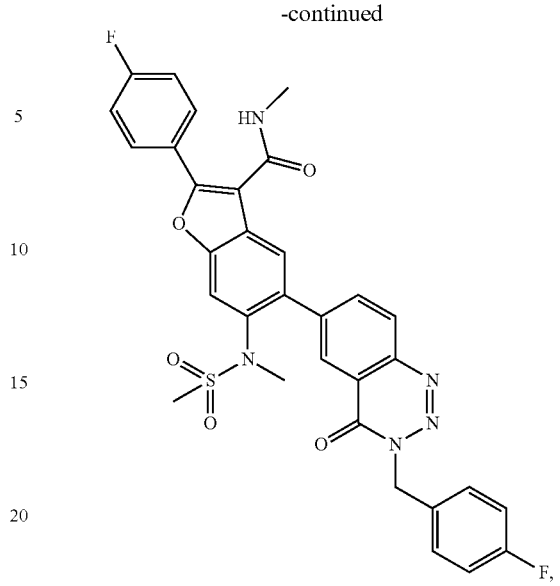
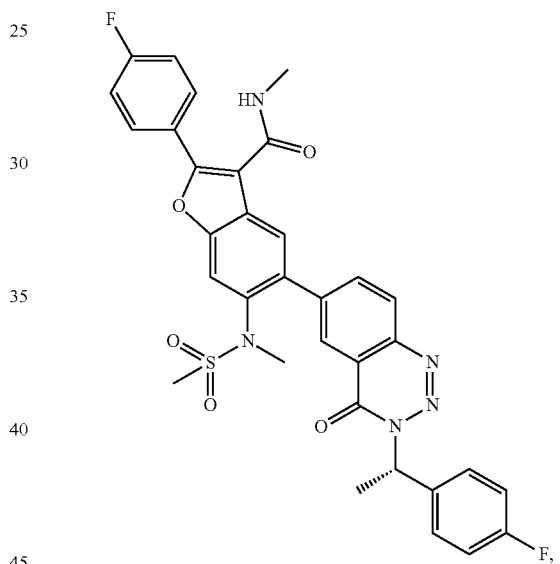
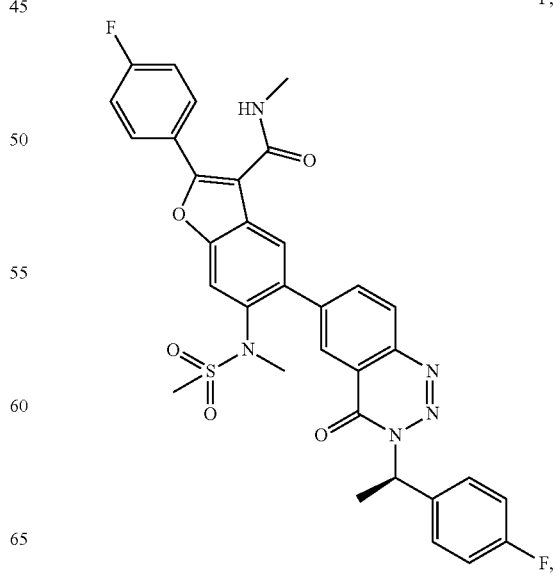

157
-continued
158
-continued
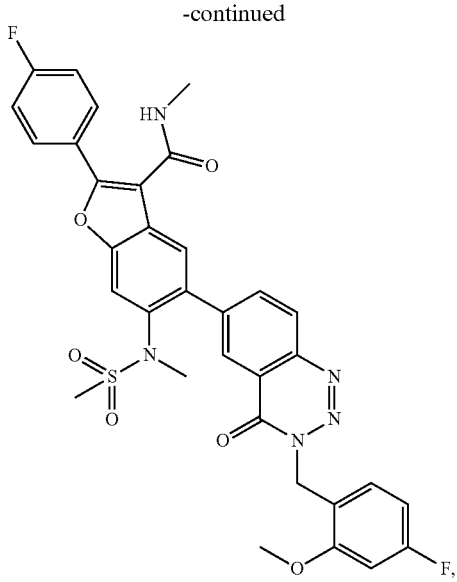
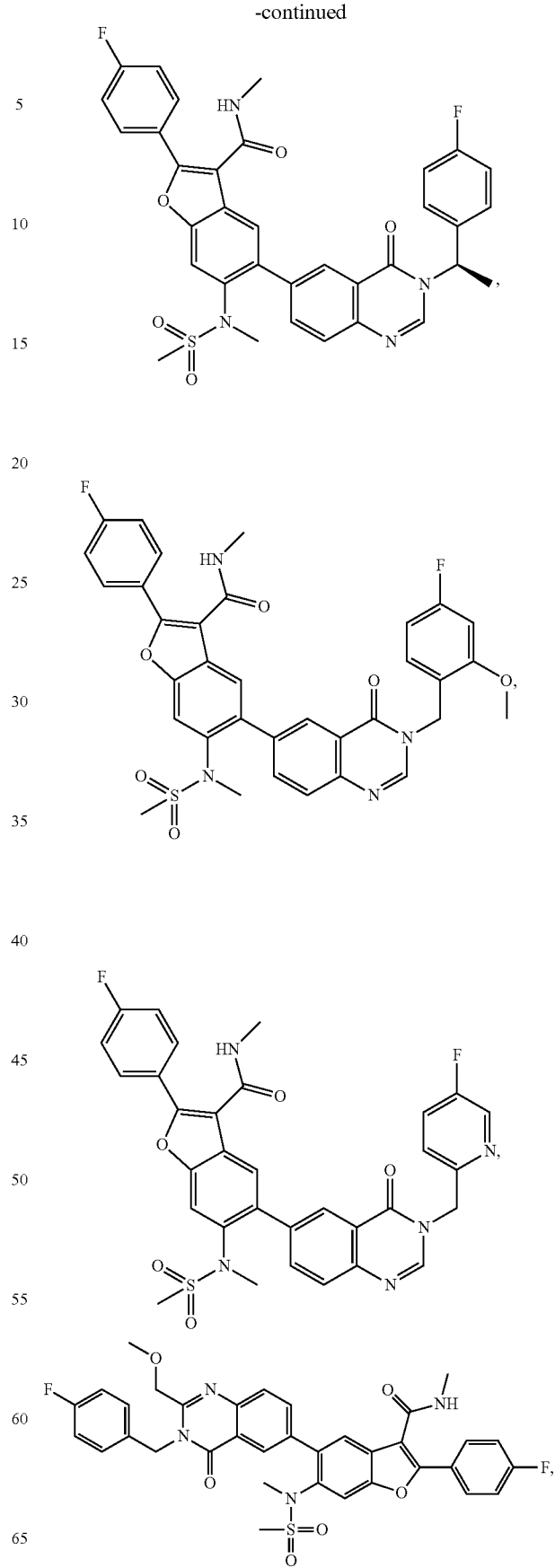

159
-continued
160
-continued
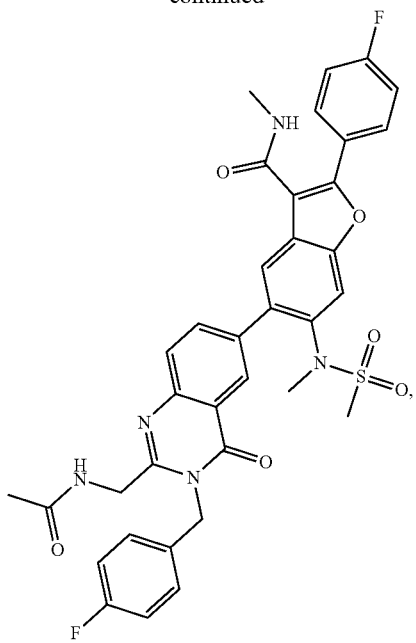
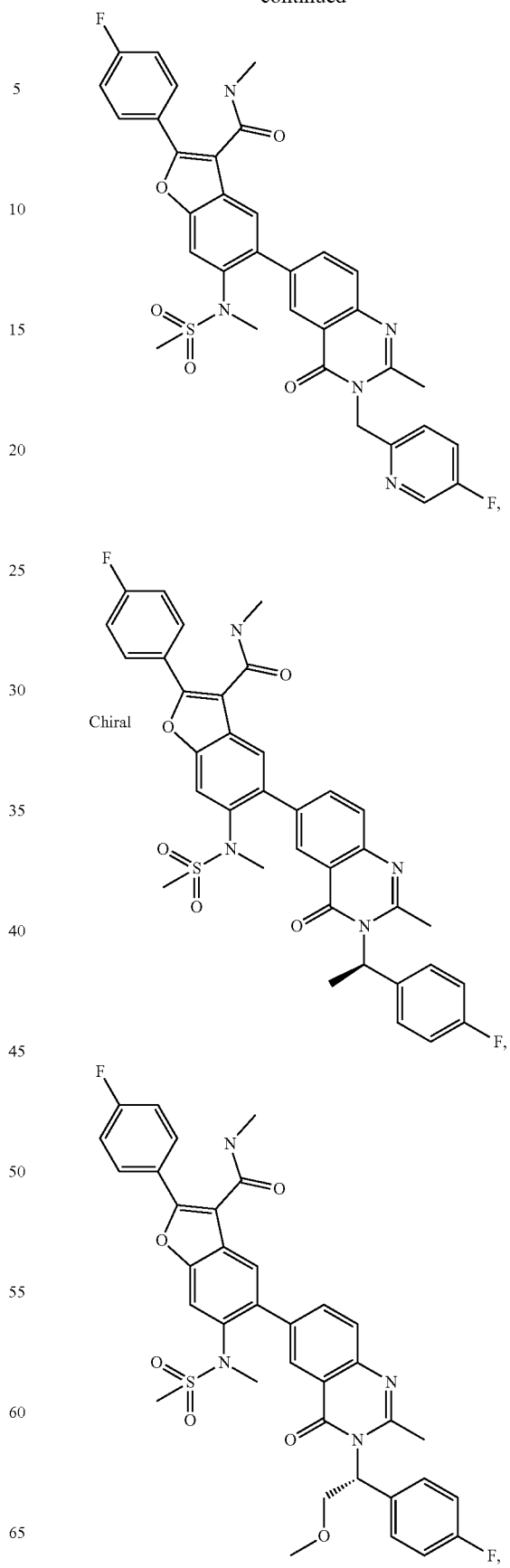

161
-continued
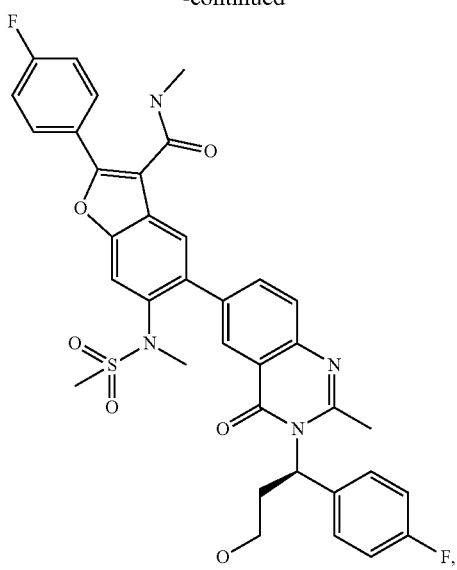
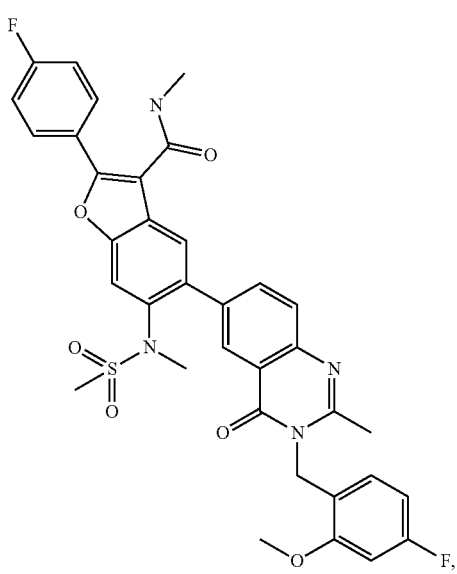
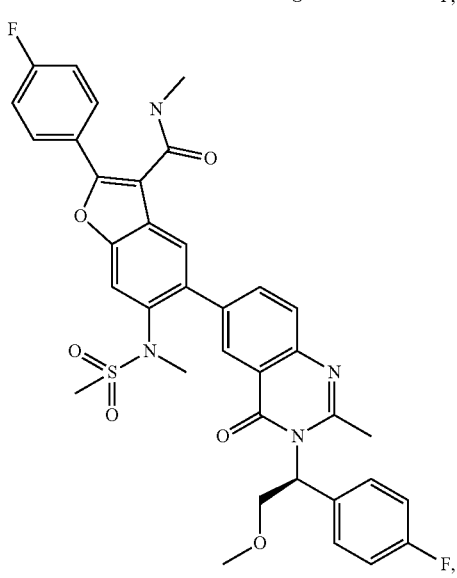
162
-continued
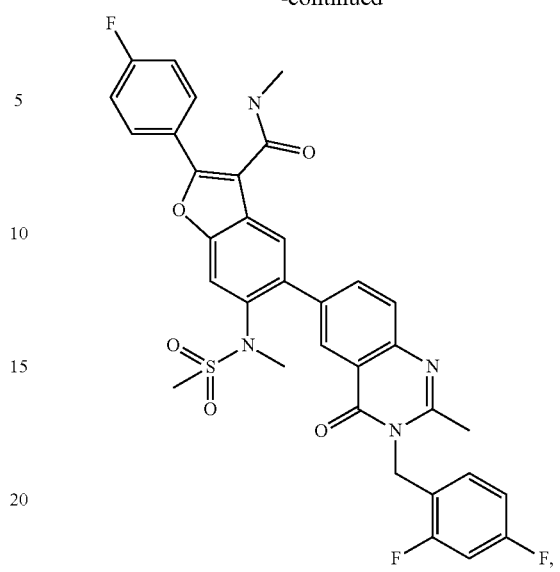
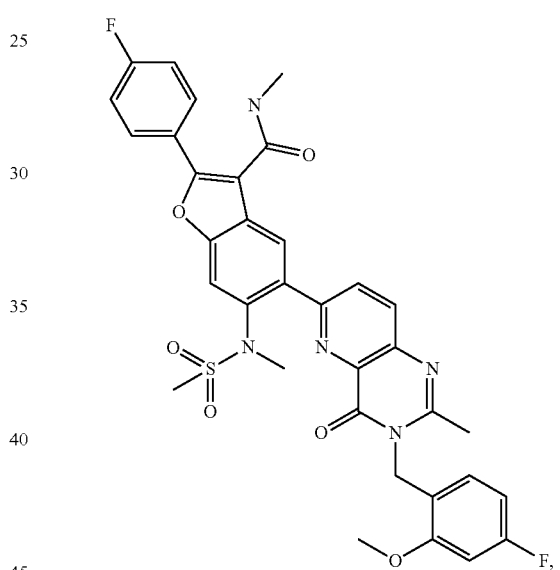
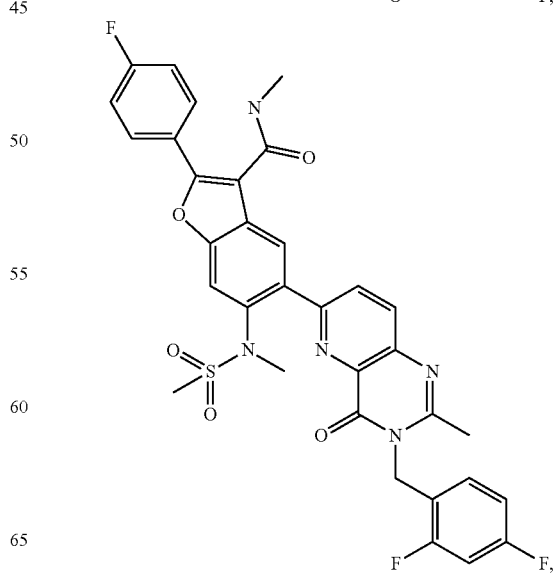

163
-continued
164
-continued
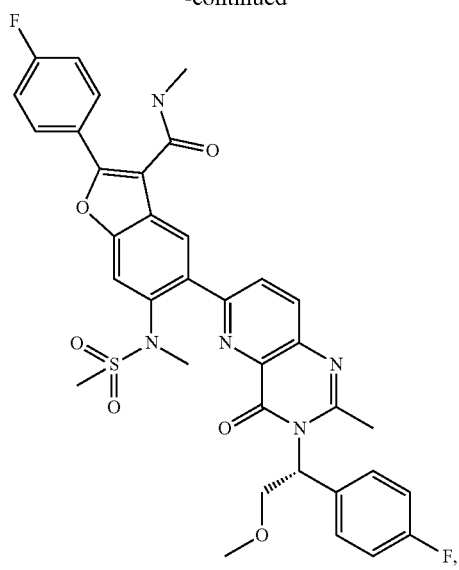
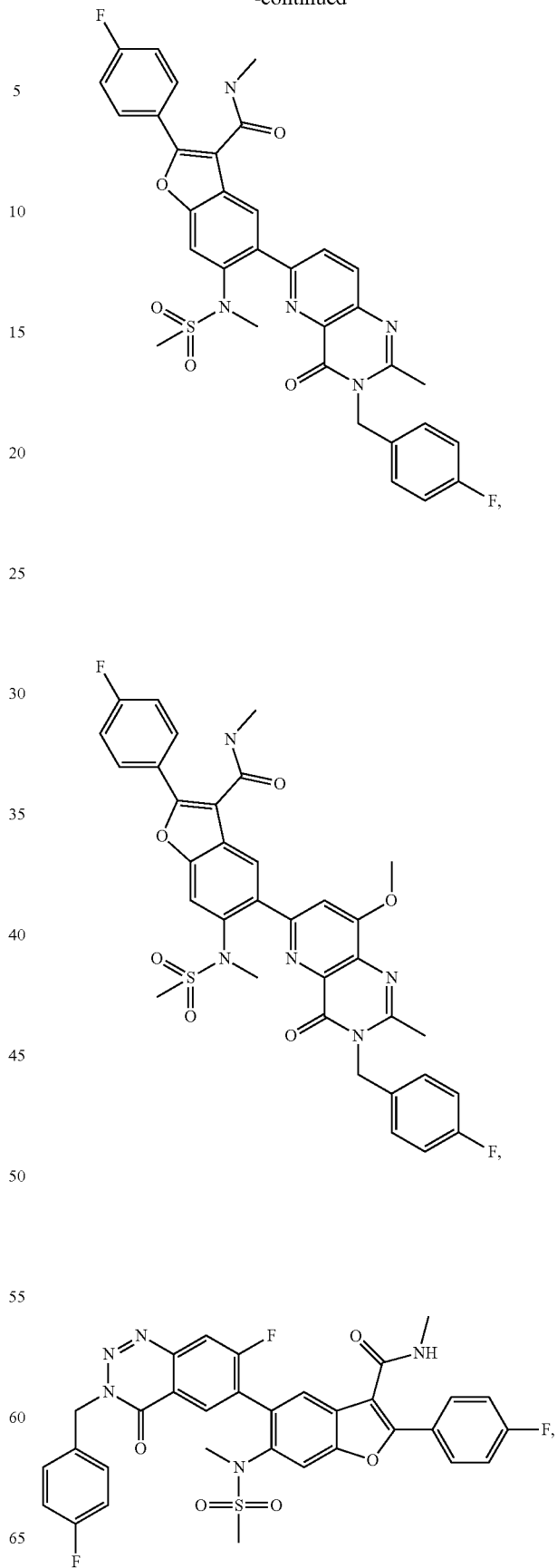

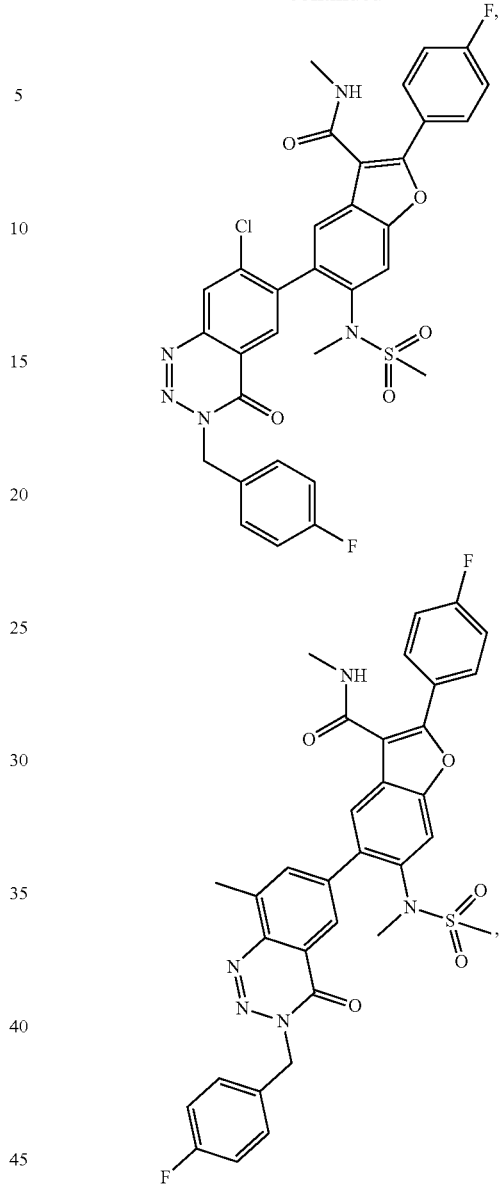

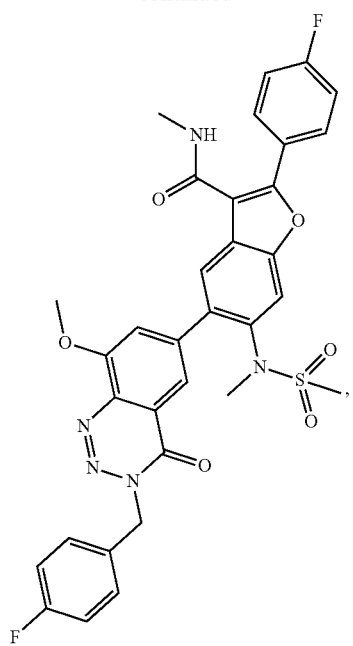

or a pharmaceutically acceptable salt thereof.

11. A pharmaceutical composition comprising (i) a pharmaceutically acceptable carrier and (ii) an effective amount of the compound of any one of claims 1-10 or a pharmaceutically acceptable salt thereof.

12. The pharmaceutical composition of claim 11, further comprising a second therapeutic agent selected from the group consisting of HCV antiviral agents, immunomodulators, and anti-infective agents.

13. The pharmaceutical composition of claim 12, wherein the second therapeutic agent is selected from the group consisting of HCV NS3 and NS3/4A protease inhibitors, HCV NS5A inhibitors and HCV NS5B polymerase inhibitors.

14. A method of treating a patient infected with HCV, the method comprising administering to the patient the compound of any one of claims 1 to 10, or a pharmaceutically acceptable salt thereof, in an amount effective to prevent and/or treat infection by HCV in the patient.

15. The method of claim 14, further comprising administering to said patient an effective amount of at least one second therapeutic agent selected from the group consisting of HCV NS3 and NS3/4A protease inhibitors, HCV NS5A inhibitors and HCV NS5B polymerase inhibitors.

* * * * *